(12) United States Patent
Bouvier et al.

(10) Patent No.: US 10,877,036 B2
(45) Date of Patent: Dec. 29, 2020

(54) BIOSENSOR BASED ON Gβγ-INTERACTING PROTEINS TO MONITOR G-PROTEIN ACTIVATION

(71) Applicant: UNIVERSITÉ DE MONTRÉAL, Montréal (CA)

(72) Inventors: Michel Bouvier, Montréal (CA); Christian Le Gouill, Montréal (CA); Mireille Hogue, Laval (CA); Viktoriya Lukasheva, Pointe-Claire (CA)

(73) Assignee: UNIVERSITÉ DE MONTRÉAL, Québec (CA)

( * ) Notice: Subject to any disclaimer, the term of this patent is extended or adjusted under 35 U.S.C. 154(b) by 390 days.

(21) Appl. No.: 15/518,888

(22) PCT Filed: Oct. 14, 2015

(86) PCT No.: PCT/CA2015/051032
§ 371 (c)(1),
(2) Date: Apr. 13, 2017

(87) PCT Pub. No.: WO2016/058094
PCT Pub. Date: Apr. 21, 2016

(65) Prior Publication Data
US 2017/0234870 A1 Aug. 17, 2017

Related U.S. Application Data

(60) Provisional application No. 62/063,622, filed on Oct. 14, 2014.

(51) Int. Cl.
| | |
|---|---|
| *G01N 33/566* | (2006.01) |
| *C07K 14/47* | (2006.01) |
| *G01N 33/542* | (2006.01) |
| *C07K 14/72* | (2006.01) |
| *C12Q 1/66* | (2006.01) |
| *G01N 21/64* | (2006.01) |
| *C12N 9/02* | (2006.01) |

(52) U.S. Cl.
CPC ....... *G01N 33/566* (2013.01); *C07K 14/4722* (2013.01); *C07K 14/723* (2013.01); *C12N 9/0069* (2013.01); *C12Q 1/66* (2013.01); *C12Y 113/12007* (2013.01); *G01N 21/6428* (2013.01); *G01N 33/542* (2013.01); *C07K 2319/00* (2013.01); *C07K 2319/01* (2013.01); *C07K 2319/60* (2013.01); *G01N 2021/6439* (2013.01); *G01N 2333/4719* (2013.01); *G01N 2333/726* (2013.01); *G01N 2500/02* (2013.01)

(58) Field of Classification Search
CPC .............. C07K 14/723; C07K 14/4722; C07K 2319/00; C07K 2319/01; C07K 2319/60; C12Q 1/66; G01N 33/566; G01N 21/6428
See application file for complete search history.

(56) References Cited

U.S. PATENT DOCUMENTS

| | | |
|---|---|---|
| 2005/0042720 A1 | 2/2005 | Kostenis |
| 2005/0181452 A1 | 8/2005 | Westwick et al. |

FOREIGN PATENT DOCUMENTS

| | | |
|---|---|---|
| WO | WO 05/121755 | 12/2005 |
| WO | WO 2012/063832 A1 | 6/2010 |
| WO | WO 10/112417 | 10/2010 |
| WO | WO 2015/095973 A1 | 7/2015 |

OTHER PUBLICATIONS

European Search Report corresponding to European Patent Application No. EP 15 85 1395 dated Mar. 26, 2018.
Kaczor et al., "Application of BRET for Studying G Protein-Coupled Receptors," Mini Reviewed in Medicinal Chemistry, vol. 14, No. 5 (May 31, 2014).
Boularan et al., "Implications of Non-Canonical G-protein signaling for the Immune System," Cell Signal, vol. 26, No. 6, pp. 1269-1282 (Jun. 2014).
Breton et al., "Combining resonance energy transfer methods reveals a complex between the (2A-adrenergic receptor,G(i1β1(2, and GRK2," FASEB Journal, vol. 24, pp. 4733-4747 (Dec. 2010).
Choudhary et al., "Mislocalized Activation of Oncogenic RTKs Switches Downstream Signaling Outcomes," Molecular Cell, vol. 36, pp. 326-339 (Oct. 23, 2009).
Cong et al., "Regulation of Membrane Targeting of the G Protein-coupled Receptor Kinase 2 by Protein Kinase A and Its Anchoring Protein AKAP79," The Journal of Biological Chemistry, vol. 276, No. 18, pp. 15192-15199 (May 4, 2001).
Galandrin et al., "The evasive nature of drug efficacy: implications for drug discovery," Trends in Pharmacological Sciences, vol. 28, No. 8, pp. 423-430 (Jul. 2007).

(Continued)

*Primary Examiner* — Ruixiang Li
(74) *Attorney, Agent, or Firm* — Jenkins, Wilson, Taylor & Hunt, P.A.

(57) ABSTRACT

Resonance energy transfer (RET)- or protein-fragment complement assay (PCA)-based biosensors useful for assessing the activity of G-proteins are described. These biosensors are based on the competition between the Gα subunit and a Gβγ interacting protein (βγ IP) for the binding to the Gβγ dimer. These biosensors comprises (1) a βγ IP and (2) a Gβ or Gγ protein; a GPCR; or a plasma membrane targeting domain, fused to suitable RET or PCA tags. Methods using such biosensors for different applications, including the identification of agents that modulates G-protein activity or for the characterization of GPCR signaling/regulation, such as G-protein preferences and activation profiles of GPCRs, are also described.

17 Claims, 27 Drawing Sheets

Specification includes a Sequence Listing.

(56) References Cited

OTHER PUBLICATIONS

Gales et al., "Real-time monitoring of receptor and G-protein teractions in living cells," Nature Methods, vol. 2, No. 3, pp. 177-184 (Mar. 2005).
Garland, "Are GPCRs Still a Source of New Targets?," Journal of Biomolecular Screening, vol. 18, No. 9, pp. 947-966 (Aug. 14, 2013).
Gilman, "G Proteins: Transducers of Receptor-Generated Signals," Ann. Rev. Biochem., vol. 56, pp. 615-649 (1987).
Hamdan et al., "Unraveling G Protein-coupled Receptor Endocytosis Pathways Using Real-time Monitoring of Agonist-promotedInteraction between β-Arrestins and AP-2," Jorn. Biol. Chem., vol. 282, No. 40, pp. 29089-29100 (Oct. 5, 2007).
Hancock, "RAS Proteins: Different Signals from Different Locations," Nature Reviews, Molecular Cell Biology, vol. 4, pp. 373-384 (May 2003).
Heydorn, "Identification of a Novel Site within G Protein ( Subunits Important for Specificity of Receptor-G Protein Interaction," Molecurlar Pharmacology, vol. 66, No. 2, pp. 250-259 (2004).
Kenakin et al., "Signalling bias in new drug discovery: detection, quantification and therapeutic impact," Nature Reviews, vol. 12, pp. 205-216 (Mar. 2013).
Leduc, et al., "Functional Selectivity of Natural and Synthetic Prostaglandin EP4 Receptor Ligands," The Journal of Pharmacology and Experimental Therapeutics, vol. 331, No. 1, pp. 297-307 (2009).
Lima-Fernandes et al., "A biosensor to monitor dynamic regulation and unction of tumour suppressor PTEN in living cells," Nature Communications, pp. 1-12 (Jul. 16, 2014).
Linding et al., "GlobPlot: exploring protein sequences for globularity and disorder," Nucleic Acids Research, vol. 31, No. 13, pp. 3701-3708 (2003).
Mercier et al., "Quantitative Assessment of β1- and β2-Adrenergic Receptor Homo-and Heterodimerization by Bioluminescence Resonance Energy Transfer," The Journal of Biological Chemistry, vol. 277, No. 47, pp. 44925-44931 (2002).

Notification of Transmittal of the International Search Report and the Written Opinion of the International Searching Authority for the International Application No. PCT/CA2015/051032 dated Jan. 26, 2016.
Penela et al., "G protein—coupled receptor kinase 2 (GRK2) modulation and cell cycle progression," PNAS, vol. 107, No. 3, pp. 1118-1123 (Jan. 19, 2010).
Pitcher et al., "Role of β( Subunits of G Proteins in Targeting the β-Adrenergic Receptor Kinase to Membrane-Bound Receptors," Science, vol. 257, pp. 1264-1267 (Aug. 28, 1992).
Pitcher et al., "Feedback Inhibition of G Protein-coupled Receptor Kinase 2 (GRK2) Activity by Extracellular Signal-regulated Kinases," Journal of Bio. Chem., vol. 274, No. 49, pp. 34531-34534 (1999).
Stefan et al., "Quantification of dynamic protein complexes using Renilla luciferase fragment complementation applied to protein kinase A activities in vivo," PNAS, vol. 104, No. 43, pp. 16916-16921 (Oct. 23, 2007).
Takasaki et al., A Novel G(q/11-selective Inhibitor, Journal of Bio. Chem., vol. 279, pp. 47438-47445 (Aug. 31, 2004).
Touhara et al., "Binding of G Protein β(-Subunits to Pleckstrin Homology Domains," Journal of Bio. Chem., vol. 269, No. 14, pp. 10217-10220 (1994).
Van Unen et al., "A Perspective on Studying G-Protein-Coupled Receptor Signaling with Resonance Energy Transfer Biosensors in Living Organisms," Molecular Pharmacology, vol. 88, pp. 589-595 (2015).
Zhang et al., "A Simple Statistical Parameter for Use in Evaluation and Validation of High Throughput Screening Assays," Journal of Biomolecular Screening, vol. 4, No. 2, pp. 67-73 (1999).
Jorgensen et al., "Oxyntomodulin Differentially Affects Glucagon-Like Peptide-1 Receptor β-Arrestin Recruitment and Signaling through Gαs," Journal of Pharmacology and Experimental Therapeutics, vol. 322, No. 1, pp. 148-154 (2007).
Office Action corresponding to Japanese Patent Application No. 2017-520506 dated Oct. 29, 2019 (with Translation).
International Preliminary Report on Patentability corresponding to International Application No. PCT/CA2015/051032 dated Apr. 18, 2017.
Ouyang et al., "Simultaneous Visualization of Protumorigenic Src and MT1-MMP Activities with Fluorescence Resonance Energy Transfer," Cancer Research, vol. 70, No. 6, pp. 2204-2212 (2010).

Structure of GRK2 & 3:
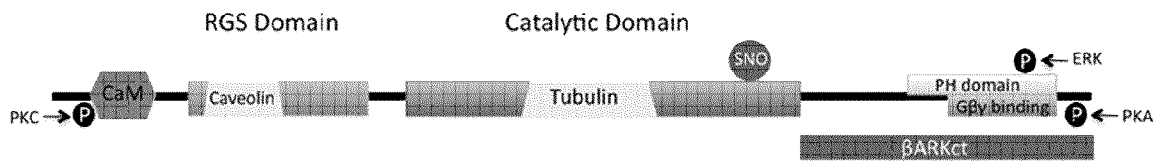
Constructs:
GRK2 &3:
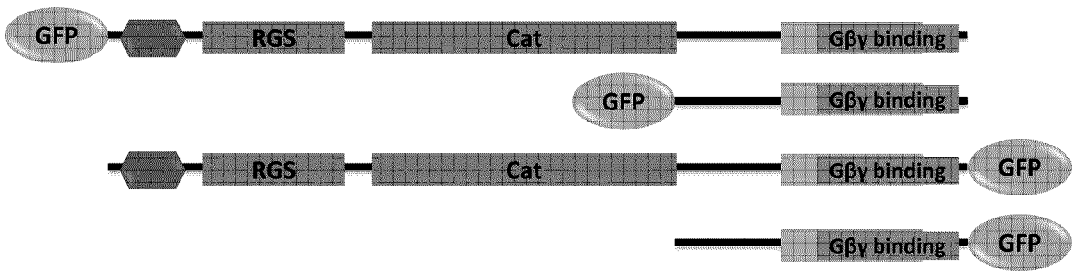
GFP10-Gγ5: 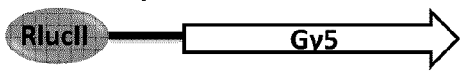   GFP10-Gβ1: 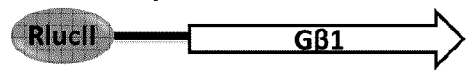
FIG. 2A
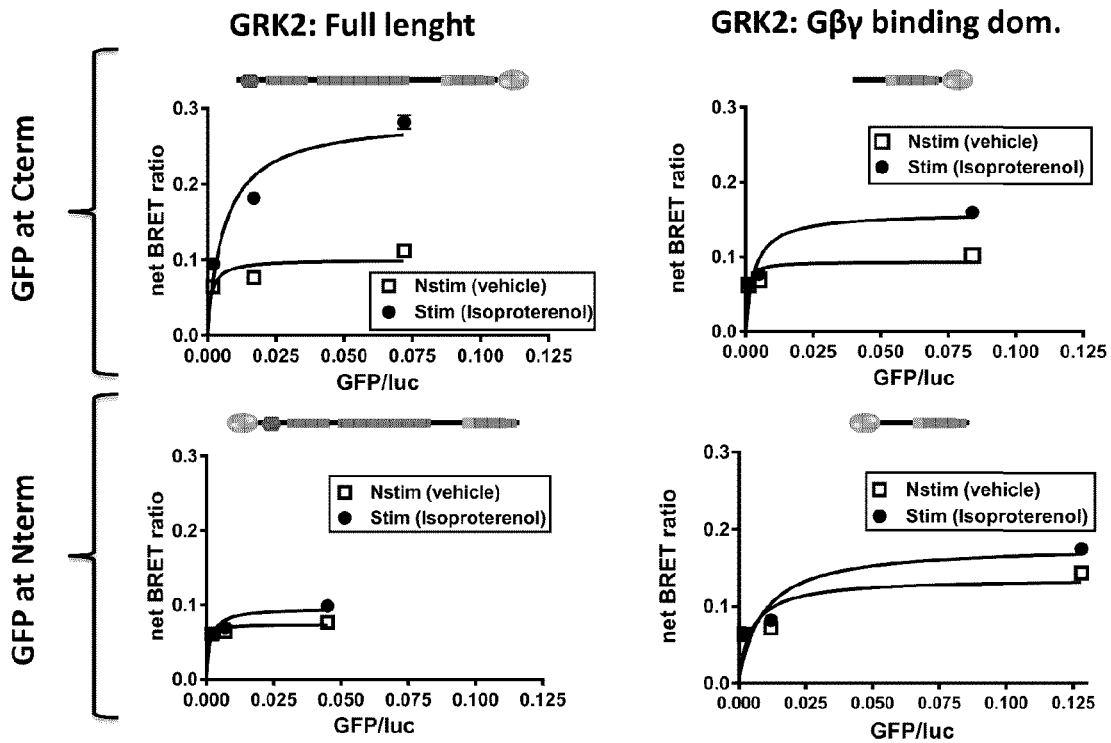
FIG. 2B

Legend: D = RET donor   A = RET acceptor   IRES = Internal Ribosome Entry Site

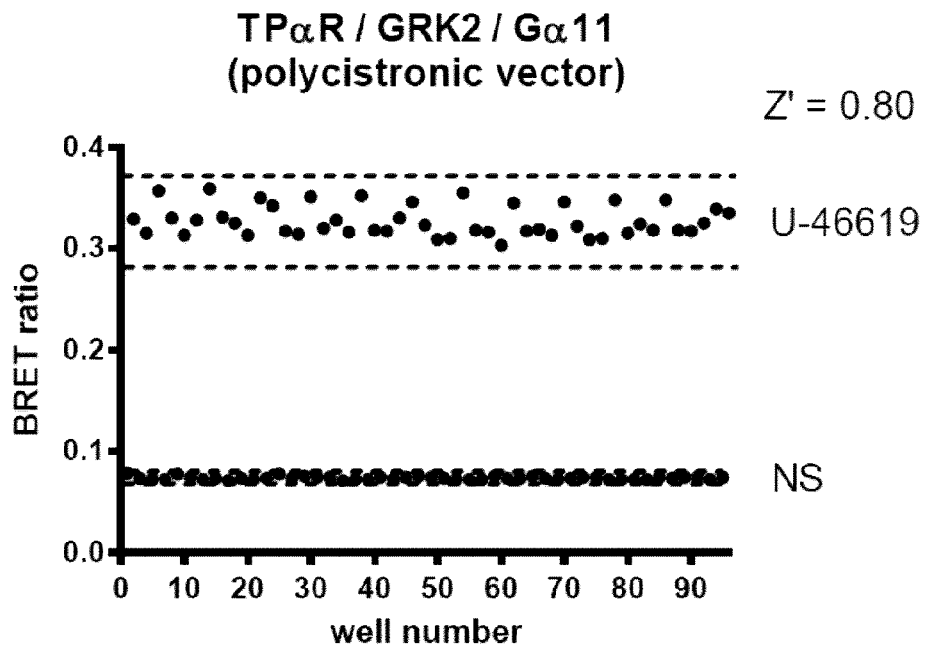
FIG. 11D
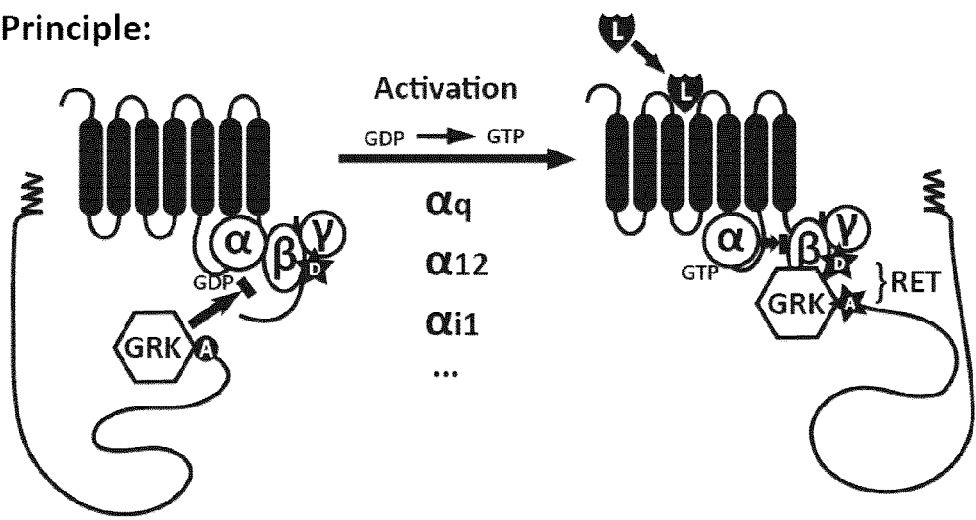
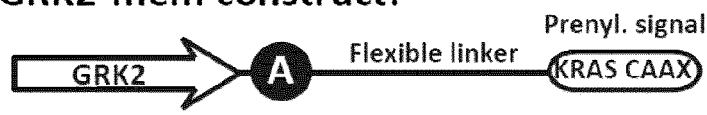
FIG. 12A

|             |     |                                                                    | SEQ ID NC |
|-------------|-----|--------------------------------------------------------------------|-----------|
| hGαq        | 40  | ...KLLLLGTGESGKSTF KQM IIHGSGYS E K GF TK- VY Q IFTA QAM RAM...    | 1         |
| hGα11       | 40  | ... KLLLLG TGESGKSTF KQM IIHGAGYSEE K GFTK- VY QN IFTA QAM RAM...  | 2         |
| hGα14       | 36  | ... KLLLLG TGESGKSTF KQM IIHGSGYS E DRKGF TK- VY QN IFTA QAM RAM...| 3         |
| hGα16       | 43  | ... KLLLLGPGESGKSTF KQM IIHGAGYSEEERKGF P- VY QN IF V S RAM EAM... | 4         |
| hGαoA       | 34  | ...VKLLLLGAGESGKSTIVKQMKIIH EDG SGE VKQ KP-VVYSNTIQS AAIVRAM...    | 5         |
| hGαoB       | 34  | ...VKLLLLGAGESGKSTIVKQMKIIH EDG SGE VKQ KP-VVYSNTIQS AAIVRAM...    | 6         |
| hGαT1rod    | 30  | ...VKLLLLGAGESGKSTIVKQMKIIHQDGYSLEECLEF IA- YGNT QSI AIVRAM...     | 7         |
| hGαT2cone   | 34  | ...VKLLLLGAGESGKSTIVKQMKIIHQDGYSPEECLEFKA- YGN V QSI AI RAM...     | 8         |
| hGαT3gust   | 34  | ...VKLLLLGAGESGKSTIVKQMKIIHKNGYSEQECMEFKA-V YSNT QSI AIV AM...     | 9         |
| hGαi1       | 34  | ...VKLLLLGAGESGKSTIVKQMKIIHEAGYSEEECK Q KA-VVYSNTIQSI AI RAM...    | 10        |
| hGαi2       | 34  | ...VKLLLLGAGESGKSTIVKQMKIIH EDGYSEEEC QY A-VVYSNTIQS MAIV AM...    | 11        |
| hGαi3       | 34  | ...VKLLLLGAGESGKSTIVKQMKIIHEDGYSE ECKQ KV-VVYSNTIQSI AI RAM...     | 12        |
| hGαz        | 34  | ... KLLLLGTSNSGKSTIVKQMKIIH SGG NLEACKE KP- IYNA DS TRI RA ...     | 13        |
| hGα12       | 58  | ...VK LLLLGAGESGKSTF KQM IIHGRE DQKALLEF D-T DNI KGSRV VDAR...     | 14        |
| hGα13       | 49  | ...VK LLLLGAGESGKSTF KQM IIHGQD DQRAREEF P-T YSNV IKG RV VDAR...   | 15        |
| hGαs        | 41  | ...H LLLLGAGESGKSTIVKQM I HVNG NG SEKATKVQD KNN LKEA ET IVAAM...   | 16        |
| hGαolf      | 120 | ...H LLLLGAGESGKSTIVKQM I HVNG NPEEKKQKIL-D RKNVKDAI TIVSAM...     | 17        |

α1              Linker1           αA

FIG. 14

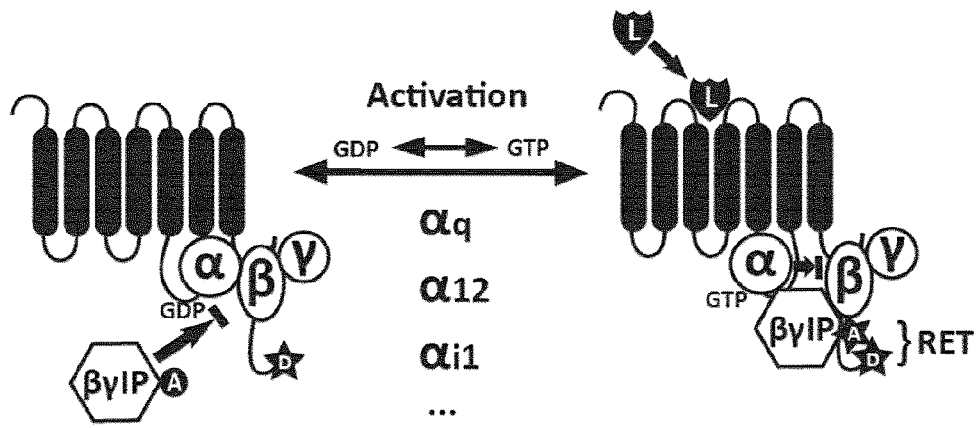

Legend: D=RET donor   A=RET acceptor   ⭐=Excited RET acceptor   L = GPCR ligand

FIG. 15A

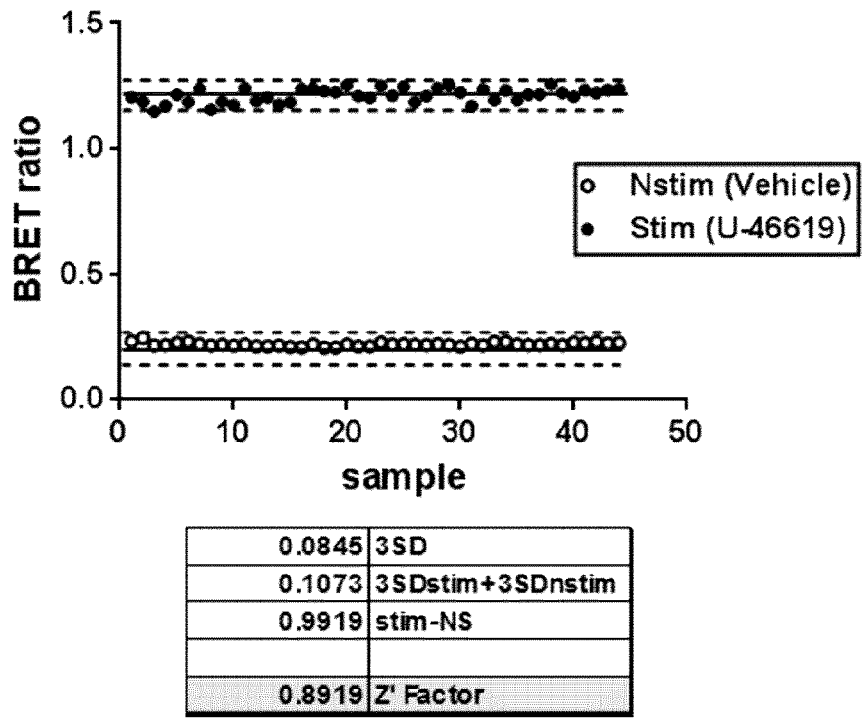

FIG. 16C

GRK2
MADLEAVLAD VSYLMAMEKS KATPAARASK KILLPEPSIR SVMQKYLEDR GEVTFEKIFS QKLGYLLFRD
FCLNHLEEAR PLVEFYEEIK KYEKLETEEE RVARSREIFD SYIMKELLAC SHPFSKSATE HVQGHLGKKQ
VPPDLFQPYI EEICQNLRGD VFQKFIESDK FTRFCQWKNV ELNIHLTMND FSVHRIIGRG GFGEVYGCRK
ADTGKMYAMK CLDKKRIKMK QGETLALNER IMLSLVSTGD CPFIVCMSYA FHTPDKLSFI LDLMNGGDLH
YHLSQHGVFS EADMRFYAAE IILGLEHMHN RFVVYRDLKP ANILLDEHGH VRISDLGLAC DFSKKKPHAS
VGTHGYMAPE VLQKGVAYDS SADWFSLGCM LFKLLRGHSP FRQHKTKDKH EIDRMTLTMA VELPDSFSPE
LRSLLEGLLQ RDVNRRLGCL GRGAQEVKES PFFRSLDWQM VFLQKYPPPL IPPRGEVNAA DAFDIGSFDE
EDTKG*IKLLD SDQELYRNFP LTISERWQQE VAETVFDTIN AETDRLEARK KAKNKQLGHE EDYALGKDCI*
*MHGYMSKMGN PFLTQWQRRY FYLFPNRLEW RGEGEAPQSL LTMEEIQSVE ETQIKERKCL LLKIRGGKQF*
*ILQCDSDPEL VQWKKELRDA YREAQQLVQR VPKMKNKPRS PVVELSKVPL VQRGSANGL*

FIG. 17A

GRK3
MADLEAVLAD VSYLMAMEKS KATPAARASK KIVLPEPSIR SVMQKYLEER HEITFDKIFN QRIGFLLFKD
FCLNEINEAV PQVKFYEEIK EYEKLENEED RLCRSRQIYD TYIMKELLSC SHPFSKQAVE HVQSHLSKKQ
VTSTLFQPYI EEICESLRGS IFQKFMESDK FTRFCQWKNV ELNIHLTMND FSVHRIIGRG GFGEVYGCRK
ADTGKMYAMK CLDKKRIKMK QGETLALNER IMLSLVSTGD CPFIVCMTYA FHTPDKLCFI LDLMNGGDLH
YHLSQHGVFS EKEMRFYATE IILGLEHMHN RFVVYRDLKP ANILLDEHGH VRISDLGLAC DFSKKKPHAS
VGTHGYMAPE VLQKGTAYDS SADWFSLGCM LFKLLRGHSP FRQHKTKDKH EIDRMTLTMN VELPDVFSPE
LKSLLEGLLQ RDVSKRLGCH GGSAQELKTH DFFRGIDWQH VYLQKYPPPL IPPRGEVNAA DAFDIGSFDE
EDTKG*IKLLD CDQELYKNFP LVISERWQQE VAETVYEAVN ADTDKIEARK RAKNKQLGHE EDYALGRDCI*
*VHGYMLKLGN PFLTQWQRRY FYLFPNRLEW RGEGESRQSL LTMEQIVSVE ETQIKDKKCI LLRIKGGKQF*
*VLQCESDPEF VQWKKELTET FMEAQRLLRR APKFLNKSRS AVVELSKPPL CHRNSNGL*

FIG. 17B

PLEKHG2
MPEGAQGLSL SKPSPSLGCG RRGEVCDCGT VCETRTAPAA PTMASPRGSG SSTSLSTVGS EGDPAPGPTP
ACSASRPEPL PGPPIRLHLS PVGIPGSARP SRLERVAREI VETERAYVRD LRSIVEDYLG PLLDGGVLGL
SVEQVGTLFA NIEDIYEFSS ELLEDLENSS SAGGIAECFV QRSEDFDIYT LYCMNYPSSL ALLRELSLSP
PAALWLQERQ AQLRHSLPLQ SFLLKPVQRI LKYHLLLQEL GKHWAEGPGT GGREMVEEAI VSMTAVAWYI
NDMKRKQEHA ARLQEVQRRL GGWTGPELSA FGELVLEGAF RGGGGGGPRL RGGERLLFLF SRMLLVAKRR
GLEYTYKGHI FCCNLSVSES PRDPLGFKVS DLTIPKHRHL LQAKNQEEKR LWIHCLQRLF FENHPASIPA
KAKQVLLENS LHCAPKSKPV LEPLTPPLGS PRPRDARSFT PGRRNTAPSP GPSVIRRGRR QSEPVKDPYV
MFPQNAKPGF KHAGSEGELY PPESQPPVSG SAPPEDLEDA GPPTLDPSGT SITEEILELL NQRGLRDPGP
STHDIPKFPG DSQVPGDSET LTFQALPSRD SSEEEEEEEE GLEMDERGPS PLHVLEGLES SIAAEMPSIP
CLTKIPDVPN LPEIPSRCEI PEGSRLPSLS DISDVFEMPC LPAIPSVPNT PSLSSTPTLS CDSWLQGPLQ
EPAEAPATRR ELFSGSNPGK LGEPPSGGKA GPEEDEEGVS FTDFQPQDVT QHQGFPDELA FRSCSEIRSA
WQALEQGQLA RPGFPEPLLI LEDSDLGGDS GSGKAGAPSS ERTASRVREL ARLYSERIQQ MQRAETRASA
NAPRRRPRVL AQPQPSPCLP QEQAEPGLLP AFGHVLVCEL AFPLTCAQES VPLGPAVWVQ AAIPLSKQGG
SPDGQGLHVS NLPKQDLPGI HVSAATLLPE QGGSRHVQAP AATPLPKQEG PLHLQVPALT TFSDQGHPEI
QVPATTPLPE HRSHMVIPAP STAFCPEQGH CADIHVPTTP ALPKEICSDF TVSVTTPVPK QEGHLDSESP
TNIPLTKQGG SRDVQGPDPV CSQPIQPLSW HGSSLDPQGP GDTLPPLPCH LPDLQIPGTS PLPAHGSHLD
HRIPANAPLS LSQELPDTQV PATTPLPLPQ VLTDIWVQAL PTSPKQGSLP DIQGPAAAPP LPEPSLTDTQ
VQKLTPSLEQ KSLIDAHVPA ATPLPERGGS LDIQGLSPTP VQTTMVLSKP GGSLASHVAR LESSDLTPPH
SPPPSSRQLL GPNAAALSRY LAASYISQSL ARRQGPGGGA PAASRGSWSS APTSRASSPP PQPQPPPPPA
RRLSYATTVN IHVGGGGRLR PAKAQVRLNH PALLASTQES MGLHRAQGAP DAPFHM

FIG. 17C

MVSKGEELFTGVVPILVELDGDVNGHKFSVSGEGEGDATYGKLTLKFICTTGKLPVPWPTLVTTLSYGVQCFSRYPDHMK
QHDFFKSAMPEGYVQERTIFFKDDGNYKTRAEVKFEGDTLVNRIELKGIDFKEDGNILGHKLEYNYNPHNVYIMADKQKN
GIKVNFKIRHNIEDGSVQLADHYQQNTPIGDGPVLLPDNHYLFTQSALSKDPNEKRDHMVLLEFVTAAGITLGMDELYK

FIG. 17D

MDLAKLGLKEVMPTKINLEGLVGDHAFSMEGVGEGNILEGTQEVKISVTKGAPLPFAFDIVSVAFSYGNRAYTGYPEEIS
DYFLQSFPEGFTYERNIRYQDGGTAIVKSDISLEDGKFIVNVDFKAKDLRRMGPVMQQDIVGMQPSYESMYTNVTSVIGE
CIIAFKLQTGKHFTYHMRTVYKSKKPVETMPLYHFIQHRLVKTNVDTASGYVVQHETAIAAHSTIKKIEGSLP

FIG. 17E

MTSKVYDPEQRKRMITGPQWWARCKQMNVLDSFINYYDSEKHAENAVIFLHGNATSSYLWRHVVPHIEPVARCIIPDLIG
MGKSGKSGNGSYRLLDHYKYLTAWFELLNLPKKIIFVGHDWGAALAFHYSYEHQDKIKAIVHAESVVDVIESWDEWPDIE
EDIALIKSEEGEKMVLENNFFVETVLPSKIMRKLEPEEFAAYLEPFKEKGEVRRPTLSWPREIPLVKGGKPDVVQIVRNY
NAYLRASDDLPKMFIESDPGFFSNAIVEGAKKFPNTEFVKVKGLHFSQEDAPDEMGKYIKSFVERVLKNEQ

FIG. 17F

BIOSENSOR BASED ON Gβγ-INTERACTING PROTEINS TO MONITOR G-PROTEIN ACTIVATION

CROSS REFERENCE TO RELATED APPLICATIONS

This application claims the benefit of U.S. provisional application Ser. No. 62/063,622, filed on Oct. 14, 2014, which is incorporated herein by reference in its entirety.

TECHNICAL FIELD

The present disclosure relates to the monitoring of G-protein activation, and more specifically to a signaling biosensor for detecting G-protein activation.

BACKGROUND ART

Hetero-trimeric G-proteins consisting of three subunits α, β and γ, relays the information provided by G-protein-coupled receptors (GPCRs) to various intracellular effectors. In the absence of stimulation, the α-subunit of the G-protein is in complex with a GDP (guanosine diphosphate) molecule. The conformational change that follows receptor activation by a ligand, promotes the phosphorylation of the GDP molecule into a GTP (guanosine triphosphate). The GTP-bound Gα subunit dissociates from the Gβγ subunits, both of which are then available to interact with downstream effectors and modulate their activity. G-protein activation can thus be assessed by analyzing those downstream effectors through their interaction with Gβγ, using Gβγ interacting proteins (βγIP). Following GTP hydrolysis to GDP by the Gα subunit, the Gα affinity for Gβγ is restored and the three subunits re-associate to form an inactive hetero-trimeric G-protein, ending the engagement of effectors and thus signal transduction (Gilman 1987).

In addition to the classical activation of G-proteins by GPCRs, other proteins can also modulate the activity of these hetero-trimeric G-proteins, such as regulators of G-protein signaling (RGS), activators of G-protein signaling (AGS), and resistance to inhibitors of cholinesterase 8 proteins (Ric-8). In some of these non-canonical signaling pathways, the guanine exchange factor (GEF) activity classically exerted by GPCRs is replaced by another protein such as Ric-8 for example (Boularan and Kehrl, 2014).

G-protein-coupled receptor kinases (GRKs) 2 and 3, which were first characterized for their role in desensitization of receptors, are also effectors engaged through their interaction with Gβγ subunits. GRK2 and GRK3 contain a pleckstrin homology (PH) domain that interacts with the Gβγ subunits of G-proteins, upon their dissociation from the activated GTP-bound Gα subunit (Pitcher, Inglese et al. 1992) (Touhara, Inglese et al. 1994). As a consequence, proteins interacting with Gβγ (βγIP) such as GRK2 and GRK3, can be used to directly study G-protein activation by GPCRs or other G-protein activators.

Several approaches are currently used in the drug discovery industry to assess the activation of GPCRs and thus the engagement of G-proteins by receptors, such as calcium mobilization assay or radioactive assay based on GTPγS incorporation by G-proteins. The calcium mobilization assay measures a signaling event occurring downstream Gq activation and can be applied to Gi or Gs-coupled receptors only when coupled with the use of modified Gα subunits. In the case of GTPγS incorporation assay, the activation of the various hetero-trimeric G-proteins is directly measured on cell membranes using radioactive GTPγ$^{35}$S, and cannot be performed in living cells.

The activation of G-proteins in living cells, without modifying the G-protein activator or the Gα subunit, has thus not been explored so far. Furthermore, the known methods are not suitable to study all the different G-proteins using the same detection partners. Such assays would be particularly useful in the different stages of the drug discovery process, by enabling characterization of G-protein coupling profile and facilitating the identification of new compounds with defined signaling properties for use in screening assays and structure-activity relationship studies, for example. This is particularly true given the importance of G-protein activators as drug targets, with 26% of all prescribed medications acting through GPCRs (Garland 2013). Even though several approaches are available to support the development of new therapeutically active molecules targeting G-protein activators, the discovery of novel drugs is often limited by the dearth of information available on the precise mechanism of action of those compounds.

There is thus a need for novel tools and assays to assess activation of G-proteins.

The present description refers to a number of documents, the content of which is herein incorporated by reference in their entirety.

SUMMARY OF THE INVENTION

The present invention provides the following items 1 to 68:

1. A biosensor system for detecting G-protein activity, said biosensor system comprising the elements defined in (A) or (B):

(A)
    (i) a first biosensor comprising:
        a first component comprising a Gβγ interacting protein (βγIP) fused to (a) a resonance energy transfer (RET) donor; (b) a RET acceptor or (c) a first fragment of a reporter protein; and
        a second component comprising a fused Gβ protein or a fused Gγ protein, wherein said Gβ protein or said Gγ protein is fused to (a) a RET donor; (b) a RET acceptor or (c) a second fragment of said reporter protein;
    (ii) a second biosensor comprising:
        the first and second components defined in (i); and
        a third component comprising a recombinant Gα protein;
    wherein (a) if said βγIP is fused to said RET donor, said Gβ or Gγ protein is fused to said RET acceptor; (b) if said βγIP is fused to said RET acceptor, said Gβ or Gγ protein is fused to said RET donor; and (c) if said βγIP is fused to said first fragment of said reporter protein, said Gβ or Gγ protein is fused to said second fragment of said reporter protein; or (B)
    (i) a biosensor comprising
        a first component comprising a Gβγ interacting protein (βγIP) fused to (a) a RET donor; (b) a RET acceptor or (c) a first fragment of a reporter protein;
        a second component comprising a fused G-protein coupled receptor (GPCR), wherein said GPCR is fused at its C-terminal to (a) a RET donor; (b) a RET acceptor or (c) a second fragment of said reporter protein;

a third component comprising a recombinant Gα protein;

wherein (a) if said βγIP is fused to said RET donor, said GPCR is fused to said RET acceptor; (b) if said βγIP is fused to said RET acceptor, said GPCR is fused to said RET donor; and (c) if said βγIP is fused to said first fragment of said reporter protein, said GPCR is fused to said second fragment of said reporter protein.

2. The biosensor system of item 1, wherein said Gγ protein is fused to said RET donor, RET acceptor or second fragment.

3. The biosensor system of item 1 or 2, wherein said RET donor, RET acceptor or second fragment is fused at the N-terminus of said Gβ or Gγ protein.

4. The biosensor system of any one of items 1 to 3, wherein said RET donor, RET acceptor or first fragment is fused at the C-terminus of said βγIP.

5. The biosensor system of any one of items 1 to 4, wherein said βγIP is fused to said RET acceptor and said Gβ protein, Gγ protein or GPCR is fused to said RET donor.

6. The biosensor system of any one of items 1 to 5, wherein said RET donor is a bioluminescent protein.

7. The biosensor system of item 6, wherein said bioluminescent protein is a luciferase.

8. The biosensor system of item 7, wherein said luciferase is a *Renilla* luciferase.

9. The biosensor system of any one of items 1 to 8, wherein said RET acceptor is a fluorescent protein.

10. The biosensor system of item 9, wherein said fluorescent protein is a GFP.

11. The biosensor system of any one of items 1 to 4, wherein said βγIP is fused to said first fragment, and said Gβ protein, Gγ protein or GPCR is fused to said second fragment.

12. The biosensor system of item 11, wherein said reporter protein is a bioluminescent protein.

13. The biosensor system of item 12, wherein said bioluminescent protein is a luciferase.

14. The biosensor system of item 13, wherein said luciferase is a *Renilla* luciferase.

15. The biosensor system of item 14, wherein said first fragment comprises about residues 1 to 110 of *Renilla* luciferase, and said second fragment comprises about residues 111 to 311 of *Renilla* luciferase.

16. The biosensor system of any one of items 1 to 15, wherein the first component further comprises a plasma membrane (PM)-targeting moiety fused to said βγIP or said RET donor, RET acceptor or first fragment.

17. The biosensor system of item 16, wherein said PM-targeting moiety is fused at the C-terminus of said RET donor, RET acceptor or first fragment.

18. The biosensor system of item 16 or 17, wherein said PM-targeting moiety comprises a prenylation motif.

19. The biosensor system of item 16, wherein said prenylation motif is the prenylation motif of human KRAS splice variant b.

20. The biosensor system of item 19, wherein said PM-targeting moiety comprises the amino acid sequence KKKKKKSKTKCVIM (SEQ ID NO:37).

21. The biosensor system of any one of items 16 to 20, further comprising a flexible linker between (i) said RET donor, RET acceptor or first fragment and (ii) said PM-targeting moiety.

22. The biosensor system of item 21, wherein said flexible linker has a length corresponding to about 50 to about 500 amino acids.

23. The biosensor system of item 22, wherein said flexible linker has a length corresponding to about 200 amino acids.

24. The biosensor system of any one of items 1 to 23, wherein said recombinant Gα protein is human $G\alpha_q$, $G\alpha_s$, $G\alpha_{i1}$, $G\alpha_{i2}$, $G\alpha_{i3}$, $G\alpha_{t-cone}$, $G\alpha_{t-rod}$, $G\alpha_{t-gust}$, $G\alpha_z$, $G\alpha_{oA}$, $G\alpha_{oB}$, $G\alpha_{olf}$, $G\alpha_{11}$, $G\alpha_{12}$, $G\alpha_{13}$, $G\alpha_{14}$, and $G\alpha_{15}/G\alpha_{16}$ protein, or a promiscuous or non-selective Gα variant thereof, for example a mutated Gα polypeptide comprising a mutation at a position corresponding to residue 66, 67 and/or 75 of human $G\alpha_q$ protein as described herein.

25. The biosensor system of any one of items 1 to 24, wherein said βγIP is GRK2 or GRK3.

26. The biosensor system of any one of items 1 to 25, wherein (i) if said second component comprises a fused Gβ protein, said first and second biosensors further comprises a recombinant Gγ protein, or (ii) if said second component comprises a fused Gγ protein, said first and second biosensors further comprises a recombinant Gβ protein.

27. The biosensor system of any one of items 1 to 25, wherein the biosensor system defined in (A) further comprises a G-protein-coupled receptor (GPCR).

28. The biosensor system of any one of items 1 to 27, wherein the biosensor system defined in (B) further comprises a recombinant Gβ protein and/or a recombinant Gγ protein.

29. The biosensor system of any one of items 1 to 28, wherein said first biosensor is present in a first cell and said second biosensor is present in a second cell.

30. The biosensor system of any one of items 1 to 28, wherein in the biosensor system defined in (A), said first biosensor is present in a first membrane preparation and said second biosensor is present in a second membrane preparation.

31. The biosensor system of any one of items 1 to 30, wherein the biosensor system defined in (A) comprises a plurality of second biosensors, wherein each of said second biosensors comprises a different recombinant Gα protein.

32. The biosensor system of item 31, wherein said different recombinant Gα proteins are at least two of the following Gα proteins: $G\alpha_q$, $G\alpha_s$, $G\alpha_{i1}$, $G\alpha_{i2}$, $G\alpha_{i3}$, $G\alpha_{t-cone}$, $G\alpha_{t-rod}$, $G\alpha_{t-gust}$, $G\alpha_z$, $G\alpha_{oA}$, $G\alpha_{oB}$, $G\alpha_{olf}$, $G\alpha_{11}$, $G\alpha_{12}$, $G\alpha_{13}$, $G\alpha_{14}$, and $G\alpha_{15}/G\alpha_{16}$.

33. A nucleic acid comprising a sequence encoding the first, second and third components defined in any one of items 1 to 26.

34. The nucleic acid of item 33, further comprising a sequence encoding a Gγ protein or a Gβ protein.

35. The nucleic acid of item 33 or 34, further comprising one or more translation regulatory sequences.

36. The nucleic acid of item 35, wherein said one or more translation regulatory sequences are Internal Ribosome Entry Site (IRES).

37. A biosensor for detecting G-protein activity comprising:
(i) a first component comprising a Gβγ interacting protein (βγIP) fused to (a) a RET donor; (b) a RET acceptor or (c) a first fragment of a reporter protein; and
(ii) a second component comprising a fused plasma membrane (PM)-targeting moiety, wherein said PM-targeting moiety is fused to (a) a RET donor; (b) a RET acceptor or (c) a second fragment of said reporter protein;

wherein (a) if said βγIP is fused to said RET donor, said PM-targeting moiety is fused to said RET acceptor; (b) if said βγIP is fused to said RET acceptor, said PM-targeting moiety is fused to said RET donor; and (c) if said βγIP is fused to said first fragment of said reporter protein, said PM-targeting moiety is fused to said second fragment of said reporter protein.
38. The biosensor of item 37, wherein said PM targeting moiety is a PM protein or a fragment thereof that localizes to the PM.
39. The biosensor of item 38, wherein said PM protein or fragment thereof comprises (a) a palmitoylation, myristoylation, and/or prenylation signal sequence and/or (b) a polybasic sequence.
40. The biosensor of item 39, wherein said polybasic sequence and prenylation signal sequence are from human KRAS splice variant b.
41. The biosensor of item 40, wherein said PM targeting moiety comprises the amino acid sequence KKKKKK-SKTKCVIM (SEQ ID NO:37).
42. The biosensor of any one of items 37 to 41, wherein said biosensor further comprises a third component that comprises a recombinant Gα protein.
43. The biosensor of item 42, wherein said recombinant Gα protein is of the Gq family.
44. The biosensor of item 43, wherein said recombinant Gα protein is Gα$_q$ or Gα$_{11}$.
45. A method for determining whether a test agent modulates the activity of a GPCR, said method comprising:
  (1) providing a biosensor comprising the elements defined in (A), (B) or (C):
    (A)
      (i) a first component comprising a Gβγ interacting protein (βγIP) fused to (a) a RET donor; (b) a RET acceptor or (c) a first fragment of a reporter protein;
      (ii) a second component comprising a fused Gβ protein or a fused Gγ protein, wherein said Gβ protein or said Gγ protein is fused to (a) a RET donor; (b) a RET acceptor or (c) a second fragment of said reporter protein,
      wherein (a) if said βγIP is fused to said RET donor, said Gβ or Gγ protein is fused to said RET acceptor; (b) if said βγIP is fused to said RET acceptor, said Gβ or Gγ protein is fused to said RET donor; and (c) if said βγIP is fused to said first fragment of said reporter protein, said Gβ or Gγ protein is fused to said second fragment of said reporter protein;
      (iii) a third component comprising a recombinant Gα protein; and
      (iv) a fourth component comprising said GPCR;
    (B)
      (i) a first component comprising a Gβγ interacting protein (βγIP) fused to (a) a RET donor; (b) a RET acceptor or (c) a first fragment of a reporter protein;
      (ii) a second component comprising said GPCR fused at its C-terminal to (a) a RET donor; (b) a RET acceptor or (c) a second fragment of said reporter protein;
      (iii) a third component comprising a recombinant Gα protein;
      wherein (a) if said βγIP is fused to said RET donor, said GPCR is fused to said RET acceptor; (b) if said βγIP is fused to said RET acceptor, said GPCR is fused to said RET donor; and (c) if said βγIP is fused to said first fragment of said reporter protein, said GPCR is fused to said second fragment of said reporter protein; or
    (C)
      (i) a first component comprising a Gβγ interacting protein (βγIP) fused to (a) a RET donor; (b) a RET acceptor or (c) a first fragment of a reporter protein;
      (ii) a second component comprising a fused plasma membrane (PM)-targeting moiety, wherein said PM-targeting moiety is fused to (a) a RET donor; (b) a RET acceptor or (c) a second fragment of said reporter protein;
      wherein (a) if said βγIP is fused to said RET donor, said PM-targeting moiety is fused to said RET acceptor; (b) if said βγIP is fused to said RET acceptor, said PM-targeting moiety is fused to said RET donor; and (c) if said βγIP is fused to said first fragment of said reporter protein, said PM-targeting moiety is fused to said second fragment of said reporter protein;
      (iii) a third component comprising a recombinant Gα protein; and
      (iv) a fourth component comprising said GPCR; and
  (2) measuring the signal emitted by said RET acceptor or reporter protein in the presence and absence of said test agent;
wherein a higher signal measured in the presence of the agent is indicative that said test agent increases the activity of said GPCR, and a lower signal measured in the presence of the agent is indicative that said agent inhibits the activity of said GPCR.
46. The method of item 44, wherein said biosensors comprise one or more of the features defined in items 2 to 32 and 38 to 44.
47. A method for determining whether a Gα protein is activated by a GPCR agonist, said method comprising:
  (a) measuring the signal emitted by said RET acceptor or reporter protein in the presence and absence of said GPCR agonist in the first and second biosensors of the biosensor system of any one of items 1 to 32, and
  (b) identifying whether the Gα protein is activated by said GPCR agonist based on the signal emitted by said RET acceptor or reporter protein;
  wherein a higher increase of the signal measured in the presence of the GPCR agonist in said second biosensor relative to said first biosensor is indicative that the Gα protein is activated by said GPCR agonist, and wherein a similar or lower increase, or a decrease, of the signal measured in the presence of the GPCR agonist in said second biosensor relative to said first biosensor is indicative that said the Gα protein is not activated by said GPCR agonist.
48. A method for determining whether a Gα protein is activated by a GPCR agonist, said method comprising:
  (a) measuring the signal emitted by a RET acceptor or reporter protein in the presence and absence of said GPCR agonist in a first biosensor comprising:
    (i) a first component comprising a Gβγ interacting protein (βγIP) fused to (a) a RET donor; (b) a RET acceptor or (c) a first fragment of a reporter protein; and
    (ii) a second component comprising a fused G-protein coupled receptor (GPCR), wherein said GPCR is fused at its C-terminal to (a) a RET donor; (b) a RET acceptor or (c) a second fragment of said reporter protein;
  (b) measuring the signal emitted by a RET acceptor or reporter protein in the presence and absence of said GPCR agonist in a second biosensor comprising:

(i) the first and second components defined in (a); and
(ii) a third component comprising a recombinant form of said Gα protein;
wherein (a) if said βγIP is fused to said RET donor, said GPCR is fused to said RET acceptor; (b) if said βγIP is fused to said RET acceptor, said GPCR is fused to said RET donor; and (c) if said βγIP is fused to said first fragment of said reporter protein, said GPCR is fused to said second fragment of said reporter protein;
wherein a higher increase of the signal measured in the presence of the GPCR agonist in said second biosensor relative to said first biosensor is indicative that the Gα protein is activated by said GPCR agonist, and wherein a similar or lower increase, or a decrease, of the signal measured in the presence of the GPCR agonist in said second biosensor relative to said first biosensor is indicative that said the Gα protein is not activated by said GPCR agonist.

49. The method of item 47, wherein said biosensors comprise one or more of the features defined in items 38 to 44.

50. The method of item 45, further comprising
   (3) measuring the signal emitted by said RET acceptor or reporter protein in
       (a) the second biosensor(s) defined in element (A) of any one of items 1 to 31,
       (b) the biosensor defined in element (B) of any one of items 1 to 31, or
       (c) the biosensor of any one of items 42 to 44,
       in the presence and absence of a test agent and in the presence of a GPCR agonist, wherein said recombinant Gα protein is coupled to said GPCR; and
   (4) determining whether said test agent is an inhibitor of said Gα protein;
wherein a lower signal measured in the presence of the test agent is indicative that said test agent is an inhibitor of said Gα protein, and a similar or higher signal measured in the presence of the test agent is indicative that said test agent is not an inhibitor of said Gα protein.

51. A method for determining whether a test agent is an inhibitor of a Gα protein of interest, said method comprising:
   (1) contacting
       (a) the second biosensor(s) defined in element (A) of any one of items 1 to 32,
       (b) the biosensor defined in element (B) of any one of items 1 to 32, or
       (c) the biosensor of any one of items 42 to 44;
       with a GPCR agonist, wherein said recombinant Gα protein corresponds to said Gα protein of interest;
   (2) measuring the signal emitted by said RET acceptor or reporter protein in the presence and absence of said test agent; and
   (c) determining whether said test agent is an inhibitor of said Gα protein,
wherein a lower signal measured in the presence of the test agent is indicative that said test agent is an inhibitor of said Gα protein of interest, and a similar or higher signal measured in the presence of the test agent is indicative that said test agent is not an inhibitor of said Gα protein of interest.

52. A method for determining whether a test agent is an activator of a Gα protein of interest, said method comprising:
   (1) contacting
       (a) the second biosensor(s) defined in element (A) of any one of items 1 to 32,
       (b) the biosensor defined in element (B) of any one of items 1 to 32, or
       (c) the biosensor of any one of items 42 to 44;
       with a GPCR antagonist, wherein said recombinant Gα protein corresponds to said Gα protein of interest;
   (2) measuring the signal emitted by said RET acceptor or reporter protein in the presence and absence of said test agent; and
   (3) determining whether said test agent is an activator of said Gα protein,
wherein a higher signal measured in the presence of the test agent is indicative that said test agent is an activator of said Gα protein of interest, and a similar or lower signal measured in the presence of the test agent is indicative that said test agent is not an activator of said Gα protein of interest.

53. The method of any one of items 45 to 52, wherein said RET donor is a bioluminescent protein, and wherein said method further comprises contacting the biosensor with a substrate for said donor bioluminescent protein.

54. The method of item 53, wherein said substrate is a luciferin.

55. The method of item 54, wherein said luciferin is a coelenterazine.

56. The method of item 55, wherein said coelenterazine is Coelenterazine 400A.

57. The method of any one of items 45 to 56, wherein the biosensor comprises a RET donor and a RET acceptor, and wherein said method further comprises: (i) measuring signal emitted by said RET donor, and (ii) determining the ratio [RET acceptor signal/RET donor signal].

58. A mutated Gα polypeptide comprising a mutation at a position corresponding to residue 67 and/or residue 75 of human $G\alpha_q$ protein.

59. The mutated Gα polypeptide of item 58, wherein said mutation is a substitution.

60. The mutated Gα polypeptide of item 58 or 59, wherein said mutation is at a position corresponding to residue 67 of human $G\alpha_q$ protein.

61. The mutated Gα polypeptide of item 60, wherein said mutation is a substitution for a non-aromatic residue.

62. The mutated Gα polypeptide of item 61, wherein non-aromatic residue is cysteine.

63. The mutated Gα polypeptide of item 58 or 59, wherein said mutation is at a position corresponding to residue 75 of human $G\alpha_q$ protein.

64. The mutated Gα polypeptide of item 63, wherein said mutation is a substitution for a non-aromatic residue.

65. The mutated Gα polypeptide of item 64, wherein said non-aromatic residue is glycine.

66. A nucleic acid comprising a sequence encoding the mutated Gα polypeptide of any one of items 58 to 65.

67. A plasmid or vector comprising the nucleic acid of item 66.

68. A cell comprising the nucleic acid of item 65 or the plasmid of item 67.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:
FIG. 1C shows theoretical scenarios and corresponding interpretation of results for the βγIP-based biosensor of G-protein activation. Three different scenarios are depicted in FIG. 1C using BRET as an example of detection method. In scenario 1 (left) the cells are transfected with all components of the biosensor except for the Gα subunit of the heterotrimeric G-protein. The lack of α subunits causes the excess Gβγ subunits to interact with the βγIP at basal state. In scenario 2 (middle), all the components of the biosensor are transfected but the Gα subunit that is overexpressed (Gα$_1$) is not functionally coupled to the receptor of interest. Scenario 3 (right) shows a typical response of the biosensor when all its components are expressed along with the proper Gα subunit (Gα$_2$) for the receptor of interest. In this case, receptor activation leads to an increase in BRET signal which is caused by the recruitment of GFP-tagged βγIP to the RLuc-tagged Gβγ subunits previously coupled to the specific Gα subunit.

FIG. 2 presents some of the different constructs tested for optimization of the βγIP-based G-protein activation biosensor. In FIG. 2A, the structure of GRK2/3 is presented. GRK2/3 arbour different functional domains, a calmodulin binding domain (CAM), an RGS (Regulator of G protein Signaling) domain that can be inactivated by the D110A substitution described herein, a catalytic domain for its kinase activity and that can be inactivated by the K220R substitution described herein, and a Pleckstrin homology domain (PH domain) that binds to PIP$_2$ and Gβ subunits of heterotrimeric G-proteins. These interactions promote GRK translocation to the plasma-membrane and its activation. Phosphorylation of the C-terminal portion of GRK (serine 670 and 685) has been reported to modulate its activity. Four different GFP-tagged constructs for GRK2 and GRK3 were tested, two based on the complete GRK coding sequence and two on the C-terminal PH domain/Gβ binding domain, with GFP at either the N-terminal or the C-terminal portion of GRK. Both Gβ and Gγ subunits were tested as a fusion with a BRET tag and can be used to monitor GRK/Gβγ interaction.

FIGS. 2B and 2C show the testing of different ratios (titration) of the four different GRK constructs (FIG. 2A) and responses obtained for β$_1$AR activation of Gα$_{15}$ (FIG. 2B) and in for thromboxane A2 receptor (TPαR)-mediated activation of Gα$_{11}$ (FIG. 2C). Titrations of BRET donor to acceptor were performed on HEK293 cells transfected with constructs encoding a receptor and a Gα (β$_1$AR/Gα$_{15}$ in FIG. 2B & TPαR/Gα$_{11}$ in FIG. 2C), Gβ1, RlucII-Gγ5 (0.5 ng per well of a 96-well plate) and variable amount of GRK2 constructs tagged with GFP10 (up to 75 ng/well). The cells were treated with vehicle or agonist (1 μM isoproterenol and 100 nM U-46619 for cells expressing β$_1$AR and TPαR, respectively) for 15 min. The BRET ratios were reported in function of GFP-construct expression (evaluated in fluorescence) over RlucII construct expression (evaluated in bioluminescence). These results indicate that the full length GRK tagged at its C-terminal with the BRET donnor (GFP) is giving the best dynamic window in term of amplitude of BRET signal and stability of response over a wider range of ratios donnor to acceptor.

FIG. 3A: HEK293 cells transiently expressing the TPαR along with GRK2-GFP, Rluc-Gγ5, Gβ1 and the indicated Gα, were exposed to 100 nM of U-46619 or vehicle for 15 min, prior to BRET measurements. The mock condition is without any Gα subunit overexpression. FIG. 3B: BRET values obtained for the agonist treated cells in FIG. 3A expressed as a percentage of the BRET values obtained with the corresponding cells treated with vehicle. Mock condition is used to determine the threshold of a positive response. FIG. 3C: Dose-response curves using the agonist U-46619 for Gα$_q$, Gα$_{13}$, Gα$_{14}$, Gα$_{15}$, Gα$_q$G66K and Gα$_q$Y67C activation of the TPαR using GRK2-GFP/Rluc-Gγ5/Gβ1 biosensor.

FIGS. 4A, 4C and 4E: Data are expressed as a percentage of the BRET signal obtained in vehicle-treated cells. Mock condition without any Gα subunit overexpression, was used to determine the threshold of a positive response. As presented in FIGS. 4A, 4C and 4E, G-protein with promiscuous activation properties such as Gα$_q$Y67C could be used to monitor receptor activation (see position and surrounding sequence at FIG. 14). These promiscuous mutants of Gα, could be used as positive controls for receptor activation which, could be useful for characterizing antagonists or screening for orphan receptor agonists. FIG. 4B Dose-response curves for Rotigotine, a D$_2$R agonist, with selected Gα proteins (Gα$_{i1}$ and four promiscuous Gα$_q$ mutants: G66K, G66D, Y67C and F75G) using the GRK2-GFP/Rluc-Gγ5/Gβ1 biosensor. In FIG. 4D, dose-response curves are presented for phenylephrine, an α-adrenergic agonist, with α$_{1B}$AR and selected Gα proteins (Gα$_{11}$ and Gα$_q$) using the GRK2-GFP/Rluc-Gγ5/Gβ1 biosensor. In FIG. 4E, dose-response curves of Gα, activation were obtained for different adrenergic agonists: epinephine, norepinephrine, phenylephrine and isoproterenol, from HEK293 cells expressing α$_{2C}$AR, Gα$_z$, GRK2-GFP, Rluc-Gγ5 and Gβ1. FIG. 4F shows the G-protein activation profile for α$_{2C}$AR using two different α$_{2C}$AR agonists, epinephrine and phenylephrine. These results show that a βγIP-based biosensor can be used to establish G-protein activation and pharmacological profiles of different receptors and ligands. In FIG. 4G to 4J, dose-response curves for epinephrine/α$_{2C}$AR-promoted Gα$_z$ activation were obtained with different combinations of Gβγ subunits. HEK293 cells were transfected with constructs encoding the α$_{2C}$AR, Gα$_z$, GRK2-GFP, different Rluc-tagged Gγ (FIGS. 4G and 4H) and a Gβ (Gβ1 in FIG. 4G and the short variant of Gβ3 (Gβ3sh), in FIG. 4H). In FIGS. 4I and 4J, cells were transfected with constructs encoding the α$_{2C}$AR, Gα$_z$, GRK2-GFP, Rluc-tagged Gγ (Gγ1 in FIG. 4I and Gγ5, in FIG. 4J) and different Gβ These results show that combinations of both Gβ and Gγ subunits can lead to distinct pharmacological profile of G-protein activation. These differences could be, in part, linked to distinct pharmalogical profiles observed with different cells and tissues expressing not only a specific set of Gα subunits but also different combination and levels of Gβ and Gγ subunits. These results show that a βγIP-based biosensor could be useful to study and better understand these differences.

FIGS. 5A and 5B show the selective inhibition of Gα$_{i1}$ by PTX (a Gα$_i$/Gα$_o$ blocker), and Gα$_q$ by Ubo-Qic (an analog of the Gα$_q$ inhibitor: YM-254890). HEK293 cells expressing the TPαR and Gα$_q$ (FIG. 5A) or the D$_2$R and Gα$_{i1}$ (FIG. 5B), along with Gβ1, Rluc-Gγ5 and GRK2-GFP, were pre-treated with PTX, Ubo-Qic or vehicle (control) and then exposed to increasing concentrations of U-46619 (FIG. 5A) or rotigotine (FIG. 5B) for 15 min, before recording BRET signals. In FIG. 5C, TPαR-mediated G-protein activation was used to validate Ubo-Qic inhibitor selectivity. Cells co-expressing TPαR and the biosensor GRK2-GFP/Rluc-Gγ5/Gβ1+the indicated Gα subunit were pretreated with Ubo-Qic and exposed to either vehicle or an agonist: U-46619 (100 nM). These results show that, from the Gα$_q$ family (Gα$_q$, Gα$_{11}$, Gα$_{14}$ and Gα$_{15}$), only Gα$_{15}$ is insensitive to Ubo-Qic. The Gα$_{12}$ and Gα$_{13}$ proteins are also insensitive to Ubo-Qic. FIG. 5D, the βγIP-based biosensor was used to reveal the Ubo-Qic sensitivity of mutant Gα$_q$ activation. Gα$_q$ substitutions were introduced at position 67 (see FIG. 14). Only the substitutions of this tyrosine residue that are resistant to Ubo-Qic inhibition (Y67C, Y67G, Y67S & Y67L) also showed promiscuous properties, indicating that this residue could also be important for controlling G-protein activation. The substitution of the Phe75 residue to glycine led to only a partial Ubo-Qic mediated inhibition of activation (FIG. 5D) and also to a promiscuous phenotype (see FIG. 4A).

FIG. 6A: HEK293 cells transiently expressing the D$_2$R along with Gα$_{i1}$, Gβ1, Rluc-Gγ5 and GRK2-GFP were exposed to 1 μM of rotigotine or vehicle while BRET measurements were performed at regular intervals. FIG. 6B: HEK293 cells transiently expressing the TPαR along with Gα$_{11}$, Gβ1, Rluc-Gγ5 and GRK2-GFP were exposed to 100 nM of U-46619 or vehicle while BRET measurements were performed at regular intervals. In both cases, the agonist and vehicle were added to the cells after 30 sec of measurements.

FIG. 8A: G-protein activation profile of HEK293 cells transiently expressing the angiotensin II type 1 receptor (AT1R) along with Gβ1, Rluc-Gγ5, GRK2-GFP and the indicated Gα, stimulated with 1 μM angiotensin II for 15 min prior to BRET measurements. FIG. 8B: G-protein activation profiles for a saturating concentration of angiotensin II analogs (1 μM) for Gα$_q$, Gα$_{11}$ and Gα$_{12}$. Results in FIGS. 8A and 8B are expressed as a percentage of the BRET signal obtained in vehicle treated cells, and mock condition without any Gα subunit overexpression, was used to determine the threshold of a positive response. FIG. 8C: Dose-response curves obtained using the AngII and DVG ligands for Gα$_q$ and Gα$_{12}$ activation of the AT1R using the GRK2-GFP/Rluc-Gγ5/Gβ1 biosensor. Data is expressed as the % of the AngII response obtained for each G-protein.

FIG. 9A: Z' factor obtained for HEK293 cells transfected with the TPαR, GRK2-RlucF1, RlucF2-Gγ5, Gβ1 and Gα$_{11}$ subunit, stimulated with 100 nM of U-46619 or vehicle for 10 min. Luminescence values are represented for each individual well of a 96-well plate. Z' factor, for this representative experiment, was evaluated at 0.53. FIG. 9B: Dose-response curves using the agonist U-46619 for Gα$_{11}$ activation of the TPαR using GRK2-RlucF1/RlucF2-Gγ5/Gβ1 biosensor.

FIG. 10A: Dose response curves obtained from HEK293 cells transiently expressing the D$_2$R along with Gα$_{i1}$, Gβ1, Rluc-Gγ5 and GRK2-GFP (black circles) or GRK3-GFP (white triangles), exposed to increasing concentrations of the agonist rotigotine for 15 min prior to BRET measurements. FIG. 10B: Kinetics of GRK3-based biosensor response for HEK293 cells transfected with D$_2$R, Gα$_{i1}$, Gβ1, Rluc-Gγ5 and GRK3-GFP, exposed to 1 μM of rotigotine or vehicle while BRET measurements were performed at regular interval. The agonist and vehicle were injected to the cells after 30 sec of measurements. FIG. 10C: Z' factor evaluation of GRK3-based biosensor for HEK293 cells transfected with D$_2$R, Gα$_{i1}$, Gβ1, Rluc-Gγ5 and GRK3-GFP, exposed to either 1 μM of rotigotine or vehicle for 15 min. BRET ratios are represented for each individual well of a 96-well plate. Z' factor, for this representative experiment, was evaluated at 0.71.

FIGS. 11A to 11D show the results of experiments performed using a polycistronic vector encoding a βγIP-based G-protein activation biosensor. FIG. 11A: Schematic diagram illustrating the polycistronic construct which encodes the following proteins: GRK2-GFP, Rluc-Gγ5 and Gβ1. A G-protein activation profile is presented in FIG. 11B, for HEK293 cells co-transfected with constructs encoding for TPαR, a Gα (either Gα$_q$, Gα$_{11}$, Gα$_{12}$, Gα$_{13}$, Gα$_{14}$ or Gα$_{15/16}$; Mock condition was without Gα) and a polycistronic construct (described in FIG. 11A) encoding the GFP-tagged WT GRK2 or a RGS-dead mutant (D110A) of GRK2. TPαR activation by its agonist (100 nM of U46619) led to similar results and profile with both polycistronic constructs, indicating that a functional RGS domain is not a prerequisite for GRK2 recruitment. FIG. 11C: Dose-response curves using the agonist U-46619 for Gα$_{11}$ activation of the TPαR using the polycistronic construct (with WT GRK2) described in FIG. 11A. In FIG. 11D, a Z' factor was obtained for HEK293 cells transfected as in FIG. 11C, and stimulated with 100 nM of U-46619 or vehicle for 15 min. BRET ratios are represented for each individual well of a 96-well plate. Z' factor, for this representative experiment, was evaluated at 0.80.

FIGS. 12A and 12B show a membrane-anchored βγIP-based G-protein activation biosensor. FIG. 12A: Schematic diagram illustrating the principle underlying the use of the membrane anchored GRK2 (GRK2-mem)-based biosensor and the associated DNA construct encoding GRK2-GFP-mem. FIG. 12B: Membrane preparations were obtained from HEK293 cells transfected with TPαR, Gβ1, RlucII-Gγ5, GRK2-GFP or GRK2-GFP-mem, in absence or presence of $G\alpha_{11}$, which were stimulated with 100 nM of U-46619 or vehicle for 15 min. BRET experiments were then performed on those membrane preparations. Data are expressed as a percentage of the BRET signal obtained in vehicle treated cells.

In FIG. 13A, HEK293 cells co-expressing TPαR, $G\alpha_q$, Gβ1, RlucII-Gγ5 and variants of GRK2-GFP (WT=solid square, RGS-dead D110A mutant=empty circle, and catalytically-dead K220R mutant=empty triangle) were stimulated with increasing doses of U46619. As shown in FIGS. 11B and 13A, a functional RGS domain is not required (nor does it promote) the $G\alpha_q$ response detected with the biosensor. A catalytically-dead mutant of GRK2 can also be used with this biosensor (FIGS. 13A and 13C) in two configurations: G-protein activation measured as an increase in BRET from GRK2-GFP interaction with free Gβ1/RlucII-Gγ5 (FIG. 13A) and from RlucII-GRK2 interaction with free Gβ1/GFP10-Gγ5 (FIG. 13C). Using these mutants would minimize the side effects of overexpressing a functional kinase, which is known to inhibit $G\alpha_q$-mediated activation of PLC through its RGS domain. The use of such mutants could be advantageous for applications that require monitoring of multiple signaling pathways through multiplexing of sensors or of different assays. In FIG. 13B, HEK293 cells were transfected as in FIG. 13A but with either WT GRK2 (solid square) or mutants that would prevent (S670A=open triangles, S676A=empty diamonds and S685A=empty circles) or mimic (S670D=solid triangles, S676D=solid diamonds and S685D=solid circles) phosphorylation of its C-terminal binding domain. Phosphorylation of GRK2 on these serine residues by ERK, PKA and CDK2-CyclinA, is known to modulate its activity (Cong et al., *The Journal of Biological Chemistry*, 276, 15192-15199; Pitcher et al., *The Journal of Biological Chemistry*, 274, 34531-34534; Penela et al., *PNAS*, 107(3): 1118-1123; Choudhary et al., *Mol Cell.* 2009 36(2): 326-39). However, the results presented in FIG. 13B provide evidence that GRK2 recruitment to Gβγ could be insensitive to regulation by different signaling events. In FIG. 13C, HEK293 cells co-expressing TPαR, $G\alpha_q$, Gβ1, GFP-Gγ5 and variants of RlucII-GRK2 (WT=solid squares, and catalytically-dead K220R mutant=empty triangles) were stimulated with increasing doses of U46619. Both configurations of BRET donor and acceptor with tags at either N-terminus (FIG. 13C) or C-terminus of GRK2 (FIG. 13A) led to similar results, providing evidence that the configuration of the biosensor is flexible.

FIG. 14 shows a sequence alignment of human G-protein a subunits (SEQ ID NOs: 1-17) and substitutions leading to promiscuous coupling properties. The human Gα subunits of heterotrimeric G-proteins were aligned using DIALIGN tool (http://bibiserv.techfak.uni-bielefeld.de/dialign/submission.html), formatted using the Boxshade tool (http://www.ch.embnet.org/software/BOX_form.html) and a region centered on Linker1 is presented. The residues that show high conservation throughout the Gα subunits are identified with a black and grey background. The Linker1 and a helices from secondary structure prediction are also identified.

FIG. 15A shows a schematic diagram illustrating a biosensor comprising a βγIP (GRK) tagged with a RET acceptor (A) and a GPCR tagged at its C-terminal with a RET donor (D). The assay is also based on the competition between the Gα subunit and the βγIP for the binding to the Gβγ dimer, which is bound to the C-terminal portion of the GPCR. While in the inactive form, the Gα subunit of the heterotrimeric G-protein is tightly bound to the Gβγ dimer. Upon ligand binding to the GPCR, the Gα dissociates from the Gβγ subunits, allowing βγIP to be recruited to the free Gβγ subunits and bringing the RET acceptor in close proximity to the RET donor linked to the GPCR, thus inducing/increasing the BRET signal.

In FIG. 16C, a Z' factor was obtained for HEK293 cells transfected as in FIG. 16B, and stimulated with 100 nM of U-46619 or vehicle for 15 min. BRET ratios are represented for each individual well of a 96-well plate. Z' factor, for this representative experiment, was evaluated at 0.89.

FIG. 17A shows the amino acid sequence of human GRK2 (SEQ ID NO:18), with positions D110, K220R, S670, S676 and S685 (mutated in some of the constructs described herein) in bold, the putative PH domain underlined, and the C-terminal portion thereof (GRK2 Cterm, SEQ ID NO:50) used in some of the constructs described herein in italics.

FIG. 17B shows the amino acid sequence of human GRK3 (SEQ ID NO:19) with the putative PH domain underlined, and the amino acid sequence of the C-terminal portion thereof (GRK3 Cterm, SEQ ID NO:51) used in some of the constructs described herein in italics. FIG. 17C shows the amino acid sequence of PLEKHG2 (SEQ ID NO:20) with the putative PH domain underlined.

FIG. 17D shows the amino acid sequence of GFP10 (SEQ ID NO:38) used in the experiments described herein.

FIG. 17E shows the amino acid sequence of *Renilla reniformis* GFP (rGFP, SEQ ID NO:46) used in the experiments described herein.

FIG. 17F shows the amino acid sequence of RLucII (SEQ ID NO:39) used in the experiments described herein.

DISCLOSURE OF INVENTION

Figure 1A:
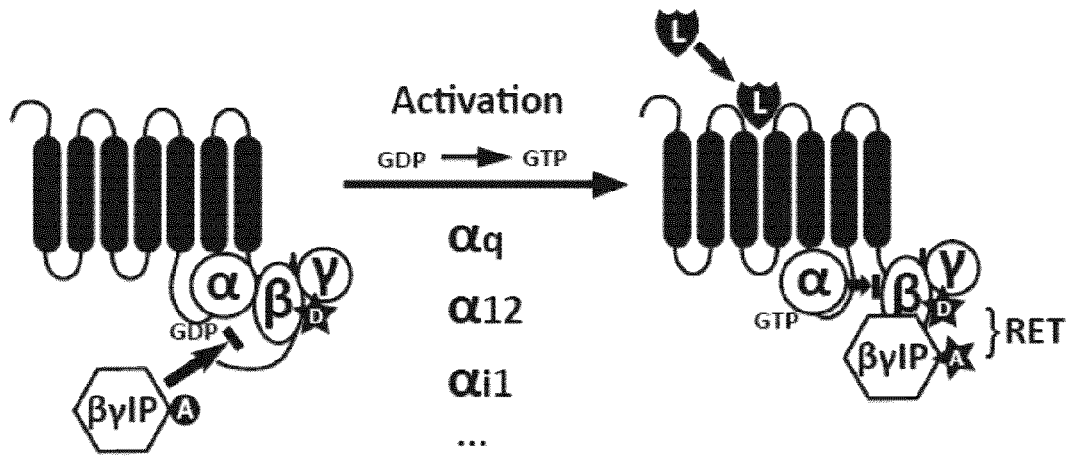
FIGS. 1A to 1C show schematic diagrams illustrating the principle underlying the use of the βγIP-based biosensor for G-protein activation, using a GPCR as an example of G-protein activator. The assay is based on the competition between the Gα subunit and the βγIP for the binding to the Gβγ dimer. While in the inactive form, the Gα subunit of the heterotrimeric G-protein is tightly bound to the Gβγ dimer. Upon ligand binding to the receptor, the Gα subunit switches from a GDP-bound form to a GTP-bound form, resulting in its dissociation from the Gβγ subunits, allowing βγIP to be recruited to the free Gβγ subunits. The interaction between βγIP and Gβγ will thus reflect the activation of a specific G-protein, upon receptor stimulation. Different methods of detection can be used to assess this interaction between βγIP and Gβγ, such as resonance energy transfer (RET) approaches (FIG. 1A) or protein complementation (PC) assays (FIG. 1B). In resonance energy transfer approaches, the βγIP and Gβγ are tagged with an energy donor and acceptor, and upon G-protein activation, an increase in RET signal is observed. In the case of protein complementation assay, the βγIP and Gβγ are fused to fragments of a fluorescent protein or luminescent enzyme, and following G-protein activation, the complementation of the two fragments will lead to an increase in the fluorescence signal or enzyme activity.

Terms and symbols of genetics, molecular biology, biochemistry and nucleic acids used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All terms are to be understood with their typical meanings established in the relevant art.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

In the studies described herein, the present inventors have shown that a βγIP-competition-based biosensor may be used to monitor G-protein activation, without the need to modify the receptor and/or the Gα subunits. As it is based on competition, a single biosensor is needed to study all the different G-proteins and establish G-protein activation/coupling profiles based on the co-transfected Gα subunit. G-protein activation profiles are not only important for characterizing receptors and drug targets, but may also be useful in the drug discovery process for identifying, characterizing and optimizing GPCR5 ligands with biased signaling properties associated with therapeutic efficacy and reduced side effects.

The present disclosure relates to a universal biosensor for monitoring G-protein activation, without having to modify either Gα protein subunits or G-protein activators (such as G-protein-coupled receptors (GPCR), activators of G-protein signaling (AGS), regulators of G-protein signaling or other chemical and biological entities). More specifically, the disclosure relates to the use of a Gβγ-interacting protein βγIP) to monitor the activation of the various hetero-trimeric G-proteins. Advantageously, the signaling biosensor disclosed herein allows for a sensitive and quantitative assay which can be used in large-scale screening assays and structure-activity relationship studies for the identification of ligands (agonists, antagonists, inverse agonists, allosteric modulators, etc.) targeting G-protein activity. Additionally, the biosensor disclosed herein represents a tool for assessing G-protein activation profiles and allows for compound profiling by addressing which specific G-proteins are activated upon stimulation.

As shown in FIG. 1, the system according to an embodiment of the present disclosure is based on the competition between the Gα subunit and the βγIP for the binding to the Gβγ dimer. While in the inactive form, the Gα subunit of the hetero-trimeric G-protein is tightly bound to the Gβγ dimer. Upon ligand binding to the receptor, the Gα subunit switches from a GDP-bound form to a GTP-bound form, resulting in its dissociation from the Gβγ subunits, allowing βγIP to be recruited to the free Gβγ subunits. The interaction between βγIP and Gβγ will thus reflect the activation of a specific G-protein, upon receptor stimulation.

The present inventors have also shown that it is possible to monitor G-protein activation using a biosensor that measures the recruitment/localization of a βγIP (e.g., GRK), tagged with a BRET donor (e.g., RLuc), at the plasma membrane (where it interacts with the Gβγ complex bound to the GPCR) using a plasma membrane-targeting moiety tagged with a complementary BRET acceptor (e.g., rGFP). The increase in the concentration/density of βγIP at the plasma membrane, an indirect measure of the recruitment of the βγIP to the Gβγ complex, is detected by an increase in the BRET signal.

The present inventors have further shown that it is possible to monitor G-protein activation using a biosensor that measures the recruitment of a βγIP (e.g., GRK), tagged with a BRET donor (e.g., RLuc), to a GPCR-tagged with a complementary BRET acceptor (e.g., rGFP) (FIG. 15).

In this context, the present disclosure relates to a βγIP-based G-protein activation biosensor and a system using such biosensor to assess activation of specific G-proteins promoted by their activators. The system comprises a G-protein activator; a Gα protein; and the biosensor described herein. The present disclosure further relates to a method for detecting G-proteins activation using the system disclosed herein.

The present disclosure thus relates to a biosensor system for detecting G-protein activity, said biosensor system comprising the elements defined in (A) or (B):

(A) (i) a first biosensor comprising: a first component comprising a Gβγ interacting protein (βγIP) fused to (a) a RET donor; (b) a RET acceptor or (c) a first fragment of a reporter protein; and a second component comprising a fused Gβ protein or a fused Gγ protein, wherein said Gβ protein or said Gγ protein is fused to (a) a RET donor; (b) a RET acceptor or (c) a second fragment of said reporter protein; (ii) a second biosensor comprising: the first and second components defined in (i); and a third component comprising a recombinant Gα protein; wherein (a) if said βγIP is fused to said RET donor, said Gβ or Gγ protein is fused to said RET acceptor;

(b) if said βγIP is fused to said RET acceptor, said Gβ or Gγ protein is fused to said RET donor;

and (c) if said βγIP is fused to said first fragment of said reporter protein, said Gβ or Gγ protein is fused to said second fragment of said reporter protein; or (B) (i) a biosensor comprising a first component comprising a Gβγ interacting protein (βγIP) fused to (a) a RET donor; (b) a RET acceptor or (c) a first fragment of a reporter protein; a second component comprising a fused G-protein coupled receptor (GPCR), wherein said GPCR is fused at its C-terminal to (a) a RET donor; (b) a RET acceptor or (c) a second fragment of said reporter protein; a third component comprising a recombinant Gα protein; wherein (a) if said βγIP is fused to said RET donor, said GPCR is fused to said RET acceptor; (b) if said βγIP is fused to said RET acceptor, said GPCR is fused to said RET donor; and (c) if said βγIP is fused to said first fragment of said reporter protein, said GPCR is fused to said second fragment of said reporter protein.

The present disclosure thus relates to a biosensor comprising: (1) a first component comprising a Gβγ-interacting protein (βγIP) fused to (a) a RET donor; (b) a RET acceptor or (c) a first fragment of a reporter protein; (2) a second component comprising a fused Gβ protein or a fused Gγ protein, wherein said Gβ protein or said Gγ protein is fused to (a) a RET donor; (b) a RET acceptor or (c) a second fragment of said reporter protein; (3) a third component comprising a recombinant Gα protein, wherein said recombinant Gα protein is a promiscuous or non-selective Gα protein, for example a Gα protein comprising a mutations at a position corresponding to residue 66, 67 and/or 75 of human $G\alpha_q$, as described herein. In an embodiment, the biosensor further comprises a GPCR (native or recombinant), preferably an orphan GPCR.

In an embodiment, the biosensor defined above further comprises a recombinant Gβ protein and/or a recombinant Gγ protein. In a further embodiment, the biosensor defined above further comprises a recombinant Gβ protein and a recombinant Gγ protein. In an embodiment, the biosensor defined above further comprises a GPCR, in a further embodiment a recombinant GPCR.

In another aspect, the present disclosure thus relates to a biosensor comprising (i) a first component comprising a Gβγ interacting protein (βγIP) fused to (a) a RET donor; (b) a RET acceptor or (c) a first fragment of a reporter protein; and (ii) a second component comprising a fused plasma membrane (PM)-targeting moiety, wherein said PM-targeting moiety is fused to (a) a RET donor; (b) a RET acceptor or (c) a second fragment of said reporter protein; wherein (a) if said βγIP is fused to said RET donor, said PM-targeting moiety is fused to said RET acceptor; (b) if said βγIP is fused to said RET acceptor, said PM-targeting moiety is fused to said RET donor; and (c) if said βγIP is fused to said first fragment of said reporter protein, said PM-targeting moiety is fused to said second fragment of said reporter protein.

In one non-limiting embodiment, activity of the herein described biosensor is detectable based on a technique selected from resonance energy transfer (RET) such as bioluminescence resonance energy transfer (BRET) or fluorescence resonance energy transfer (FRET); protein complementation assay or protein-fragment complement assay (PCA) such as enzyme fragment complementation (EFC) or bimolecular fluorescence complementation (BiFC); and the like (see FIG. 1). Such techniques are known in the art and employ tags/moieties which may be fused at the C-terminal, the N-terminal or within the protein elements of the biosensor.

In resonance energy transfer approaches, the βγIP and Gβγ are tagged with an energy donor and acceptor, and upon G-protein activation, an increase in RET signal is observed. In the case of protein complementation assay, the βγIP and Gβγ are tagged with fragments of a reporter protein, such as a fluorescent protein or luminescent enzyme, and following G-protein activation, the complementation of the two fragments will lead to an increase in the reporter protein signal, for example the fluorescence signal or enzyme activity.

Resonance energy transfer (abbreviated RET) is a mechanism describing energy transfer between two chromophores, having overlapping emission/absorption spectra. When the two chromophores (the "donor" and the "acceptor"), are within a short distance (e.g., 10-100 Angstroms) of one another and their transition dipoles are appropriately oriented, the donor chromophore is able to transfer its excited-state energy to the acceptor chromophore through non-radiative dipole-dipole coupling. One type of RET is Bioluminescence Resonance Energy Transfer (BRET) that is based on the non-radiative transfer of energy between a donor bioluminophore (bioluminescent enzyme such as luciferase) and an acceptor fluorophore (ex: GFP or YFP). Another type of RET is Fluorescence Resonance Energy Transfer (FRET) involves the transfer of energy from an excited donor fluorophore to an adjacent acceptor fluorophore. For example, CFP and YFP, two color variants of GFP, can be used as donor and acceptor, respectively.

As used herein, the term "fluorescent protein" refers to any protein that becomes fluorescent upon excitation at an appropriate wavelength. A broad range of fluorescent proteins have been developed that feature fluorescence emission spectral profiles spanning almost the entire visible light spectrum. Non-limiting examples of green Fluorescent Protein include EGFP, GFP10, Emerald, Superfolder GFP, Azami Green, mWasabi, TagGFP, TurboGFP, AcGFP, ZsGreen and T-Sapphire. Non-limiting Examples of blue fluorescent protein include EBFP, EBFP2, Azurite and mTagBFP. Non-limiting examples of Cyan Fluorescent proteins include ECFP, mECFP, Cerulean, mTurquoise, CyPet, AmCyan1, Midori-Ishi Cyan, TagCFP, mTFP1 (Teal). Non-limiting examples of Yellow fluorescent proteins include EYFP, Topaz, Venus, mVenus, mCitrine, mAmetrine, YPet, TagYFP, PhiYFP, ZsYellow1 and mBanana. Non-limiting Examples of orange fluorescent proteins include Kusabira Orange, Kusabira Orange2, mOrange, mOrange2, dTomato, dTomato-Tandem, TagRFP, DsRed, DsRed2, DsRed-Express (T1), DsRed-Monomer and mTangerine. Non-limiting Examples of red fluorescent proteins include mRuby, mApple, mStrawberry, AsRed2, mRFP1, JRed, mCherry, HcRed1, mRaspberry, dKeima-Tandem, HcRed-Tandem, mPlum and AQ143.

"Overlap" as used in the context of the present invention refers to the ability of the emitted light from a donor fluorescent protein or a luminescent enzyme (e.g., luciferase) to be of a wavelength capable of excitation of a fluorophore (acceptor fluorescent protein) placed in close proximity, usually within about 10-100 Å (about 1-10 nm). Accordingly, the donor fluorescent or luminescent protein and the acceptor fluorescent protein are selected so as to enable the transfer of energy from the donor fluorescent or luminescent protein, attached to a first component of the biosensor, to the acceptor fluorescent protein attached to a second component of the biosensor, when the first and second components are in close proximity (i.e., in the form of a complex or in the same cellular compartment, such as the plasma membrane). Such transfer of energy is commonly referred to as "Fluorescence (or Förster) Resonance Energy Transfer" or "FRET" (if the donor protein is a fluorescent protein), or "Bioluminescence Resonance Energy Transfer" or "BRET" (if the donor protein is a bioluminescent protein). Thus, any combination of donor fluorescent or luminescent protein and acceptor fluorescent proteins may be used in accordance with the present invention as long as the above criteria are met. Such combinations are typically referred as FRET or BRET pairs. The choice of a suitable fluorophore for use in a BRET assay will be known to one of skill in the art. In one embodiment, fluorophores include green fluorescent protein-wild type (GFP-wt), yellow fluorescent protein (YFP), Venus, Topaz, ZsYellow1, mOrange2, mKeima, blue fluorescent protein (BFP), cyan fluorescent protein (CFP), Tsapphire, mAmetrine, green fluorescent protein-2 (GFP2), renilla GFP (rGFP) and green fluorescent protein-10 (GFP10), or variants thereof. Fluorescent proteins having an excitation peak close to 400 nm may be particularly suitable. More particular examples of fluorophores include mAmetrine, cyan fluorescent protein (CFP), and GFP10. Representative examples of FRET pairs include BFP/CFP, BFP/GFP, BFP/YFP, BFP/DsRed, CFP/GFP, CFP/YFP, CFP/mVenus, GFP/YFP, GFP2/YFP, GFP/DsRed, TagBFP/TagGFP2, TagGFP2/TagRFP and the like (see, e.g., Müller et al., *Front. Plant Sci.,* 4: 413, 2013). Representative examples of BRET pairs include luciferase (Luc)/GFP, LucNenus, Luc/Topaz, Luc/GFP-10, Luc/GFP-2, Luc/YFP, Luc/rGFP, and the like.

As used herein, the term "luciferase" refers to the class of oxidative enzymes used in bioluminescence and which is distinct from a photoprotein. One example is the firefly luciferase (EC 1.13.12.7) from the firefly *Photinus pyralis* (*P. pyralis* luciferase). Several recombinant luciferases from several other species including luciferase from *Renilla reniformis* (GENBANK: AAA29804) and variants thereof (e.g., a stable variant of *Renilla* Luciferase e.g., RlucII (GENBANK: AAV52877.1), Rluc8 (GENBANK: EF446136.1) *Gaussia* Luciferase (Gluc, GENBANK: AAG54095.1), NanoLuc® Luciferase (Promega®) are also commercially available. Any luciferase can be used in accordance with the present invention as long as it can metabolize a luciferase substrate such as luciferins. Luciferins are a class of light-emitting heterocyclic compounds that are oxidized in the presence of luciferase to produce oxyluciferin and energy in the form of light. Non-limiting examples of luciferins include D-luciferin, imidazopyrazinone-based compounds such as coelenterazine (coelenterazine 400A (DeepBlueC™), coelenterazine H and e-coelenterazine derivatives such as methoxy e-Coelenterazine (Prolume® Purple I from NanoLight Technology®), ViviRen™ (from Promega®), Latia luciferin ((E)-2-methyl-4-(2,6,6-trimethyl-1-cyclohex-1-yl)-1-buten-1-ol formate), bacterial luciferin, Dinoflagellate luciferin, etc. Luciferase substrates may have slightly different emission spectra and will thus be selected to favor the optimal energy transfer to the acceptor. In an embodiment, the luciferase is wild-type (or native) *Renilla* Luciferase. In an embodiment, the luciferase is the stable variant of *Renilla* luciferase Rluc8. In another embodiment, the luciferase is *Gaussia* luciferase (GLuc). In a specific embodiment, the luciferase is *Renilla* Luciferase II (RlucII) and the luciferin is coelenterazine 400A.

In an embodiment, one of the following BRET configurations is used in the biosensors and methods described herein: BRET1 that comprises coelenterazine-h (coel-h) and a YFP (YFP) or a GFP from *Renilla* (rGFP); BRET2 that comprises coelenterazine-400a (coel-400a) and a UV-excited (uvGFP) or a GFP from *Renilla* (rGFP); or BRET3 that comprises coel-h or v-coelenterazine (from Nanolight Technology®) and the monomeric orange FP (mOrange). In a further embodiment, RLucII is used in the above-noted BRET configurations. In another embodiment, one of the following BRET configurations is used in the biosensors and methods described herein: RlucII/coel-400a/enhanced blue (EB) FP2, RlucII/coel-400a/super cyan fluorescent protein (SCFP3A), RlucII/coel-400a/mAmetrine or RlucII/coel-400a/GFP10. In an embodiment, the BRET donor is a *Renilla* luciferase (e.g., RLucII) and the BRET acceptor is a *Renilla* GFP (e.g., *Renilla reniformis* GFP).

In PCA, each of the proteins (e.g., βγIP and Gβ/Gγ, or GPCR) is covalently linked to incomplete fragments of a reporter protein, and the interaction between βγIP and Gβ/Gγ brings the fragments of the reporter protein in close enough proximity to allow them to form a functional reporter protein whose activity can be measured. Any protein that can be split into two parts and reconstituted non-covalently may be used in the PCA-based biosensor. The term "reporter protein" refers to a protein that can be detected (e.g., by fluorescence, spectroscopy, luminometry, etc.) easily and that is not present normally (endogenously) in the system used. Typical reporter proteins used in PCA include enzymes (whose activity may be measured using a suitable substrate) such as dihydrofolate reductase (DHFR), β-lactamase, β-galactosidase or proteins that give colorimetric or fluorescent signals such as a luciferase (e.g., *Renilla* luciferase), GFP and variants thereof.

In another non-limiting embodiment, the RET or PCA tags are located on: (i) the βγIP and the Gβ protein, or (ii) the βγIP and the Gγ protein. In a further non-limiting embodiment, the βγIP and the Gβ or Gγ subunits are tagged at their N-terminus, C-terminus or at any internal region within the proteins. In one embodiment, the βγIP and the Gβ or Gγ subunits are tagged at their N-terminus or C-terminus. In one non-limiting embodiment, the herein described PCA tags added to the βγIP and the Gβ or Gγ subunits can be, without being limited to, a fluorophore, a luciferase or a fragment thereof comprising a portion of a fluorescent protein or luminescent enzyme.

"GPCR" refers to full length native GPCR molecules as well as mutant/variant GPCR molecules. A list of GPCRs is given in Foord et al (2005) *Pharmacol Rev.* 57, 279-288, which is incorporated herein by reference, and an updated list of GPCRs is available in the IUPHAR-DB database (Harmar A J, et al. (2009) IUPHAR-DB: the IUPHAR database of G protein-coupled receptors and ion channels. *Nucl. Acids Res.* 37 (Database issue): D680-D685; Sharman J L, et al., (2013) IUPHAR-DB: updated database content and new features. *Nucl. Acids Res.* 41 (Database Issue): D1083-8; Alexander S P H, Benson H E, Faccenda E, Pawson A J, Sharman J L, Spedding M, Peters J A and Harmar A J, CGTP Collaborators. (2013) The Concise Guide to PHARMACOLOGY 2013/14: G Protein-Coupled Receptors. *Br J Pharmacol.* 170: 1459-1581). In an embodiment, the GPCR is an orphan GPCR. The term "orphan GPCR" as used herein refers to an apparent receptor that has a similar structure to other identified GPCRs but whose endogenous ligand has not yet been identified. GPCR orphan receptors are often given the name "GPR" followed by a number, for example GPR1. An updated list of orphan GPCRs is available in the IUPHAR-DB database described above.

In an embodiment, the GPCR is fused at its C-terminal to a RET donor or RET acceptor, in a further embodiment a RET donor, such as a luciferase (RLuc).

The term "recombinant" as used herein refers to a protein molecule which is expressed from a recombinant nucleic acid molecule, i.e. a nucleic acid prepared by means of molecular biology/genetic engineering techniques, for example a protein that is expressed following transfection/transduction of a cell (or its progeny) with a nucleic acid (e.g., present in a vector) encoding the protein (as opposed to a protein that is naturally expressed by a cell).

The term variant (or mutant) as used herein refers to a protein which is substantially similar in structure (amino acid sequence) and biological activity to the corresponding native protein. It includes fragments comprising one or more domains of a native protein, as well as fusion proteins comprising the native protein or a fragment thereof. A variant may comprises one or more mutations (substitutions, deletions, insertions) relative to the native protein in order to generate a protein having certain desired features, for example being constitutively active, inactive, altered binding to one or more ligands, etc. Individual substitutions, deletions or additions that alter, add or delete a single amino acid or-nucleotide or a small percentage of amino acids or nucleotides in the sequence create a "conservatively modified variant," where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

"Homology" or "identity" and "homologous" or "identical" refer to sequence and/or structural similarity between two polypeptides or two nucleic acid molecules. Homology/identity can be determined by comparing each position in the aligned sequences. A degree of homology/identity between nucleic acid or between amino acid sequences is a function of the number of identical or matching nucleotides or amino acids at positions shared by the sequences. As the term is used herein, a nucleic acid sequence is homologous to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 65%, 70%, 75%, 80%, 85%, 90%, 95%, 96%, 97%, 98% or 99%. As used herein, a given percentage of homology/identity between sequences denotes the degree of sequence identity in optimally aligned sequences. An "unrelated" or "non-homologous" sequence shares less than 40% identity, though preferably less than about 25% identity, with any of the sequences described herein.

In one non-limiting embodiment, the system includes a living cell, a membrane preparation, or both. The system defined herein is, but not limited to, a membrane preparation and said βγIP is tethered to the membrane via a membrane targeting linker, for example a protein/peptide linker comprising a plasma membrane (PM)-targeting domain (e.g., a plasma membrane-anchoring signal peptide). This plasma membrane-targeting domain may be, without being limited thereto, a lipid group covalently bound to the peptide chain such as palmitoylation, myristoylation or prenylation modifications (as the membrane anchoring signal from KRAS for example (Hancock 2003)), a transmembrane domain, or a polybasic region (as the one present in GRK5 for instance).

In an embodiment, the PM-targeting moiety comprises a CAAX motif (C is cysteine residue, AA are two aliphatic residues, and X represents any amino acid. CAAX motifs are found in "CAAX proteins" that are defined as a group of proteins with a specific amino acid sequence at C-terminal that directs their post translational modification. CAAX proteins encompass a wide variety of molecules that include nuclear lamins (intermediate filaments) such as prelamin A, lamin B1 and lamin B2, Ras and a multitude of GTP-binding proteins (G proteins) such as Ras, Rho, Rac, and Cdc42, several protein kinases and phosphatases, etc. (see, e.g., Gao et al., *Am J Transl Res*. 2009; 1(3): 312-325). The proteins that have a CAAX motif or box at the end of the C-terminus typically need a prenylation process before the proteins migrate to the plasma membrane or nuclear membrane and exert different functions. In an embodiment, the CAAX box is derived from a human RAS family protein, for example HRAS, NRAS, Ral-A, KRAS4A or KRAS4B. The last C-terminal residues of RAS, NRAS, KRAS4A or KRAS4b (referred to as the hypervariable region or HVR) are depicted below, with the putative minimal plasma membrane targeting region in italics and the CAAX box underlined (see, e.g., Ahearn et al., *Nature Reviews Molecular Cell Biology* 13: 39-51, January 2012): HRAS: KLNPPDESGPGCMSCKCVLS; (SEQ ID NO:40); NRAS: KLNSSDDGTQGCMGLPCVVM; (SEQ ID NO: 41); KRAS4A: KISKEEKTPGCVKIKKCIIM; (SEQ ID NO:42); KRAS4B: KMSKDGKKKKKKSKTKCVIM; (SEQ ID NO:43); Ral-A/Ral1: KNGKKKRKSLAKRIRER CCIL (SEQ ID NO:44). In an embodiment, the membrane targeting moiety comprises the last 4 residues of the sequences depicted above. In a further embodiment, the membrane targeting moiety comprises the last 10 residues of the sequences depicted above. In an embodiment, the membrane targeting moiety comprises the C-terminal portion (e.g., about the last 10-30 or 15-25 amino acids) of a CAAX protein, for example a human RAS family protein, e.g., about the last 10-30, 15-25 or 20 amino acids of a human RAS family protein.

In an embodiment, the PM-targeting moiety comprises the sequence KKKKKKSKTKCVIM (SEQ ID NO: 37) from KRAS4B. In another embodiment, the PM targeting moiety comprises the the plasma-membrane targeting palmitoylation sequence from hRas and prenylation signal sequence from Ral-A/Ral1 (sequence: CMSCKCCIL, SEQ ID NO:45).

Several proteins also contain a non-lipid, polybasic domain that targets the PM such as Ras small GTPases, phosphatase PTEN, nonreceptor tyrosine kinase Src, actin regulators WASP and MARCKS, and G protein-coupled receptor kinases (GRKs) such as GRK5. In an embodiment, the polybasic domain is from GRK5, and comprises the sequence SPKKGLLQRLFKRQHQNNSKS (SEQ ID NO:46). In an embodiment, the PM-targeting moiety is fused at the C-terminal end of a RET donor or acceptor, and in a further embodiment a RET acceptor such as a GFP (e.g., rGFP). In another embodiment, the PM-targeting moiety is fused at the C-terminal end of a RET donor or acceptor, and in a further embodiment a RET acceptor such as a GFP (e.g., rGFP), and the RET donor or acceptor is fused at its N-terminal to a βγIP, such as a GRK protein or a Gβγ-interacting fragment/variant thereof.

According to the present disclosure, G-protein activator include, but is not limited to, classical activation of G-proteins by GPCRs and other proteins that can also modulate the activity of these hetero-trimeric G-proteins, such as regulators of G-protein signaling (RGS), activators of G-protein signaling (AGS), and resistance to inhibitors of cholinesterase 8 proteins (Ric-8). In some of these non-canonical signaling pathways, the guanine exchange factor (GEF) activity classically exerted by GPCRs is replaced by another protein such as Ric-8 for example (Boularan and Kehrl, 2014).

In one embodiment, the G-protein activator is a member of the GPCR family.

Gα protein subunit as defined herein includes, but is not limited to, the 17 different known isoforms, their splice variants, and any mutated Gα proteins, for example those leading to non-selective/promiscuous Gα. In one non-limiting embodiment, the herein described Gα protein is selected amongst any of the natural mammalian Gα proteins, which includes $G\alpha_q$, $G\alpha_s$, $G\alpha_{i1}$, $G\alpha_{i2}$, $G\alpha_{i3}$, $G\alpha_{t\text{-}cone}$, $G\alpha_{t\text{-}rod}$, $G\alpha_{t\text{-}gust}$, $G\alpha_z$, $G\alpha_{on}$, $G\alpha_{oB}$, $G\alpha_{olf}$, $G\alpha_{11}$, $G\alpha_{12}$, $G\alpha_{13}$, $G\alpha_{14}$, and $G\alpha_{15/16}$ (now designated GNA15), the splice variants of these isoforms, as well as functional variants thereof. In an embodiment, the Gα protein subunit is of the $G_i$ family. In an embodiment, the Gα protein subunit is of the $G_s$ family. In an embodiment, the Gα protein subunit is of the $G_q$ family. In an embodiment, the Gα protein subunit is of the $G_{12,13}$ family. In an embodiment, the Gα protein is a promiscuous or non-selective Gα protein. In a further embodiment, the Gα protein is a mutated Gα proteins (e.g., $Gα_q$ proteins) having a substitution at any of the following positions, G66, Y67, F75 and any combinations thereof, or equivalent conserved substitution in other Gα subtypes, which results in non-selective Gα proteins that are activated by any GPCRs), including orphan receptors (i.e. that are able to interact with GPCRs independently from the preferential natural coupling of these receptors to specific Gα proteins, also commonly referred to as "promiscuous" Gα proteins), are also included in the present disclosure. In an embodiment, the recombinant Gα protein used in the biosensors/methods described herein is a promiscuous Gα protein, and the GPCR is an orphan GPCR.

In another aspect, the present disclosure relates to a mutated Gα polypeptide comprising a mutation at a position corresponding to residue 67 and/or residue 75 of human $Gα_q$ protein. Said mutation may be an insertion, deletion, or a substitution, for example a non-conservative substitution. FIG. 14 discloses an alignment of the sequences of representative hGα proteins that may be mutated according to the present invention, with the positions corresponding 67 and 75 of $Gα_q$ indicated by arrows. The skilled person would understand that depending on the number of residues N-terminal of the positions corresponding 67 and 75 of $Gα_q$ in a particular Gα, the numbering of the residue varies. For example, in $hGα_{14}$, the residue corresponding to position 67 of $Gα_q$ is residue 63 (Y). Similarly, in $hGα_{12}$, the residue corresponding to position 67 of $Gα_q$ is residue 85 (F). Thus, the present invention encompasses for example a mutated $Gα_{14}$ polypeptide comprising a mutation at position 63 (e.g., a substitution for a non-aromatic residue), and a mutated $Gα_{12}$ polypeptide comprising a mutation at position 85 (e.g., a substitution for a non-aromatic residue), which correspond to a mutation at position 67 of $Gα_q$. Any mutated Gα polypeptide comprising a mutation at one or more of positions corresponding to residue 67 and/or residue 75 of human $Gα_q$ protein are encompassed by the present disclosure.

In an embodiment, the present invention relates to a mutated Gα polypeptide comprising any one of the sequences set forth in SEQ ID NOs:1-17, wherein the residue corresponding to residue 67 and/or residue 75 of human $Gα_q$ protein is mutated. In an embodiment, the mutation is at a position corresponding to residue 67 of human $Gα_q$ protein. In an embodiment, the mutation is at a position corresponding to residue 67 and is a substitution for a non-aromatic residue, in a further embodiment cysteine. In another embodiment, the mutation is at a position corresponding to residue 75 of human $Gα_q$ protein, and is a substitution for a non-aromatic residue, in a further embodiment the non-aromatic residue is glycine. Such mutated Gα polypeptide may be used in any of the biosensors and/or methods described herein. In one non-limiting embodiment, the mutated $Gα_q$ protein comprises one of the following substitutions, $Gα_q$G66K, $Gα_q$Y67C and $Gα_q$F75G, resulting in non-selective Gα proteins.

In another aspect, the present disclosure relates to a nucleic acid comprising a sequence encoding the above-defined mutated Gα polypeptide. In another aspect, the present disclosure relates to a plasmid or vector comprising the above-defined nucleic acid. In another aspect, the present disclosure relates to a cell (host cell) comprising the above-defined nucleic acid or vector. In another aspect, the present invention provides a kit comprising a nucleic acid encoding the mutated Gα polypeptide defined herein. In an embodiment, the cell has been transfected or transformed with a nucleic acid encoding the mutated Gα polypeptide defined herein. The invention further provides a recombinant expression system, vectors and cells, such as those described above, for the expression of the mutated Gα polypeptide defined herein, using for example culture media and reagents well known in the art. The cell may be any cell capable of expressing mutated Gα polypeptide defined above. Suitable host cells and methods for expression of proteins are well known in the art. Any cell capable of expressing the mutated Gα polypeptide defined above may be used. For example, eukaryotic host cells such as mammalian cells may be used (e.g., rodent cells such as mouse, rat and hamster cell lines, human cells/cell lines). In another embodiment, the above-mentioned cell is a human cell line, for example an embryonic kidney cell line (e.g., HEK293 or HEK293T cells).

In embodiments, the herein described Gβ protein is selected amongst any of the known Gβ proteins, which includes Gβ1, Gβ2, Gβ3 (e.g., a short variant of Gβ3, Gβ3sh), Gβ4 and Gβ5 (Gβ5-S or Gβ5-L), the splice variants of these isoforms, and functional variants thereof. In a further embodiment, the Gβ protein is Gβ1. In another embodiment, the Gβ protein is Gβ3. In a further embodiment, the Gβ protein (e.g., Gβ1) is N-terminally tagged with a BRET acceptor, such as a GFP.

In embodiments, the herein described Gγ protein is selected amongst any of the known human Gγ proteins, which include Gγ1, Gγ2, Gγ3, Gγ4, Gγ5, Gγ7, Gγ8, $G_19$, Gγ10, Gγ11, Gγ12 and Gγ13, and functional variants thereof. In a further embodiment, the Gγ protein is Gγ5. In a further embodiment, the Gγ protein (e.g., Gγ5) is N-terminally tagged with a BRET donor, such as a luciferase. In another embodiment, the Gγ protein (e.g., Gγ5) is N-terminally tagged with a BRET acceptor, such as a GFP. In another embodiment, the Gγ protein (e.g., Gγ5) is N-terminally tagged with a first domain of a PCA-compatible reporter protein, e.g. a luciferase (e.g., *Renilla* luciferase).

In an embodiment, the herein described βγIP is a protein that interacts with Gβγ dimer upon dissociation of the Gαβγ heterotrimer and that comprises a pleckstrin homology (PH) domain, such as a G-protein coupled receptor kinase (GRK) protein (GRK2 or GRK3) or functional fragment thereof that comprises the C-terminal pleckstrin homology (PH) domain of a GRK protein (i.e. that maintain the ability to interact with a Gβγ dimer), a pleckstrin homology domain containing family G (with RhoGef domain) member 2 (PLEKHG2). The amino acid sequences of GRK2, GRK3 and PLEKHG2 are depicted in FIGS. 17A-C, with the PH domain underlined. In one non-limiting embodiment, the herein described GRK protein (GRK2 or GRK3) or fragment thereof that maintains the ability to interact with a Gβγ dimer (e.g., that comprises the C-terminal pleckstrin homology (PH) domain of the GRK, such as a C-terminal fragment comprising the sequence set forth in SEQ ID NO:50 or 51) is C-terminally tagged with a BRET acceptor, such as a fluorophore. In an embodiment, the βγIP is GRK2 or GRK3 or a variant/fragment thereof, and it is C-terminally fused with a BRET acceptor, such as a GFP. In another embodiment, the βγIP is a variant of a GRK protein that comprises a mutation that inactivates its regulator of G protein signaling (RGS) domain ("RGS-dead" variant). In a further embodiment, the "RGS-dead" variant of a GRK protein comprises a mutation at a position corresponding to residue D110 of GRK2, for example a D to A substitution. The RGS domain of native human GRK2 (UniProtKB accession P25098) and GRK3 (UniProtKB accession P35626) spans about residues 54 to 175. In another embodiment, the βγIP is a variant of a GRK protein that comprises a mutation that inactivates its kinase domain ("kinase-dead" variant). In a further embodiment, the "kinase-dead" variant of a GRK protein comprises a mutation (e.g., non-conservative substitution) at a position corresponding to residue K220 of GRK2, for example a K to D substitution. The kinase domain of GRK2 (UniProtKB accession P25098) and GRK3 (UniProtKB accession P35626) spans about residues 191 to 453. In another embodiment, the βγIP is a variant of a GRK protein that comprises a mutation in its C-terminal domain, e.g., within the last 30 C-terminal residues. In a further embodiment, the mutation is a serine residue located within the C-terminal domain, and more particularly a serine that may be phosphorylated in the native protein. In a further embodiment, the mutation (e.g., non-conservative substitution) is at a position corresponding to residue S670, S676 and/or S685 of GRK2, for example an S to A and/or an S to D substitution.

In embodiments, the domains of the fusion molecules described herein may be covalently linked either directly (e.g., through a peptide bond) or "indirectly" via a suitable linker moiety, e.g., a linker of one or more amino acids or another type of chemical linker (e.g., a carbohydrate linker, a lipid linker, a fatty acid linker, a polyether linker, PEG, etc. In an embodiment, one or more additional domain(s) may be inserted before (N-terminal), between or after (C-terminal) the domains defined above. In an embodiment, the domains of the fusion molecules are covalently linked through a peptide bond. In another embodiment, one or more of the components of the fusion molecules are linked through a peptide linker. Linkers may be employed to provide the desired conformation of the BRET/FRET label chromophores within the labeled compound, e.g., including the separation between chromophores in a BRET/FRET pair. The linkers may be bound to the C-terminal, the N-terminal, or at an intermediate position. In one embodiment, the linkers are peptide linkers, typically ranging from 2 to 30 amino acids in length, for example about 5 to about 20-25 amino acids. The composition and length of each of the linkers may be chosen depending on various properties desired such as flexibility and aqueous solubility. For instance, the peptide linker may comprise relatively small amino acid residues, including, but not limited to, glycine; small amino acid residues may reduce the steric bulk and increase the flexibility of the peptide linker. The peptide linker may also comprise polar amino acids, including, but not limited to, serine. Polar amino acid residues may increase the aqueous solubility of the peptide linker. Furthermore, programs such as Globplot 2.3 (Linding et al., GlobPlot: exploring protein sequences for globularity and disorder, *Nucleic Acid Res* 2003—Vol. 31, No. 13, 3701-8), may be used to help determine the degree of disorder and globularity, thus also their degree of flexibility. In an embodiment, the peptide linker comprises one or more of the amino acid sequences disclosed in the Examples below.

In one non-limiting embodiment, as illustrated in FIG. 12A, the herein described recombinant βγIP-based construct comprises a βγIP tagged with a fluorophore, a luciferase or a fragment thereof comprising a portion of a fluorescent protein or luminescent enzyme, a linker, preferably a flexible polypeptide linker, and a plasma membrane (PM)-anchoring/targeting domain or signal for tethering the βγIP to the membrane. In an embodiment, the flexible linker has a length corresponding to the length of a random amino acid sequence of about 50 to about 1000, 900, 800, 700, 600 or 500 amino acids, for example a length of about 100 to about 500, 400 or 300 amino acids, preferably a length of about 200 to 400, 200 to 300, or about 200 amino acids. In a further embodiment, the flexible linker comprises a random amino acid sequence of about 50 to about 1000, 900, 800, 700, 600 or 500 amino acids, for example a length of about 100 to about 500, 400 or 300 amino acids, preferably a length of about 200 to 400, 200 to 300, or 200 amino acids. Methods for designing flexible amino acid linkers, and more specifically linkers with minimal globularity and maximal disorder, are known in the art. Tis may be achieved, for example, using the Globplot program described above. The sequence may be further optimized to eliminate putative aggregation hotspots, localization domains, and/or interaction and phosphorylation motifs. In an embodiment, the flexible linker is located between the BRET donor or acceptor (e.g., Rluc or GFP) and the plasma membrane targeting domain. In a further embodiment, the construct has the following configuration: βγIP (e.g., GRK2)—BRET acceptor (e.g., GFP)—flexible linker—PM targeting domain (e.g., CAAX domain).

In one embodiment, the present disclosure relates to a system comprising: a GPCR; a Gα protein selected from the following: $G\alpha_q$, $G\alpha_s$, $G\alpha_{i1}$, $G\alpha_{i2}$, $G\alpha_{i3}$, $G\alpha_{t\text{-}cone}$, $G\alpha_{t\text{-}rod}$, $G\alpha_{t\text{-}gust}$, $G\alpha_z$, $G\alpha_{oA}$, $G\alpha_{oB}$, $G\alpha_{olf}$, $G\alpha_{11}$, $G\alpha_{12}$, $G\alpha_{13}$, $G\alpha_{14}$, and $G\alpha_{15116}$, and mutated non-selective Gα proteins as described herein; a signaling biosensor comprising a GRK protein (GRK2 or GRK3) or fragment thereof that comprises the C-terminal pleckstrin homology (PH) domain of the GRK, tagged with a fluorophore, a luciferase or a fragment thereof comprising a portion of a fluorescent protein or luminescent enzyme, a Gβ protein and a Gγ protein, wherein the Gβ protein or the Gγ protein is tagged with a fluorophore, a luciferase or a fragment thereof comprising a portion of a fluorescent protein or luminescent enzyme.

In one embodiment, the present disclosure relates to a system comprising: a GPCR; a Gα protein selected from the following: $G\alpha_q$, $G\alpha_s$, $G\alpha_{i1}$, $G\alpha_{i2}$, $G\alpha_{i3}$, $G\alpha_{t\text{-}cone}$, $G\alpha_{t\text{-}rod}$, $G\alpha_{t\text{-}gust}$, $G\alpha_z$, $G\alpha_{oA}$, $G\alpha_{oB}$, $G\alpha_{olf}$, $G\alpha_{11}$, $G\alpha_{12}$, $G\alpha_{13}$, $G\alpha_{14}$, and $G\alpha_{15/16}$, and mutated Gα protein having a substitution at a position corresponding to any of the positions of $G\alpha_q$: G66, Y67 and/or F75; a signaling biosensor comprising a GRK protein (GRK2 or GRK3) or fragment thereof that comprises the C-terminal pleckstrin homology (PH) domain of the GRK, tagged with a fluorophore, a luciferase or a fragment thereof comprising a portion of a fluorescent protein or luminescent enzyme, a Gβ1 protein and a Gγ5 protein, wherein the Gβ protein or the Gγ protein is tagged with a fluorophore, a luciferase or a fragment thereof comprising a portion of a fluorescent protein or luminescent enzyme.

In accordance with another broad non-limiting aspect, the present disclosure relates to a system for characterizing a signaling signature of a ligand, the system comprising: an activator of G-protein activity; a Gα protein; and a biosensor or system as described herein.

The present disclosure also relates to a system comprising nucleic acid sequences, which could be but is not limited to, a DNA molecule, RNA molecule, virus or plasmid, encoding proteins as defined in the present disclosure. In an embodiment, the present disclosure also relates to a nucleic acid comprising a sequence encoding one or more of the protein components (e.g., fusion proteins) of the biosensors described herein. In an embodiment, the nucleic acid comprises a sequence encoding a (i) a βγIP, (ii) a first fluorophore, a bioluminescent protein or a fragment thereof comprising a portion of a fluorescent protein or bioluminescent protein; (iii) a Gγ protein; (iv) a second fluorophore, a bioluminescent protein or a fragment thereof comprising a portion of a fluorescent protein or bioluminescent protein and (v) a Gβ protein. In a further embodiment, the nucleic acid further comprises one or more sequences encoding one or more linkers located between the components of the biosensor. In a further embodiment, the nucleic acid further comprises one or more transcriptional regulatory sequence(s), such as promoters, enhancers and/or other regulatory sequences, and/or one or more sequences involved in translation regulation, for example internal ribosome entry site (IRES) sequence(s).

In an embodiment, the nucleic acid is present in a vector/plasmid, in a further embodiment an expression vector/plasmid. Such vectors comprise a nucleic acid sequence capable of encoding the above-defined components (e.g., fusion proteins) of the biosensor described herein operably linked to one or more transcriptional regulatory sequence(s).

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". A recombinant expression vector of the present invention can be constructed by standard techniques known to one of ordinary skill in the art and found, for example, in Sambrook et al. (1989) in *Molecular Cloning: A Laboratory Manual*. A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences, such as for selectable markers and reporter genes, are well known to persons skilled in the art.

A recombinant expression vector comprising a nucleic acid sequence of the present invention may be introduced into a cell (a host cell), which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "cell", "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (*Molecular Cloning: A Laboratory Manual*, $2^{nd}$ Edition, Cold Spring Harbor Laboratory press (1989)), and other laboratory manuals. "Transcriptional regulatory sequence/element" is a generic term that refers to DNA sequences, such as initiation and termination signals, enhancers, and promoters, splicing signals, polyadenylation signals which induce or control transcription of protein coding sequences with which they are operably linked. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

Figure 11A:

In an embodiment and as depicted in FIG. 11A, the nucleic acid or vector encodes more than one of the components (fusion proteins) of the biosensors described herein (i.e. polycistronic construct). In an embodiment, the polycistronic construct (e.g., DNA, vector) comprises a nucleic acid sequence encoding a βγIP and a Gγ protein, each tagged with a suitable fluorophore, a luciferase or a fragment thereof comprising a portion of a fluorescent protein or luminescent enzyme, in addition to a Gβ protein. The system of the invention can be reproduced by co-transfecting this polycistronic construct with a DNA molecule comprising a nucleic acid sequence encoding a Gα protein subunit and a G-protein activator of interest.

In another aspect, the present invention provides a kit comprising the nucleic acids and/or vectors defined herein.

In another aspect, the present disclosure also provides a cell (e.g., host cell) comprising or expressing any of the protein components (e.g., fusion proteins, recombinant proteins) of any of the biosensors described herein. In an embodiment, the cell has been transfected or transformed with a nucleic acid encoding the mutated Gα polypeptide defined herein. The invention further provides a recombinant expression system, vectors and cells, such as those described above, for the expression of the mutated Gα polypeptide defined herein, using for example culture media and reagents well known in the art. The cell may be any cell capable of expressing mutated Gα polypeptide defined above. Suitable host cells and methods for expression of proteins are well known in the art. Any cell capable of expressing the mutated Gα polypeptide defined above may be used. For example, eukaryotic host cells such as mammalian cells may be used (e.g., rodent cells such as mouse, rat and hamster cell lines, human cells/cell lines). In another embodiment, the above-mentioned cell is a human cell line, for example an embryonic kidney cell line (e.g., HEK293 or HEK293T cells). In another aspect, the present disclosure also provides a membrane preparation comprising or expressing any of the protein components (e.g., fusion proteins, recombinant proteins) of any of the biosensors described herein, in a further embodiment a membrane-anchored fusion protein.

The present disclosure further relates to a method for assessing a modulation in the recruitment of a Gβγ-interacting protein (βγIP) to a Gβγ subunit between a first condition and a second condition, said method comprising: providing one of the biosensor defined herein; measuring the BRET acceptor signal in said first and second conditions; wherein a difference in the BRET signal between said first and second conditions is indicative of a modulation in the recruitment of a Gβγ-interacting protein (βγIP) to a Gβγ subunit between the first condition and the second condition. In an embodiment, the first condition is the presence of a test agent and the second condition is the absence of a test agent, wherein a difference in the BRET signal is indicative that the test agent modulates (increases or decreases) the recruitment of the Gβγ-interacting protein (βγIP) to the Gβγ subunit. The recruitment of the Gβγ-interacting protein (βγIP) to the Gβγ subunit may be used as a readout for GPCR and/or G-protein activation.

The present disclosure further relates to a method for detecting G-protein activation comprising a system described herein, the method comprising: 1) contacting said system with a compound that activates a G-protein, and 2) detecting the activation of the G-protein by measuring the signal of the biosensor. The method may further comprise the steps of 3) deriving G-protein functional coupling information from of the signal of the signaling biosensor, and 4) processing the information to determine the G-protein activation profile of the G-protein activator and the signaling signature of the compound. Using a biosensor system that comprises a plurality of biosensors, wherein each of the biosensors comprises a different recombinant Gα protein, it is possible to determine the G-protein coupling profile of any GPCR and/or GPCR ligand, as exemplified in FIGS. 3A and 3B.

The term "compound", "agent", "test compound" or "test agent" refers to any molecule (e.g., drug candidates) that may be screened by the method/biosensor of the invention may be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

The present disclosure further relates to a method for determining whether a test agent modulates the activity of a GPCR, said method comprising measuring the signal emitted by a RET acceptor or reporter protein in the presence and absence of said test agent in one of the biosensor described herein; wherein a higher signal measured in the presence of the agent is indicative that said test agent increases the activity of said GPCR, and a lower signal measured in the presence of the agent is indicative that said agent inhibits the activity of said GPCR. In an embodiment, the method comprises:

(1) providing a biosensor comprising the elements defined in (A), (B) or (C):

(A) (i) a first component comprising a Gβγ interacting protein (βγIP) fused to (a) a RET donor; (b) a RET acceptor or (c) a first fragment of a reporter protein; (ii) a second component comprising a fused Gβ protein or a fused Gγ protein, wherein said Gβ protein or said Gγ protein is fused to (a) a RET donor; (b) a RET acceptor or (c) a second fragment of a reporter protein, wherein (a) if said βγIP is fused to said RET donor, said Gβ or Gγ protein is fused to said RET acceptor; (b) if said βγIP is fused to said RET acceptor, said Gβ or Gγ protein is fused to said RET donor; and (c) if said βγIP is fused to said first fragment of said reporter protein, said Gβ or Gγ protein is fused to said second fragment of said reporter protein; (iii) a third component comprising a recombinant Gα protein; and (iv) a fourth component comprising said GPCR;

(B) (i) a first component comprising a Gβγ interacting protein (βγIP) fused to (a) a RET donor; (b) a RET acceptor or (c) a first fragment of a reporter protein; (ii) a second component comprising said GPCR fused at its C-terminal to (a) a RET donor; (b) a RET acceptor or (c) a second fragment of said reporter protein; (iii) a third component comprising a recombinant Gα protein; wherein (a) if said βγIP is fused to said RET donor, said GPCR is fused to said RET acceptor; (b) if said βγIP is fused to said RET acceptor, said GPCR is fused to said RET donor; and (c) if said βγIP is fused to said first fragment of said reporter protein, said GPCR is fused to said second fragment of said reporter protein; or (C) (i) a first component comprising a Gβγ interacting protein (βγIP) fused to (a) a RET donor; (b) a RET acceptor or (c) a first fragment of a reporter protein;

(ii) a second component comprising a fused plasma membrane (PM)-targeting moiety, wherein said PM-targeting moiety is fused to (a) a RET donor; (b) a RET acceptor or (c) a second fragment of said reporter protein; wherein (a) if said βγIP is fused to said RET donor, said PM-targeting moiety is fused to said RET acceptor; (b) if said βγIP is fused to said RET acceptor, said PM-targeting moiety is fused to said RET donor; and (c) if said βγIP is fused to said first fragment of said reporter protein, said PM-targeting moiety is fused to said second fragment of said reporter protein;

(iii) a third component comprising a recombinant Gα protein; and (iv) a fourth component comprising said GPCR; and (2) measuring the signal emitted by said RET acceptor or reporter protein in the presence and absence of said test agent; wherein a higher signal measured in the presence of the agent is indicative that said test agent increases the activity of said GPCR, and a lower signal measured in the presence of the agent is indicative that said agent inhibits the activity of said GPCR.

In an embodiment, the above-mentioned method further comprises:

(3) measuring the signal emitted by said RET acceptor or reporter protein in the biosensor(s) defined herein in the presence and absence of a test agent and in the presence of a GPCR agonist, wherein the recombinant Gα protein is coupled to the GPCR (i.e. is known to be coupled or activated by the GPCR); and (4) determining whether said test agent is an inhibitor of said Gα protein; wherein a lower signal measured in the presence of the test agent is indicative that the test agent is an inhibitor of the Gα protein, and a similar or higher signal measured in the presence of the test agent is indicative that the test agent is not an inhibitor of the Gα protein.

In an embodiment, the term "higher signal" or "lower signal" as used herein refers to signal that is at least 10, 20, 30, 40, 45 or 50% higher (or lower) relative to the reference signal measured in the absence of the test agent. In another embodiment, the "higher signal" or "lower signal" is determined by showing a statistically significant difference (determined using a suitable statistical analysis) in the signal measured in the presence relative to the absence of the test agent, for example by combining the results obtained in a plurality of samples. Statistical analysis (ANOVA, Student t-test, Chi square, etc.) to determine significant differences between different sets of data are known in the art, and such analysis may be performed using suitable computer programs.

The present disclosure further relates to a method for identifying the Gα protein(s) activated by a GPCR agonist (G-protein profiling/signature of the agonist), said method comprising (i) measuring the signal emitted by said RET acceptor or reporter protein in the presence and absence of said GPCR agonist in a plurality of biosensors as defined herein, wherein each of the biosensors comprises a different recombinant Gα protein; (ii) identifying the Gα protein(s) activated by said GPCR agonist; wherein a higher increase of the signal measured in the presence of the GPCR agonist in a biosensor comprising a recombinant Gα protein relative to a corresponding biosensor not expressing the recombinant Gα protein is indicative that the Gα protein is activated by said GPCR agonist, and wherein a similar or lower increase, or a decrease, of the signal measured in the presence of the GPCR agonist in a biosensor comprising a recombinant Gα protein relative to a corresponding biosensor not expressing the recombinant Gα protein is indicative that the Gα protein is not activated by said GPCR agonist. In an embodiment, the method comprises: (a) measuring the signal emitted by said RET acceptor or reporter protein in the presence and absence of said GPCR agonist in the first and in the plurality of second biosensors of the biosensor system defined herein, and (b) identifying the Gα protein(s) activated by said GPCR agonist; wherein a higher increase of the signal measured in the presence of the GPCR agonist in said second biosensor relative to said first biosensor is indicative that the Gα protein is activated by said GPCR agonist, and wherein a similar or lower increase, or a decrease, of the signal measured in the presence of the GPCR agonist in said second biosensor relative to said first biosensor is indicative that said the Gα protein is not activated by said GPCR agonist.

Positive controls and negative controls may be used in the methods/assays described herein. Control and test samples may be performed multiple times to obtain statistically significant results.

In an embodiment, the above-mentioned methods are high-throughput methods (high-throughput screening, HTS). The term "high-throughput screening" (HIS) as used herein refers to a method that allow screening rapidly and in parallel large numbers of compounds (hundreds, thousands) for binding activity or biological activity against target molecules. Such HTS methods are typically performed in microtiter plates having several wells, for example 384, 1536, or 3456 wells. For HTS, it is important that the readout signal be detected with high sensitivity, accuracy and reproducibility.

Methods and devices to measure the BRET signal are well known in the art. The BRET signal may be measured, for example, by determining the intensity of the BRET acceptor signal (light intensity), and/or by calculating the ratio of the signal or light intensity emitted by the BRET acceptor over the signal or light intensity emitted by the BRET donor (BRET ratio). The BRET signal may be measured using a microplate reader or microscope with a suitable filter set for detecting the BRET donor and/or BRET acceptor light emissions.

It should be understood that any combination/sub-combination of the features or embodiments described herein may be present or used in the biosensors, systems and/or methods described herein.

In an embodiment, the biosensors, systems and/or methods described herein comprises one or more of the constructs/fusion proteins and/or recombinant proteins described in the Examples below and attached Figures, for example Rluc-Gγ1 to Gγ13, GRK-GFP, GRK-RlucF1, RlucF2-Gγ5, GRK2-GFP-mem, Rluc-GRK2, GFP-Gγ5, GFP-CAAX or GPCR-Rluc.

MODE(S) FOR CARRYING OUT THE INVENTION

The present invention is illustrated in further details by the following non-limiting examples.

EXAMPLE 1

Materials and Methods

Reagents. Angiotensin II (AngII; [Asp-Arg-Val-Tyr-Ile-His-Pro-Phe], SEQ ID NO: 49), poly-ornithine, poly-D-lysine, isoproterenol, rotigotine, epinephrine, norepinephrine, phenylephrine and *Pertussis* toxin were from Sigma®. u46619 were from Cayman Chemical® (Ann Arbor, Mich.). [Sar$^1$, Ile$^8$]-AngII (SI) and [Asp$^1$, Val$^5$, Gly$^8$]-AngII (DVG) [Sar1-Val5-D-Phe8] AngII (SVdF) and [Sar1-D-Ala8] AngII were synthesized at the University de Sherbrooke (Canada, QC). UBO-Qic (L-threonine,(3R)-N-acetyl-3-hydroxy-L-leucyl-(aR)-a-hydroxybenzenepropanoyl-2,3-idehydro-N-methylalanyl-L-alanyl-N-methyl-L-alanyl-(3R)-3-[[(2S, 3R)-3-hydroxy-4-methyl-1-oxo-2-[(1-oxopropyl)amino] pentyl]oxy]-L-leucyl-N,O-dimethyl-,(7→1)-lactone (9CI)) was obtained from Institute for Pharmaceutical Biology of the University of Bonn (Germany). Dulbecco's modified Eagles medium (DMEM), fetal bovine serum, OPTI-MEM®, and other cell culture reagents were purchased from Invitrogen®. Coelenterazine 400a, Coelenterazine H and Prolume® Purple I were purchased from either Goldbio®, Biotium® or Nanolight® Technology. Polyethylenimine (PEI; 25 kDa linear; was purchased from Polysciences® (Warrington, Pa., USA). Salmon sperm DNA was purchased from Lifetechnologies (ThermoFisher). Phusion DNA polymerase was from Thermo Scientific®. Restriction enzymes and T4 DNA ligase were obtained from NEB®. Oligonucleotides for mutagenesis and PCR applications were synthetized at BioCorp DNA®.

Expression vectors: Receptors and G-proteins. The plasmid encoding AT1 R was a generous gift from Stéphane Laporte (McGill University, Montréal, Canada). Gα$_q$, Gα$_{11}$, Gα$_{12}$, Gα$_{13}$, Gα$_{14}$, Gα$_{15/16}$, Gα$_{oA}$, Gα$_{oB}$, Gα$_z$, Gα$_s$, Gα$_{i1}$, Gα$_{i2}$, Gα$_{i3}$, Gβ1, TPαR, D$_2$R and α$_{1B}$AR were obtained from the cDNA Resource Center (cDNA.org). Plasmids encoding mutant Gα proteins including Gα$_q$G66K, Gα$_q$Y67C and Gα$_q$F75G, were obtained by site-directed mutagenesis (PCR overlap) of the Gα$_q$ wild-type protein coding sequence using the primers depicted in Table I. The PCR fragments were digested with Acc65I+XhoI restriction enzymes and cloned in pCDNA3.1 Zeo(+) (from Invitrogen®, Carlsbad, Calif.) digested Acc65I+XhoI. DNA sequencing was used for validation of the different constructs and to identify the specific substitutions created from degenerated primers.

TABLE I

Sequences of primers used in the experiments described herein

| Primers | Sequences (5'-3') |
|---|---|

External primers for PCR overlap

Forward (SEQ ID NO: 21) gacctgcgctagcgtttaaacttaagcttggtaccaccatg
Reverse (SEQ ID NO: 22) gtcatccctaggctcgagttagaccagattgtactccttt

Degenerate primers to generate Gly66 substitutions (G66D, G66E, G66N & G66K)

Forward (SEQ ID NO: 23) tgagaatcatccatgggtcaRAWtactctgatgaagataaaag
Reverse (SEQ ID NO: 24) cttttatcttcatcagagtaWTYtgacccatggatgattctca

Degenerate primers to generate Tyr67 substitutions (Y67F, Y67L, Y67W & Y67C)

Forward (SEQ ID NO: 25) gaatcatccatgggtcaggaTKStctgatgaagataaaagggg
Reverse (SEQ ID NO: 26) aagccccttttatcttcatcWTYgtatcctgacccatggatga

Primers to generate Y67S substitution

Forward (SEQ ID NO: 27) agaatcatccatgggtcaggatCctctgatgaagataaaagggg
Reverse (SEQ ID NO: 28) ccccttttatcttcatcagagGatcctgacccatggatgattct

Primers to generate Y67G substitution

Forward (SEQ ID NO: 29) agaatcatccatgggtcaggaGGctctgatgaagataaaagggg
Reverse (SEQ ID NO: 30) ccccttttatcttcatcagagCCtcctgacccatggatgattct

Primers to generate F75G substitution

Forward (SEQ ID NO: 31) tctgatgaagataaaaggggcGGcaccaagctggtgtatcagaa
Reverse (SEQ ID NO: 32) ttctgataccagcttggtgCCgccccttttatcttcatcaga Expression vectors: Biosensor constructs. Rluc-Gγ5 and GFP-Gγ: Plasmid encoding the fusion proteins Rluc-Gγ1 to Gγ13 and GFP1O-Gγ5 were was obtained by PCR amplification of the Gγ coding sequences which were then fused in frame at its N-terminus to the humanized Renilla luciferase II (hRlucII) sequence (a variant of the hRluc previously reported (Leduc, Breton et al. 2009), SEQ ID NO:39) into pcDNA3.1 vector (linker sequence: GSAGT, SEQ ID NO: 33), or to the GFP10 (a variant form of the green fluorescent protein (GFP) previously reported (Mercier, Salahpour et al. 2002, SEQ ID NO:38). GRK2-GFP and GRK3-GFP: GRK2-GFP, GRK3-GFP, GRK2 Cterm (SEQ ID NO:50)-GFP, GRK3 Cterm (SEQ ID NO:51)-GFP were generated by PCR amplification of GRK2 and GRK3, which were then fused at their C-terminus to the GFP10 into pcDNA3.1 Zeo(+) vector, generating a linker of 11 amino acid residues between the GRK and the GFP10 protein (linker sequence: GSAGTGKLPAT, SEQ ID NO: 34). GFP-GRK2 and GFP-GRK3: GRK2-GFP, GFP-GRK2 Cterm (SEQ ID NO:50), GFP-GRK3 Cterm (SEQ ID NO:51) were generated by PCR amplification of GRK2 and GRK3, which were then fused at their N-terminus to the GFP10 (SEQ ID NO:38) into pcDNA3.1 Zeo (+) vector, generating a linker of 7 amino acid residues between the GRK and the GFP10 protein (linker sequence: GSAGTGG, SEQ ID NO:52). GFP- and RlucII-tagged GRK2 mutants were generated by PCR-directed mutagenesis using a similar procedure. GRK2-Rluc F1 and Rluc F2-Gγ5: The GRK2-Rluc F1 was obtained by PCR amplification of the coding sequence for residues 1 to 110 from the humanized Renate luciferase II sequence set forth in SEQ ID NO:39 (Rluc F1), which was subsequently fused to the C-terminus of the GRK2 protein in the pcDNA3.1 Zeo (+) vector, generating a 18 amino acids linker between the Rluc fragment and the GRK2 (linker sequence: GSAGWGKLGSAGSGSAGS, SEQ ID NO:35). The Rluc F2-Gγ5 was obtained by PCR amplification of the coding sequence for residues 111 to 311 from the humanized Renilla luciferase sequence set forth in SEQ ID NO:39 (Rluc F2), which was subsequently fused in frame of the N-terminus of the Gγ5 protein into the pcDNA3.1 Zeo(+) vector, generating a 11 amino acid residues linker between the Rluc fragment and the Gγ5 (linker sequence: GSAGTGSAGTT, SEQ ID NO:36). GRK2-GFP-mem: The GRK2-GFP-mem construct encoding a fusion protein between the GRK2-GFP and a 200 amino acid residues flexible linker followed by the membrane anchoring signal of the human KRAS protein (prenylation motif: CAAX) (Hancock 2003) was generated as follows. First, a linker with a predicted disordered structure was created from a random sequence of 2000 residues. From this sequence, a segment of 200 residues with minimal globularity and maximum disorder index was selected, after elimination of aggregation hotspots, putative localization, interaction and phosphorylation motifs. This 200-amino acid flexible linker (SEQ ID NO:53) was directly synthesized and then fused in frame at the N-terminus of the membrane anchoring signal of human KRAS protein splice variant b (amino acid sequence: KKKKKKSKTKCVIM, SEQ ID NO:37) using FOR amplification. The flexible linker followed by KRAS prenylation signal was then sub-cloned into the GRK2-GFP pcDNA3.1 Zeo(+) vector, at the C-terminus of the GRK2-GFP protein. Polycistronic biosensor vector: The polycistronic vector encoding GRK2-GFP, Rluc-Gγ5 and Gβ1 was developed by first sub-cloning the WT and D110A mutant GRK2-GFP10 fusion proteins into the pLVX vector. Then, sub-cloning of IRES-Gβ1 into pcDNA3.1 Rluc-Gγ5 was performed to obtain pcDNA3.1 Rluc-Gγ5-IRES-Gβ1. Finally, the two constructs were assembled to generate a pLVX vector containing GRK2-GFP-IRES-Rluc- Gγ5-IRES-Gβ1. rGFP-CAAX: Plasmid encoding the fusion protein rGFP-CAAX was obtained by PCR amplification of rGFP coding sequence (SEQ ID NO:46) with a reverse primer encoding a linker (sequence: GSAGTMASNN-TASG, SEQ ID NO:47) and the plasma-membrane targeting polybasic sequence and prenylation signal sequence from KRAS splice variant b: –GKKKKKKSKTKCVIM (named: CAAX, SEQ ID NO:37). The CAAX plasma-membrane targeting sequence is in frame at the C-terminus of the rGFP coding sequence. The PCR fragment is sub-cloned into pcDNA3.1 (+) vector. RlucII-GRK2: The GRK2 cDNA was PCR-amplified and subcloned with RlucII at its N-terminus in pIREShyg3 expression vector (from Clonetech®) with the linker: GGSGSGSGS (SEQ ID NO:48).

Cell culture and transfections. Human embryonic kidney 293 (HEK293) cells were maintained in Dulbecco's Modified Eagle's Medium (DMEM) supplemented with 10% fetal bovine serum, 100 unit/ml penicillin/streptomycin at 37° C. in a humidified atmosphere with 5% $CO_2$. Two days before the experiments, HEK293 cells were transfected with the indicated plasmids using poly-ethylenimine 25-kDa linear (PEI) as a transfecting agent (at a ratio of 3 to 1, PEI/DNA) (Hamdan, Rochdi et al. 2007), and then directly seeded in 96-well plates pre-treated with poly-L-ornithine hydrobromide or Poly-D-Lysine, at a density of 35,000 cells per well (for BRET and PCA assays in living cells), or 6-well plates at a density of 1,000,000 cells per well (for BRET assays on membrane preparations).

BRET assays in living cells. Cells seeded in 96-well plates were washed twice with Phosphate Buffered Saline (PBS), followed by Tyrode buffer addition (composition: 137 mM NaCl, 0.9 mM KCl, 1 mM $MgCl_2$, 11.9 mM $NaHCO_3$, 3.6 mM $NaH_2PO_4$, 25 mM HEPES, 5.5 mM Glucose and 1 mM $CaCl_2$, pH 7.4). The cells were then treated with the different ligands or vehicle for the indicated times. The Rluc substrate, coelenterazine 400a, was added at a final concentration of 2.5 µM and cells were further incubated for an additional 5 minutes. BRET values were then collected using a Mithras™ LB940 Multimode Microplate Reader or a TRISTAR® LB942 Multimode Microplate Reader, equipped with the following filters: 400 nm±70 nm (energy donor) and 515 nm±20 nm (energy acceptor). BRET values were determined by calculating the ratio of the light emitted by GFP (515 nm) over the light emitted by the Rluc (400 nm). To determine the % of activation (Stim as % of basal), BRET values obtained for the agonist treated cells where expressed as a percentage of the BRET values obtained with the corresponding cells treated with vehicle.

BRET assays for GRK2-GFP translocation to RlucII-tagged receptor (FIGS. 15B and 15C): 100 ng of HA-TPαR-RlucII, 750 ng of GRK2-GFP10 (WT in FIG. 15B or D110A mutant in FIG. 15C), 100 ng of the indicated Gα, 100 ng of WT Gβ1 and 100 ng of WT Gγ5 and PEI at a ratio of PEI:DNA of 3:1, is added to a suspension of HEK293SL (350,000 cells/ml). Cells were seeded (100 µl of cells/PEI/DNA suspension per well of a 96-well plate) on poly-D-lysine pretreated plates. 48 h post-transfection, cells were washed and preincubated in Tyrode+1 mM $CaCl_2$ at 37° C. for 60 min. Cells were exposed for a total of 15 min to different doses of U-46619 in FIGS. 15B and 15C, at 37° C. Coelenterazine 400a was then added at a final concentration of 2.5 µM within the last 5 min of stimulation. BRET was measured at 37° C., using a Tristar® Microplate Reader (Berthold Technologies®).

BRET assays for RlucII-GRK2 translocation to the plasma-membrane labeled with rGFP-CAAX (Kras) (FIGS. 16B and 16C): 100 ng of HA-TPαR, 20 ng of RlucII-GRK2, 100 ng of the indicated Gα, 100 ng of WT Gβ1, 100 ng of WT Gγ5, 400 ng of rGFP-CAAX (Kras), 180 ng of ssDNA, and PEI at a ratio of PEI:DNA of 3:1, is added to a suspension of HEK293SL (350,000 cells/ml). Cells were seeded (100 µl of cells/PEI/DNA suspension per well of a 96-well plate) on poly-D-lysine pretreated plates. 48 h post-transfection, cells were washed and preincubated in Tyrode+1 mM $CaCl_2$ at 37° C. for 60 min. Cells were exposed for a total of 15 min to different doses of U-46619 in FIG. 16B or for Z' Factor determination (FIG. 16C) to either vehicle or 100 nM U46619 was added to the wells of half of a 96-well plate, at 37° C. Coelenterazine 400a was then added at a final concentration of 2.5 µM within the last 5 min of stimulation. BRET was measured at 37° C., using a Tristar® Microplate Reader (Berthold Technologies). Z' Factor determination was obtained as described previously.

G-protein inhibitors. BRET assays were performed as described previously, except that cells were pre-treated overnight at 37° C. with 100 ng/ml of pertussis toxin, or, for 20 minutes at 37° C. with 100 nM of Ubo-Qic.

Kinetics experiments. BRET assays were performed as described previously, except that BRET readings were collected at regular intervals, 5 min after coelenterazine addition, while ligands and vehicle were injected to the cells after 30 sec of BRET measurements.

Z'-factor determination. HEK293 cells were transfected as described with the indicated constructs (see description of FIGS. 7A, 7B, 9A, 10C, 11D and 16C). BRET assays were performed as described previously, with half of the 96-well plate treated with the indicated agonists and the second half of the plate treated with the corresponding vehicle. Z'-factor were calculated as described by Zhang et al. (Zhang, Chung et al. 1999). A Z'-factor between 0.4 and 1 is considered a robust assay.

Protein complementation assays using RlucII fragments. Cells were washed twice with PBS, followed by Tyrode buffer addition. The cells were then pre-treated with the Rluc substrate, coelenterazine 400a, at a final concentration of 2.5 µM for 30 min at 37° C. The different ligands or vehicle were added for an additional 10 min. Luminescence values were then collected using a Mithras™ LB940 Multimode Microplate Reader, without any filters.

BRET assays on membrane preparations. Cells seeded in 6-well plates were collected, re-suspended in lysis buffer (composition: 25 mM Tris-HCl pH 7.4, 2 mM EDTA, 5 mM $MgCl_2$, 27% sucrose, 15 µM GDP, 2 µM GTP, 10 µg/ml benzamidine, 5 µg/ml soybean trypsin inhibitor and 5 µg/ml leupeptin) and subjected to a polytron homogenization. Following centrifugation steps, the membrane pellets were resuspended in Tyrode buffer supplemented with 5 mM $MgCl_2$, 15 µM GDP and 15 µM GTP. BRET experiments were then performed as described previously, using 400 µg of membrane per well.

Figure 2C:
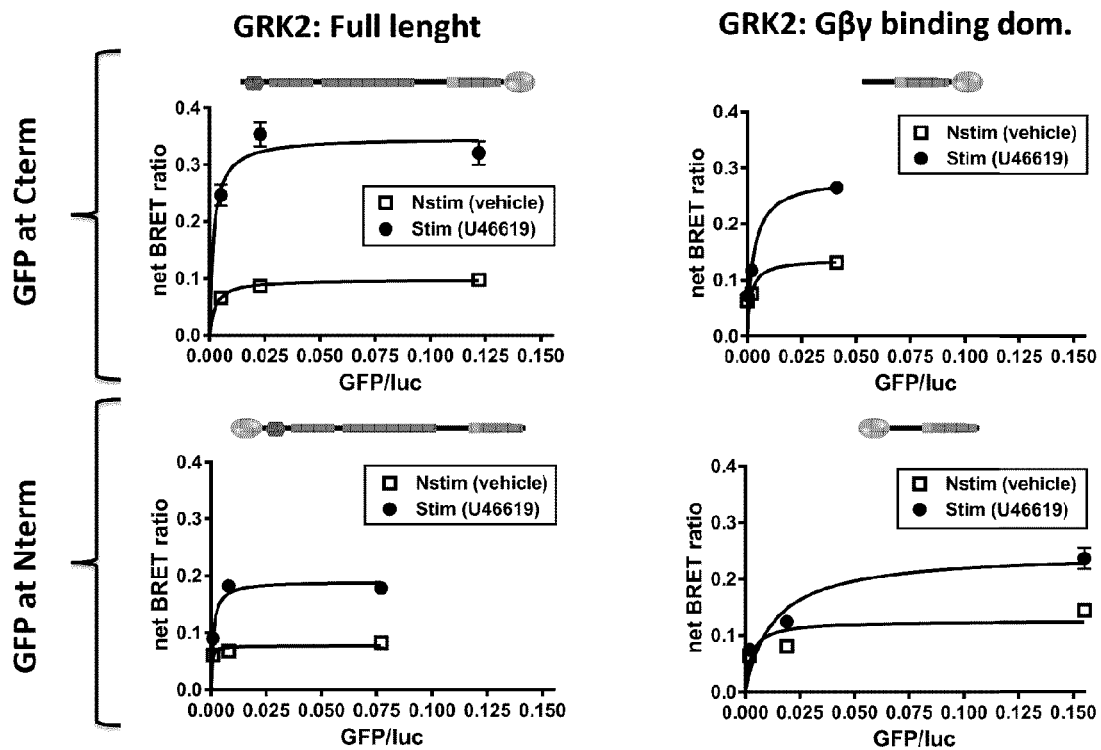

BRET Titrations (in FIGS. 2B and 2C): HEK293 cells were transiently transfected using PEI in a µg DNA to µl PEI 1 mg/ml ratio equal to 1µg:3p1. The DNA transfected per well of a 96-well plate is as follows: In FIGS. 2A and 2B: 40 ng of HA-TPαR or HA-β1AR, 0.5 ng of RlucII-Gγ5, 10 ng $Gα_{11}$ or $Gα_{15}$, 10 ng Gβ1 encoding constructs and an increasing quantity of GRK2 constructs tagged with GFP10, up to 75 ng. The BRET assay was performed 2 days post-transfection; cells were washed once with PBS and left in Tyrode's buffer. The cells were treated with vehicle or agonist drug, 100 nM U-46619 (FIG. 2B) or 1 µM isoproterenol (FIG. 2A) for a total of 15 min at RT. The Rluc substrate Coel-400a was then added at a final concentration of 2.5 µM within the last 5 min of stimulation. BRET values were then collected using a Mithras® LB940 Multimode Microplate Reader, and determined by calculating the ratio of the light emitted by the acceptor over the light emitted by the RlucII. The titration curves (FIGS. 2B and 2C) represent the BRET ratios obtained in function of GFP-construct expression (evaluated in fluorescence) over RlucII construct expression (evaluated in bioluminescence).

EXAMPLE 2

Results

Figure 1B:
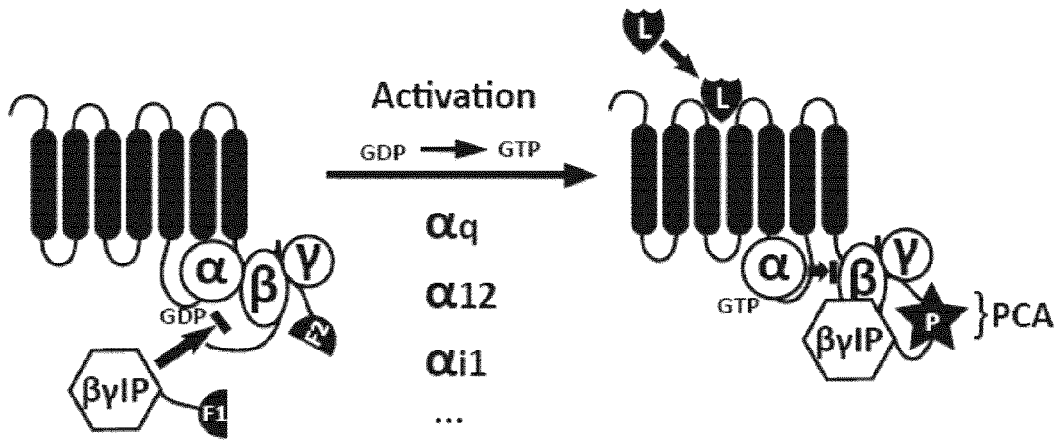

To study the activation of specific G-proteins by GPCRs, an assay was developed based on the competition between Gα subunits and βγIP for their binding to Gβγ subunits. As depicted in FIGS. 1A and 1B, in the absence of receptor activation, the Gα subunit is tightly bound to the Gβγ dimer, preventing its association with the βγIP. Following receptor stimulation, the GTP-bound Gα dissociates from the Gβγ complex, which is then free to interact with the βγIP. The interaction between the βγIP and the Gβγ, therefore, reflects the G-protein activation. By co-expressing βγIP and Gβγ, each tagged with one of the two components of the detection system, with different subtypes of untagged Gα, it has been possible to determine the coupling profile of a given receptor following its activation. As shows below, different methods of detection may be used to assess the interaction between the βγIP and the Gβγ, such as resonance energy transfer (RET) approaches (FIG. 1A: bioluminescence (BRET) or fluorescence resonance energy transfer (FRET)); or FIG. 1B: protein complementation (PC) assays.

Figure 1C:
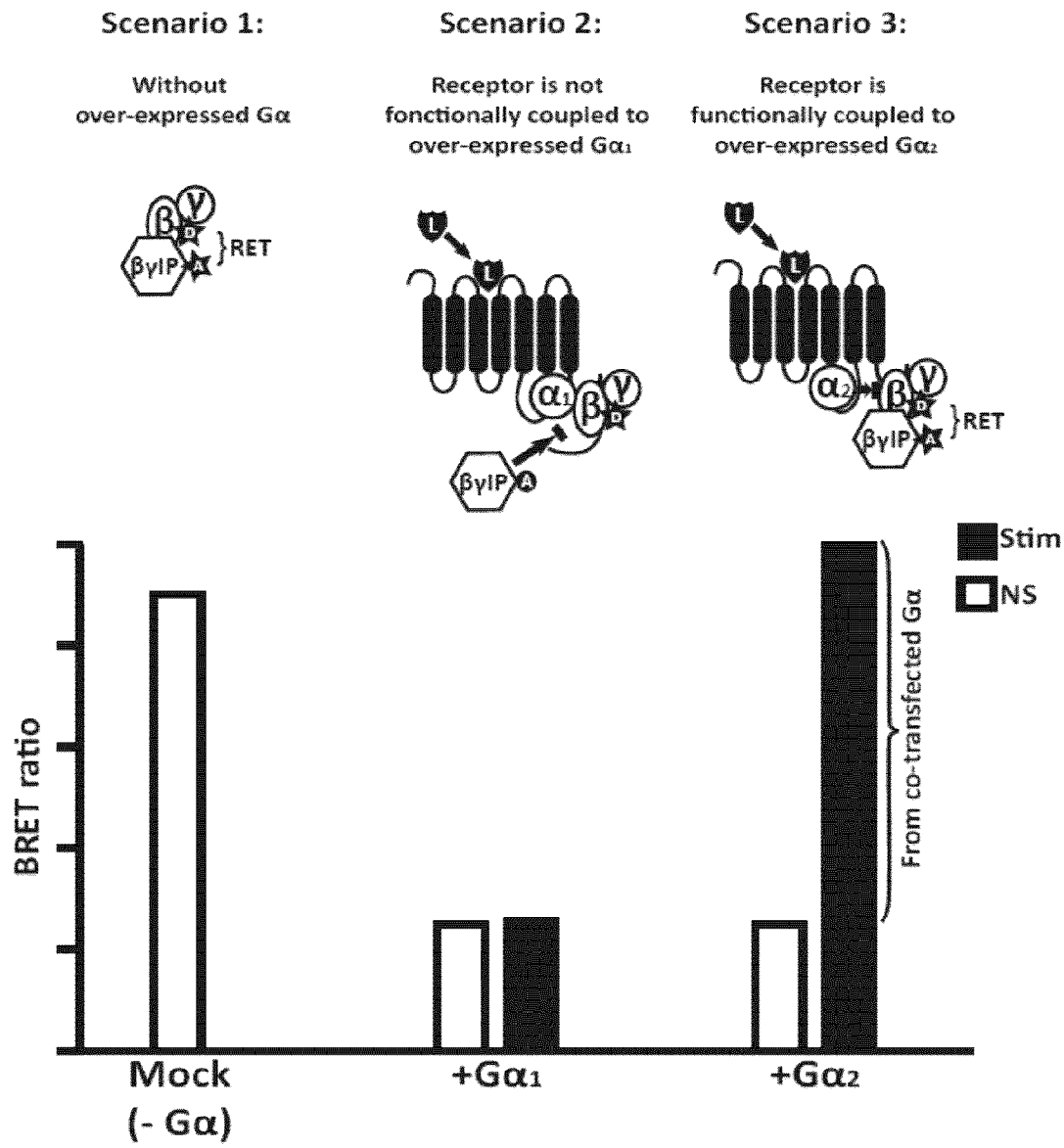

Taking RET as an example of detection method, possible scenarios and corresponding results interpretation for βγIP-based biosensors of G-protein activation are shown in FIG. 1C. In the absence of any Gα subunit co-transfected with the two RET partners βγIP-A and Gβγ-D, the basal RET signal is relatively high due to the constitutive interaction between βγIP and Gβγ dimer. In that case, a modulation of the RET signal measured following receptor stimulation would reflect the activation of endogenous Gα subunits (Mock or −Gα condition). Co-expression of a Gα subunit prevents the basal interaction between βγIP-A and Gβγ-D, leading to a decrease in the basal RET response recorded (white bars in +Gα$_1$ and +Gα$_2$ conditions). Upon stimulation of the receptor (with a suitable GPCR ligand, for example), significant increase in the modulation of the RET signal as compared to the mock condition is observed only if the receptor engages (i.e. is coupled to) the specific Gα subunit co-expressed with the other biosensor components (black bar, +Gα$_2$ conditions). However, if the over-expressed Gα subunit is not functionally coupled to the receptor, no significant change in the BRET signal is detected upon receptor stimulation (black bar, +Gα$_1$ conditions).

FIGS. 2A to 2C present some of the different constructs tested for optimization of the βγIP-based G-protein activation biosensor. Four different GFP-tagged constructs for GRK2 and 3 were tested, two based on the complete GRK coding sequence and two on the C-terminal PH domain/Gβ binding domain, with GFP at either the N-terminal or the C-terminal portion of GRK (FIG. 2A). The results presented in FIGS. 2B and 2C indicate that all GRK2 configurations/constructs gave a detectable BRET response (and thus may be used in the biosensor), and that the full-length GRK2 tagged at its C-terminal with a BRET acceptor (e.g., GFP) is giving the best dynamic window in term of amplitude of BRET signal and stability of response over a wider range of donor to acceptor ratios. Similar results were obtained using GFP-tagged GRK3 constructs.

Figure 3A:
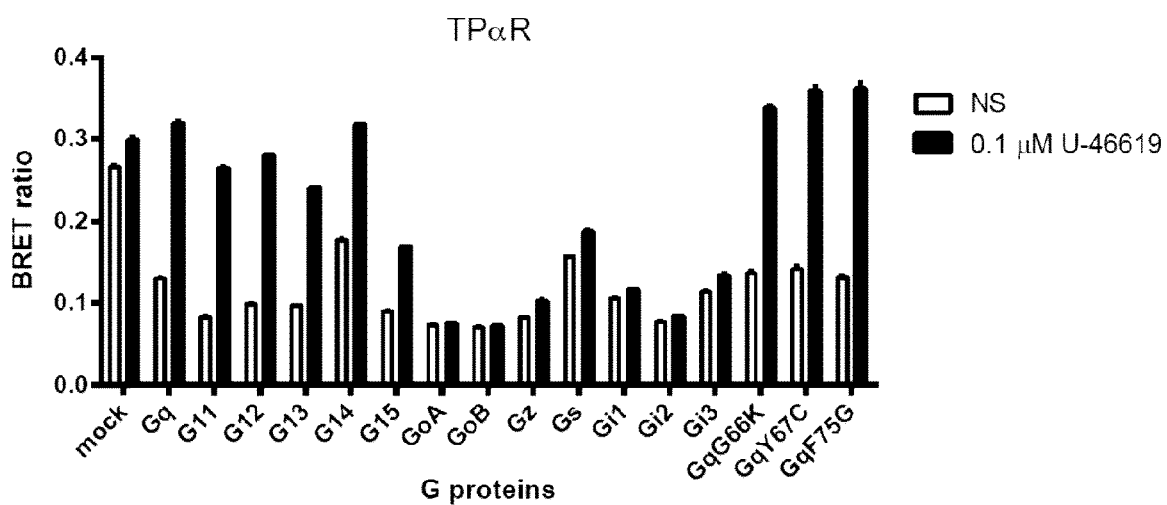
FIGS. 3A to 3C show the G-protein activation profile of TPαR using a βγIP-based biosensor.
Figure 3B:
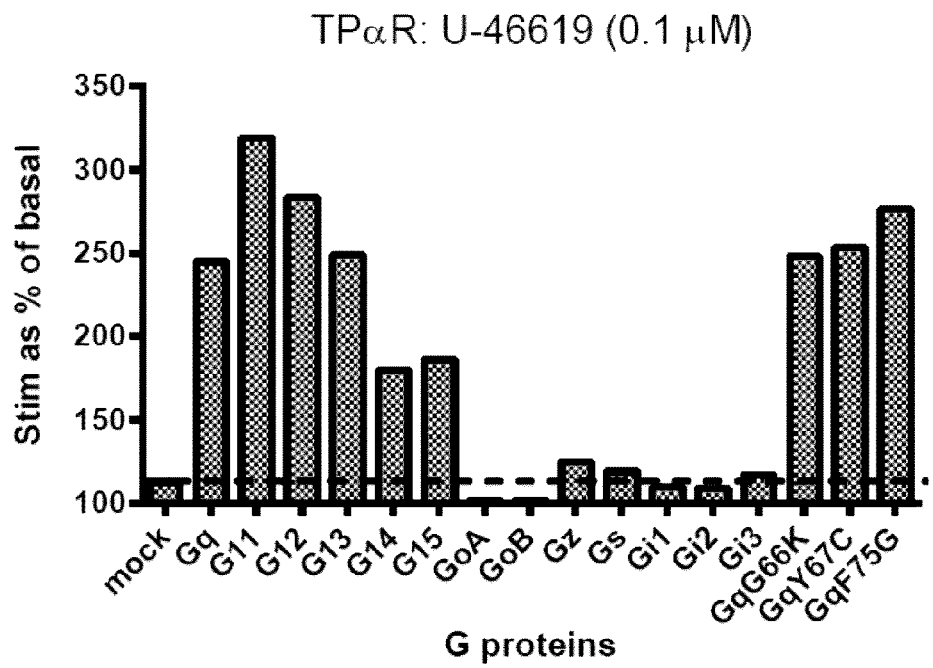

To assess the feasibility of using a βγIP to monitor G-protein activation, the GRK2 protein, which specifically interacts with free Gβγ dimers, was selected as a representative βγIP, and tagged at its C-terminus with the energy acceptor GFP10 (GFP), thus allowing the use of BRET as a readout of its interaction with Gβγ. The GRK2-GFP fusion protein was co-expressed with a Gγ5 subunit tagged in N-terminus with the energy donor Renilla luciferase (Rluc), as well as with untagged Gβ1 and Gα subunits. In addition to the biosensor components (GRK2-GFP and Rluc-Gγ5), Gβ1 and various Gα, cells were co-transfected with the thromboxane A2 receptor (TPαR), which was chosen as an example of a prototypical GPCR. In the experiment depicted in FIG. 3A, the G-protein coupling profile of the TPαR was determined by stimulating cells co-expressing the different Gα proteins, Gα$_q$, Gα$_{11}$, Gα$_{12}$, Gα$_{13}$, Gα$_{14}$, Gα$_{15}$, Gα$_{oA}$, Gα$_{oB}$, Gα$_z$, Gα$_s$, Gα$_{i1}$, Gα$_{i2}$ and Gα$_{i3}$, with the TPαR agonist U-46619 (a stable synthetic analog of the endoperoxide prostaglandin PGH2), and compared with results obtained in absence of Gα over-expression (mock condition, left bars). In the absence of Gα co-transfection, the BRET signal recorded was relatively high and only slightly modulated upon stimulation with U-46619, reflecting activation of endogenous Gα proteins. Upon co-expression of specific Gα proteins, an agonist-induced modulation of the BRET signal was significantly higher in cells over-expressing Gα$_q$, Gα$_{11}$, Gα$_{12}$, Gα$_{13}$, Gα$_{14}$ and Gα$_{15/16}$, relative to the mock condition or to cells over-expressing Gα subunits of the Gα$_i$ family, indicating that TPαR is coupled to the activation of G-proteins of the Gα$_q$ and Gα$_{12}$ families, but not of those of the Gα$_i$ family (FIG. 3B).

Figure 3C:
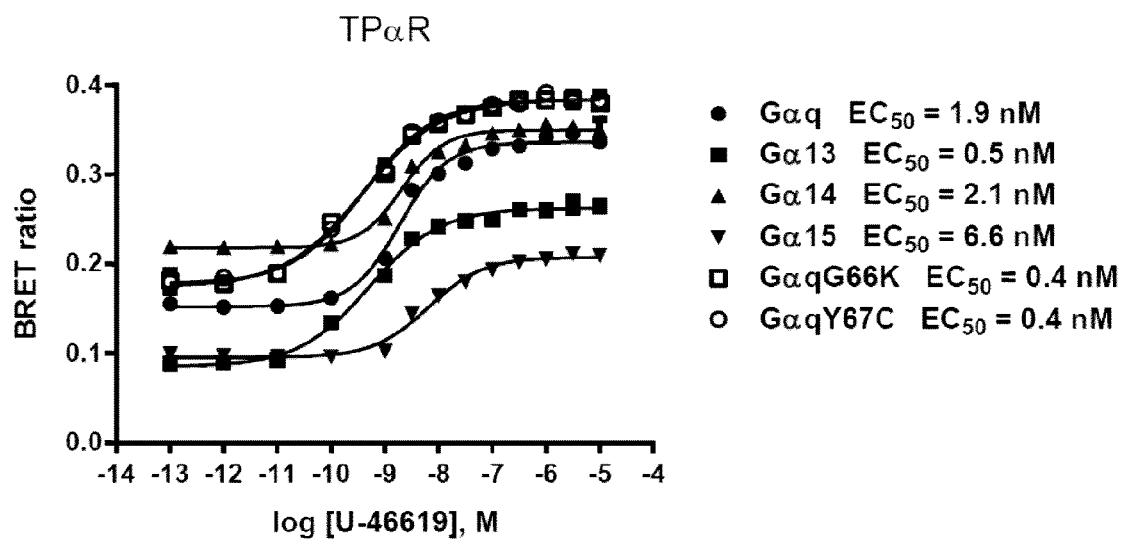

In addition to the wild-type (native) Gα proteins, three Gα$_q$ mutants (Gα$_q$G66K, Gα$_q$Y67C and Gα$_q$F75G, were also used in the panel of G-proteins tested with the TPαR. The substitution of the glycine residue at position 66 of the Gα$_q$ protein for a charged residue (GqG66K for example), had been previously described as resulting in Gα$_q$ protein mutants with promiscuous coupling properties, as they can also be activated by non-Gα$_q$-coupled receptors (Heydorn, Ward et al. 2004). As can be seen on FIGS. 3A and 3B, the previously described Gα$_q$G66K mutant, as well as the novel Gα$_q$Y67C and Gα$_q$F75G described herein, were activated by the TPαR. These promiscuous Gα proteins (or any Gα proteins having equivalent mutations at these positions, see FIG. 14) may be used as positive controls for GPCR activation in βγ-based biosensor assays and be particularly useful with receptors for which only limited information is available on their coupling preferences, such as orphan receptors. Gα$_q$, Gα$_{13}$, Gα$_{14}$, Gα$_{15/16}$, Gα$_q$G66K and Gα$_q$Y67C were then selected for dose-response curves of U-46619 (FIG. 3C). Interestingly, potencies ranging from 0.5 nM for Gβ to 6.6 nM for Gα$_{15/16}$ were measured, validating that βγIP-based biosensor assays can detect the specific potency of activation linked to each G-protein engaged by a given pair of receptor-ligand.

Figure 4A:
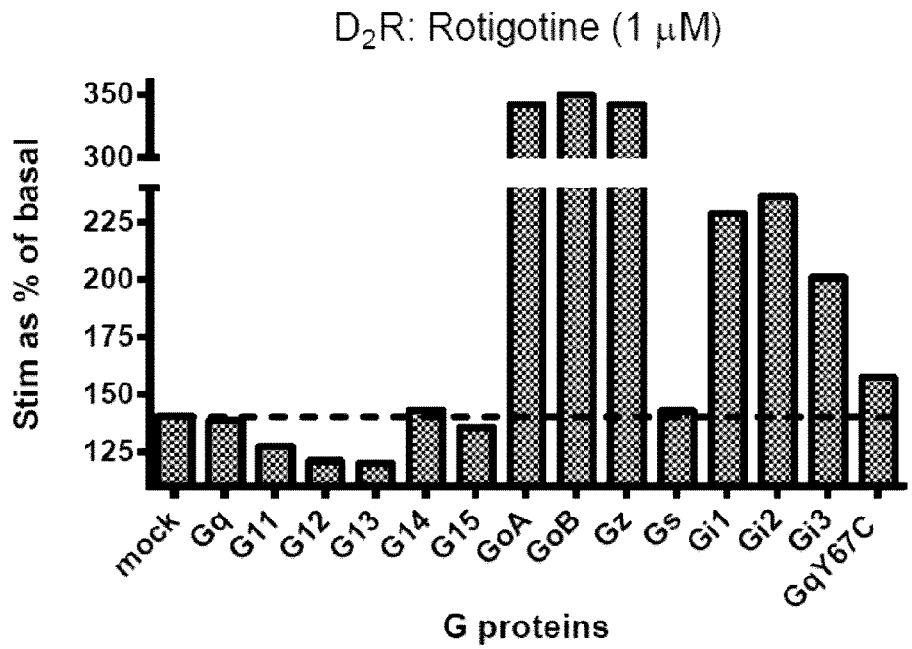
FIGS. 4A to 4J show the G-protein activation profiles for the dopamine D2 receptor (D$_2$R), the α$_{1B}$-adrenergic receptor (α$_{1B}$AR), and the α$_{2C}$-adrenergic receptor (α$_{2C}$AR) using a βγIP-based biosensor. HEK293 cells transiently expressing the D$_2$R (FIGS. 4A and 4B), α$_{1B}$AR (FIGS. 4C and 4D) or α$_{2D}$AR (FIGS. 4E and 4F) along with GRK2-GFP, Rluc-Gγ5, Gβ1 and the indicated Gα, were stimulated with the following agonists, rotigotine (FIGS. 4A and 4B), phenylepinephrine (FIGS. 4C, 4D, 4E) or epinephrine (FIG. 4E) for 15 min prior to BRET measurements.
Figure 4B:
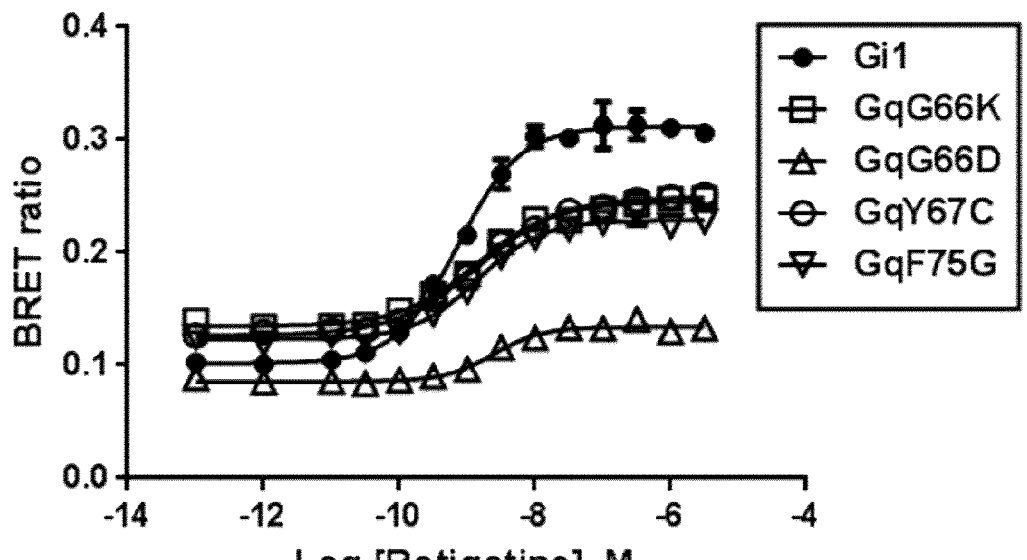
Figure 4C:
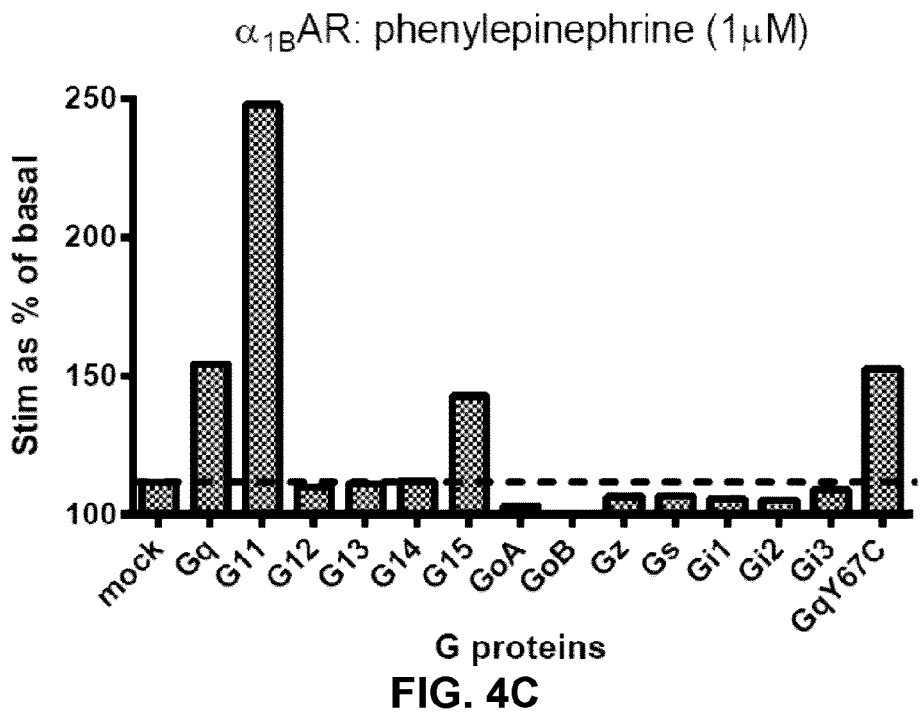
Figure 4D:
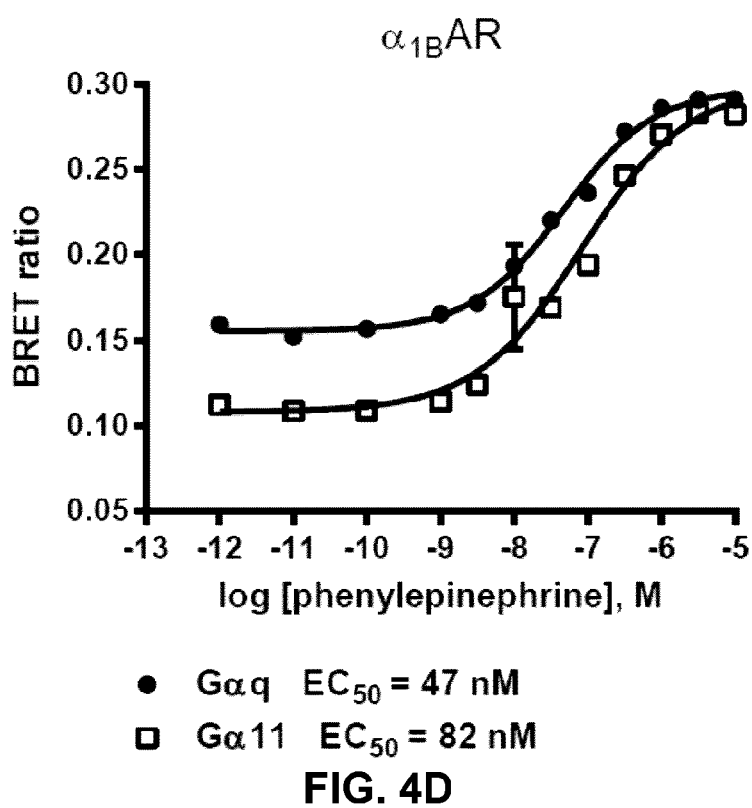
Figure 4E:
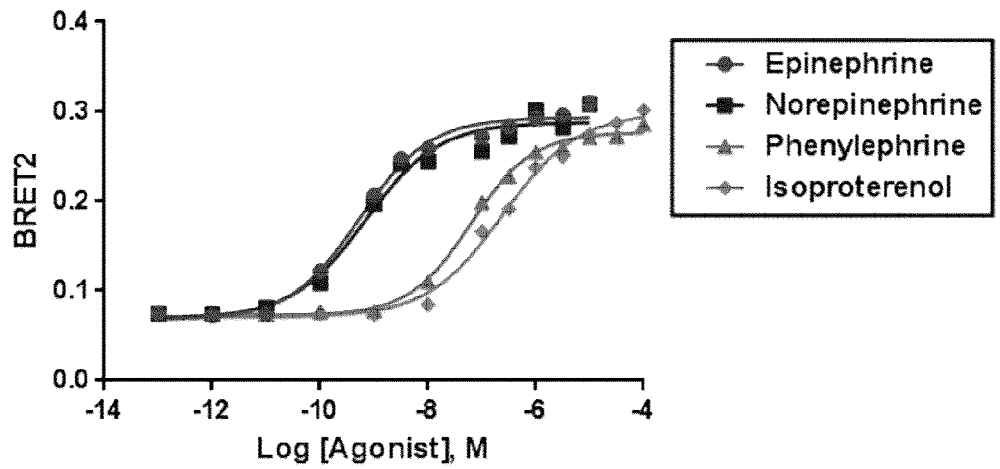
Figure 4F:
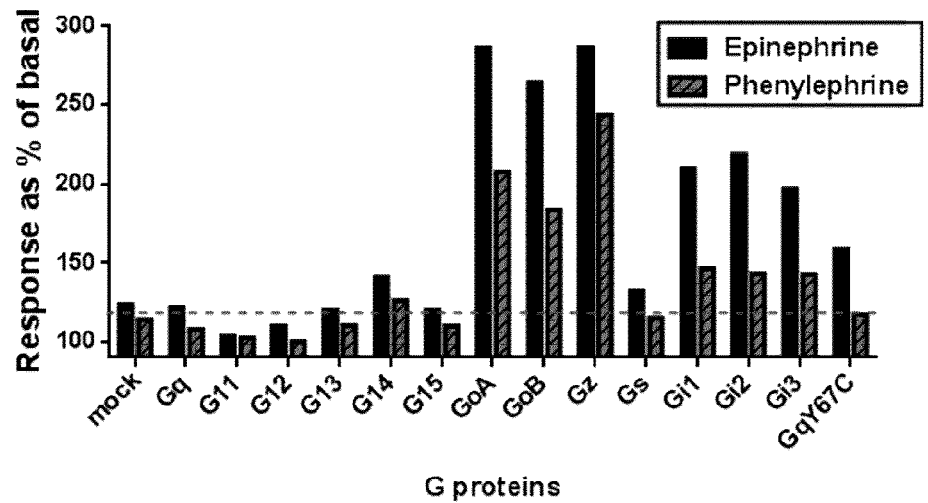
Figure 4G:
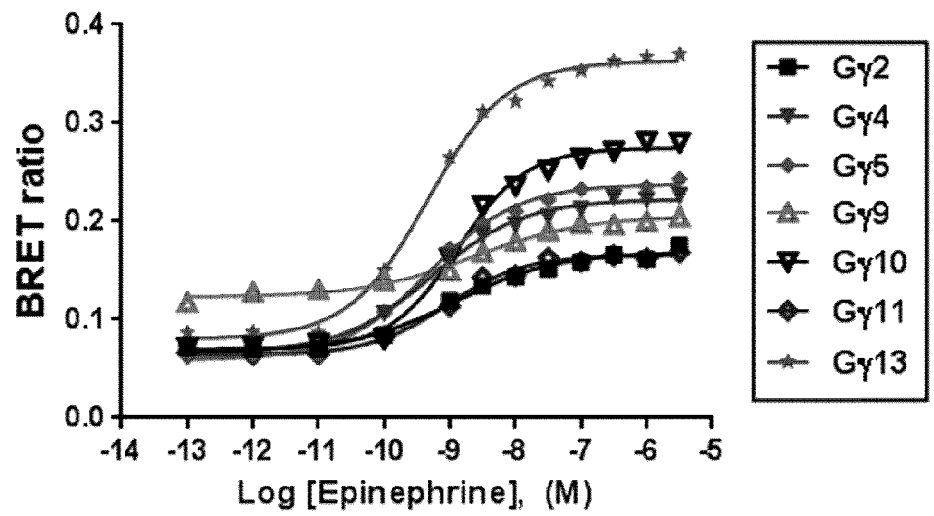
Figure 4H:
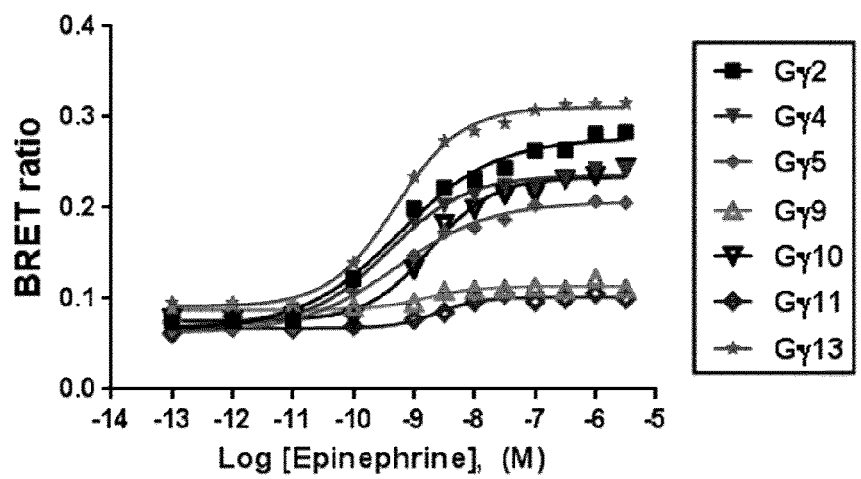
Figure 4I:
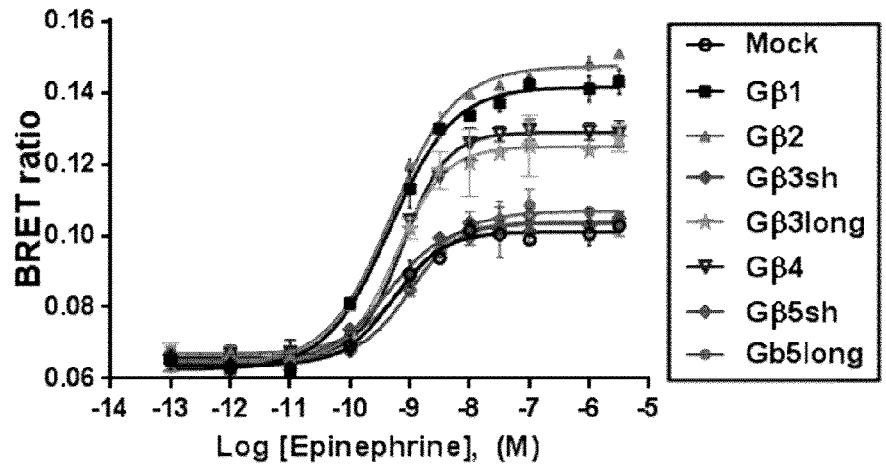
Figure 4J:
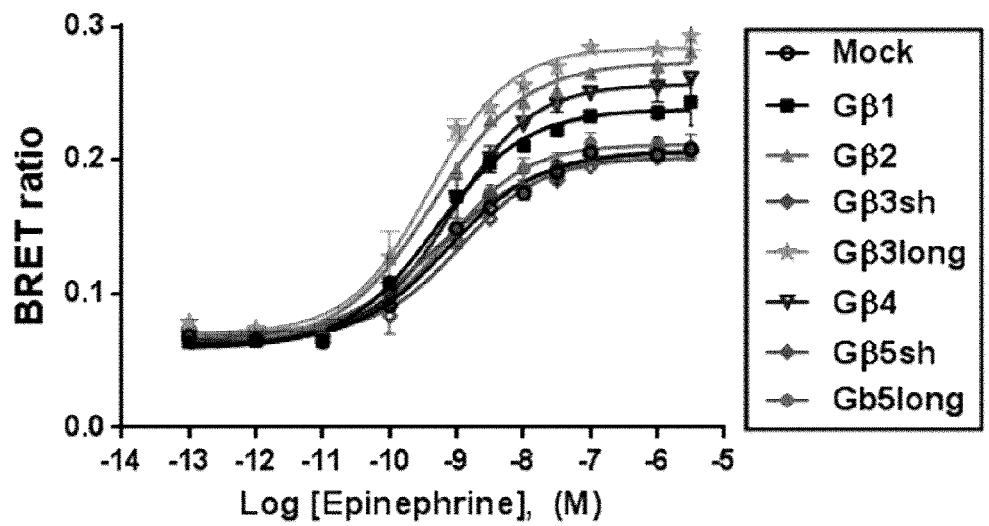

To further illustrate that a βγIP-based G-protein activation biosensor can be used to reveal the specificity of G-protein activation for different GPCRs, the dopamine D2 receptor (D$_2$R) and the α$_{1B}$-adrenergic receptor (α$_{1B}$AR) were each co-expressed with GRK2-GFP, Rluc-Gγ5, Gβ1 and various Gα, and stimulated with their prototypical agonists; rotigotine for D$_2$R, and phenylepinephrine for α$_{1B}$AR. As shown in FIGS. 4A and 4C, each receptor displays a specific G-protein activation profile, distinct from the one observed with TPαR (FIGS. 3A and 3B); D$_2$R is solely coupled to Gα$_i$-family members (Gα$_{oA}$, Gα$_{oB}$, Gα$_z$, Gα$_{i1}$, Gα$_{i2}$ and Gα$_{i3}$), while α$_{1B}$AR is exclusively coupled to Gα$_q$-family members (Gα$_q$, Gα$_{11}$ and Gα$_{15/16}$). The promiscuous Gα$_q$ mutant Gα$_q$Y67C was activated by the two receptors (FIGS. 4A and 4C). Dose-response curves were obtained with some of the G-proteins activated by D$_2$R (Gα$_{i1}$ and Gα$_q$Y67C) and α$_{1B}$AR (Gα$_q$ and Gα 11) (FIGS. 4B and 4D). In FIG. 4E, dose-response curves of Gα$_z$ activation were obtained for different adrenergic agonists: epinephrine, norepinephrine, phenylephrine and isoproterenol, from HEK293 cells expressing α$_{2C}$AR, Gα$_z$, GRK2-GFP, Rluc-Gγ5 and Gβ1. These results demonstrate that a βγIP-based G-protein activation biosensor may be used to establish G-protein preferences and activation/pharmalogical profiles of GPCRs, as well as a pharmacological tool to address potencies and efficacies of given ligands for activating various G-proteins through their cognate receptors. As shown in FIGS. 4F to 4J, distinct G-protein activation profiles were obtained with different combinations of Gβ and Gγ subunits. The results show that combinations of both Gβ and Gγ subunits can lead to distinct pharmalogical profiles of G-protein activation. These differences could, at least in part, be linked to distinct pharmalogical profiles observed with different cells and tissues expressing not only a specific set of Gα subunits but also different combination and levels of Gβ and Gγ subunits.

Figure 5A:
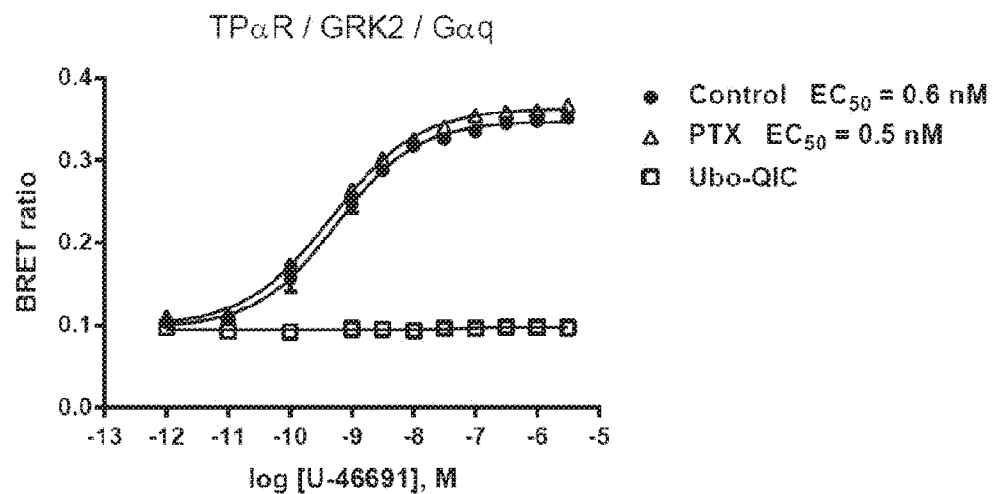
FIGS. 5A to 5D show that the βγIP-based biosensor can be used to characterize and validate G-protein modulators selectivity and mode of action.
Figure 5B:
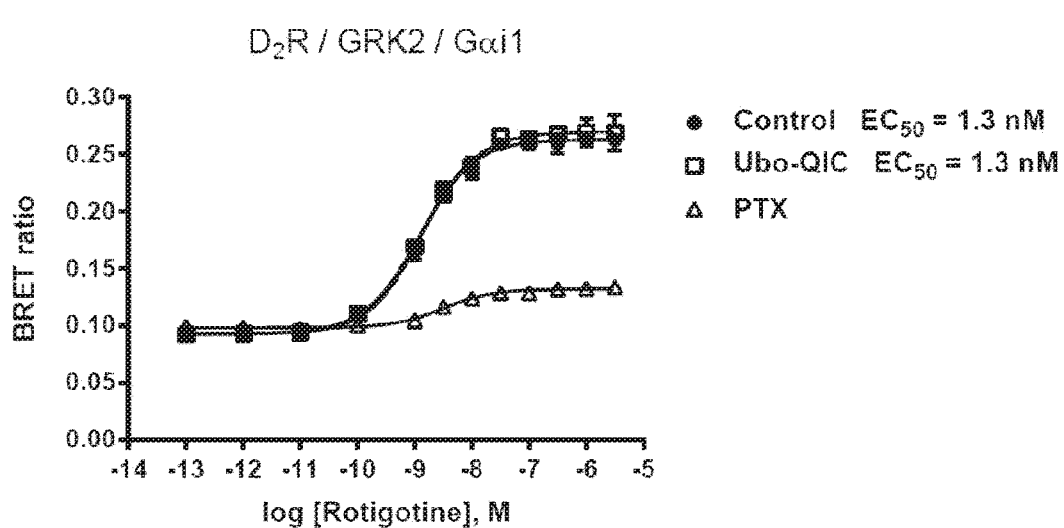
Figure 5C:
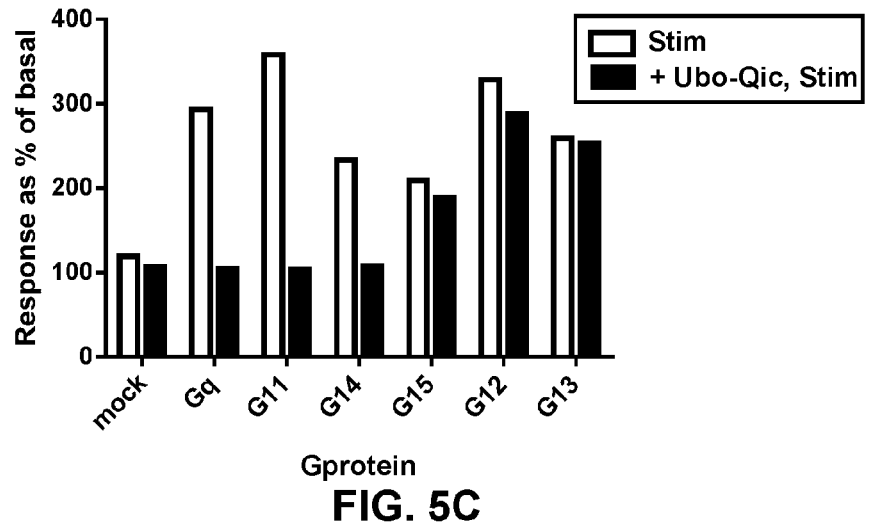
Figure 5D:
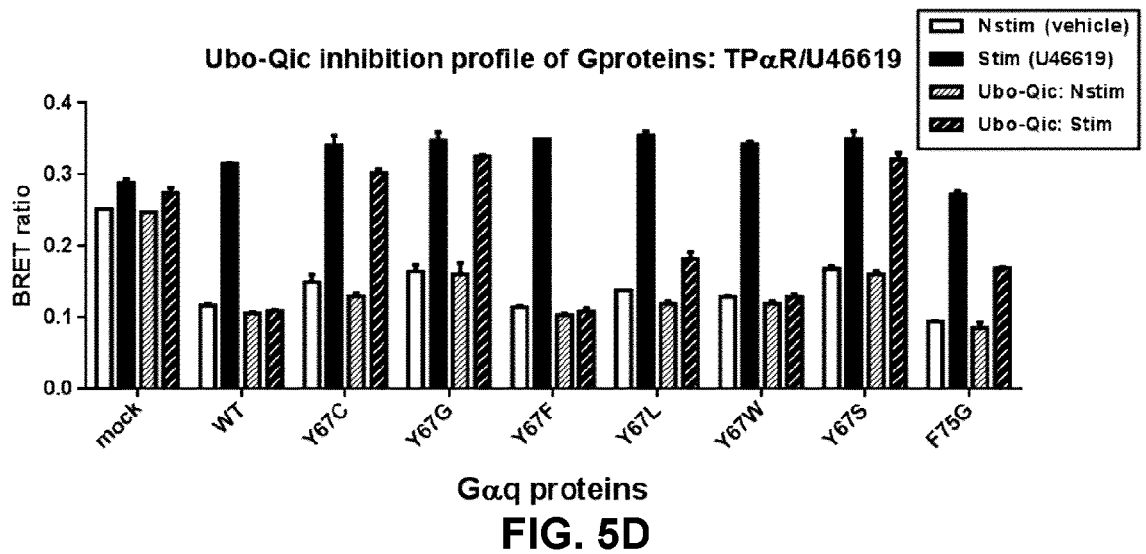

Inhibitors of G-protein activity such as *pertussis* toxin (PTX) and Ubo-Qic (structurally related to the cyclic depsipeptide YM-254890) which selectively blocks Gα$_i$ and Gα$_q$ activation, respectively, have been extensively used in the field of GPCRs to characterize the coupling properties of receptors (Takasaki, Saito et al. 2004). Using the βγIP-based G-protein activation biosensor, experiments were performed with those selective G-protein inhibitors to demonstrate the specificity of the BRET signals obtained. For the TPαR, which is coupled to Gα$_q$ activation, the BRET response measured using βγIP-based biosensor following agonist stimulation, was completely abolished upon Ubo-Qic pre-treatment, while PTX pre-treatment had no effect on this response (FIG. 5A). In contrast, for the Gα$_i$-coupled receptor D$_2$R, PTX pre-treatment significantly reduced the biosensor BRET response detected after agonist incubation, whereas pre-treatment with the Gq inhibitor Ubo-Qic had no detectable effect on the BRET signal recorded (FIG. 5B). TPαR-mediated G-protein activation was also used to validate Ubo-Qic inhibitor selectivity. The results presented in FIG. 5C show that, from the Gα$_q$ family (Gα$_q$, Gα$_{11}$, Gα$_{14}$ and Gα$_{15/16}$), only Gα$_{15/16}$ is insensitive to Ubo-Qic. The Gα$_{12}$ and Gα$_{13}$ proteins are also insensitive to Ubo-Qic. Finally, the βγIP-based biosensor was used to reveal the Ubo-Qic sensitivity of the activation of mutant Gα$_q$ (at position 67 or 75—see FIG. 14). Substitutions of the tyrosine residue at position 67 (Y67C, Y67G, Y67S & Y67L) led to resistance to Ubo-Qic and promiscuous properties, indicating that this residue may be important for controlling G-protein activation, and that the substitution of residue Phe75 to glycine (which is associated with a promiscuous phenotype—see FIG. 4A) led to a partial Ubo-Qic mediated inhibition of activation (FIG. 5D) Thus, in addition to validating the specificity of the BRET signals recorded for the various G-proteins, these results support the use of βγIP-based G-protein activation biosensors described herein as tools to identify/develop novel selective inhibitors of G-proteins.

Figure 6A:
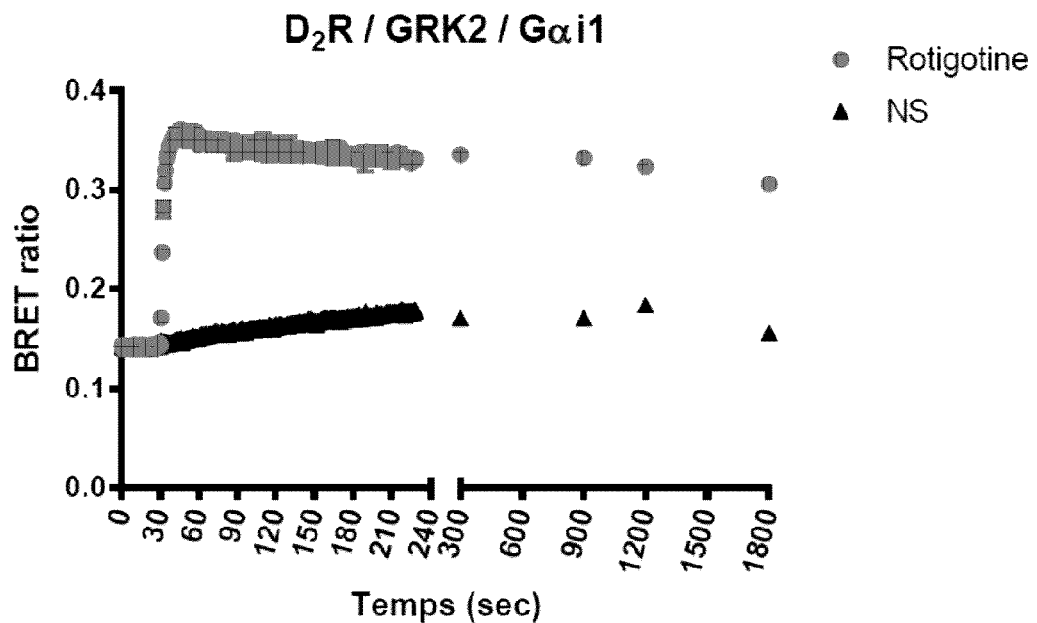
FIGS. 6A and 6B show the kinetics of the βγIP-based G-protein activation biosensor responses upon receptor activation.
Figure 6B:
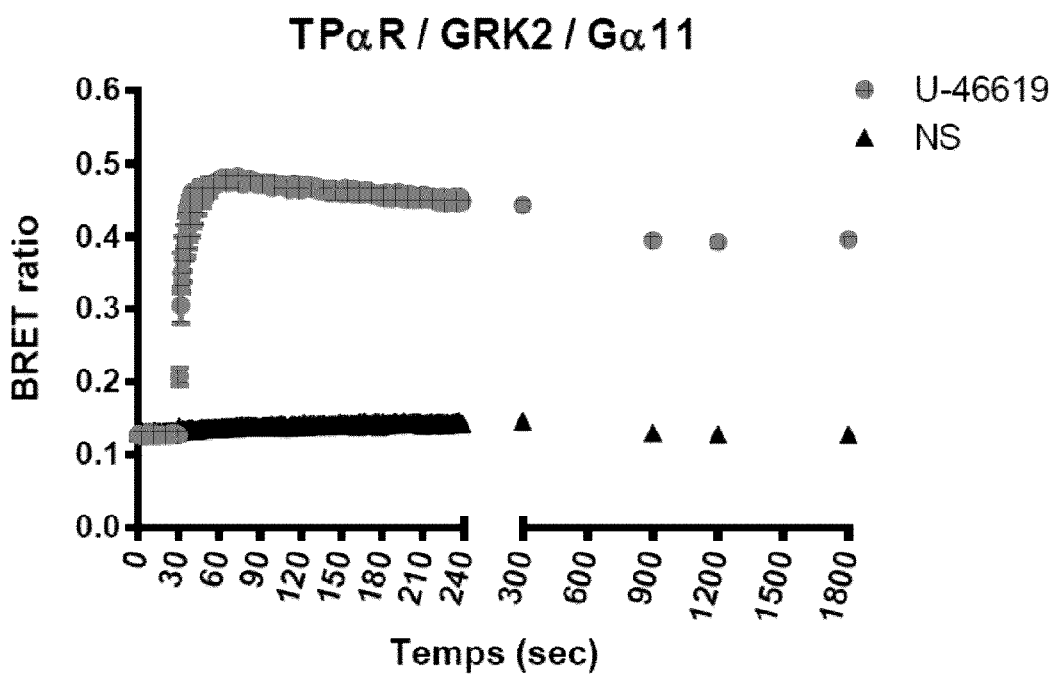
Figure 7A:
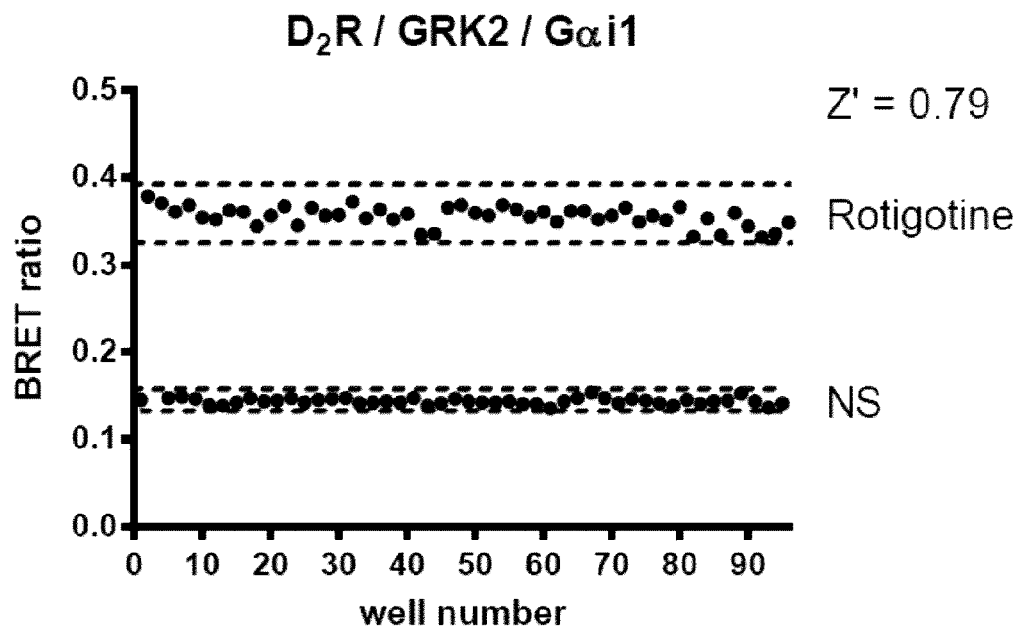
FIGS. 7A and 7B show the Z' factor evaluation for the βγIP-based G-protein activation biosensor. HEK293 cells transiently expressing the D$_2$R and Gα$_{i1}$ (FIG. 7A) or the TPαR and Gα$_{11}$ (FIG. 7B), along with Gβ1, Rluc-Gγ5 and GRK2-GFP were exposed to either 1 μM of rotigotine (FIG. 7A), 100 nM of U-46619 (FIG. 7B) or vehicle (FIGS. 7A, 7B) for 15 min. BRET ratios are represented for each individual well of a 96-well plate. Z' factor, for these representative experiments, were evaluated at 0.79 and 0.89 for D$_2$R (FIG. 7A) and TPαR (FIG. 7B), respectively.
Figure 7B:
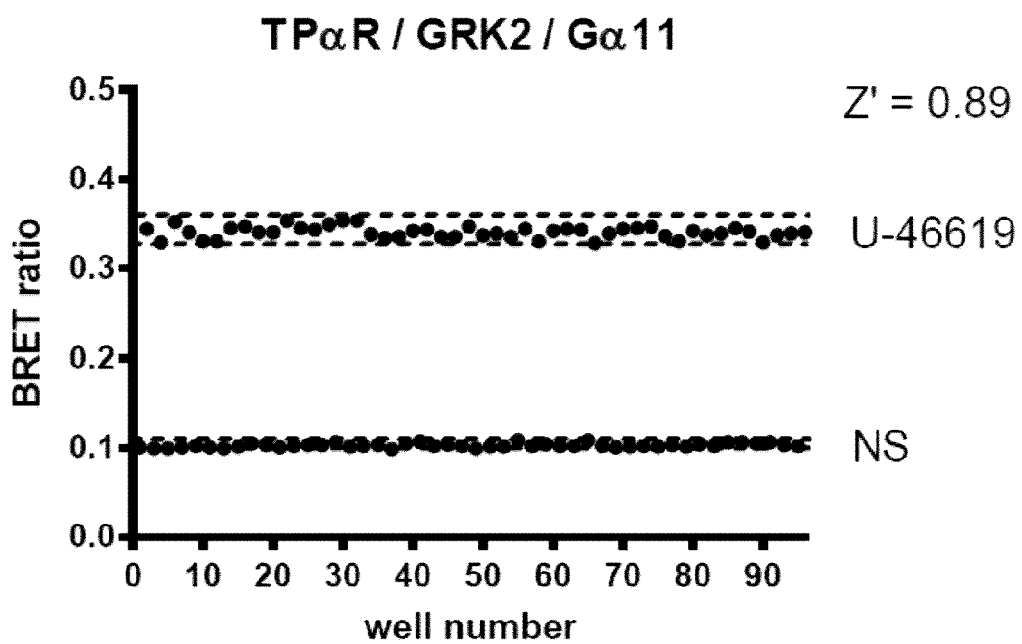

To further characterize the βγIP-based G-protein activation biosensor, kinetics of Gα$_{i1}$ (FIG. 6A) and Gα$_{11}$ (FIG. 6B) activation were determined following agonist treatment of D$_2$R and TPαR, respectively. As shown in FIGS. 6A and 6B, similar kinetics of activation were obtained for the two different receptors and G-proteins, with a maximal response reached approximately 30 seconds after ligand addition and a plateau lasting at least 30 minutes following the initial stimulation. This sustained response is particularly well suited for assay adaptation to high-throughput screening (HTS).

To evaluate the robustness of the assay, Z'-factors were determined for G-protein activation through typical Gα$_i$-(D$_2$R, FIG. 7A) and Gα$_q$-(TPαR, FIG. 7B) coupled receptors. The assay is particularly robust with Z'-factors of 0.79 and 0.89 for D$_2$R/Gα$_{i1}$ (FIG. 7A) and TPαR/Gα$_{11}$ (FIG. 7B), respectively. The robustness of this assay is compatible with the requirements of screening applications, notably HTS applications.

Figure 8A:
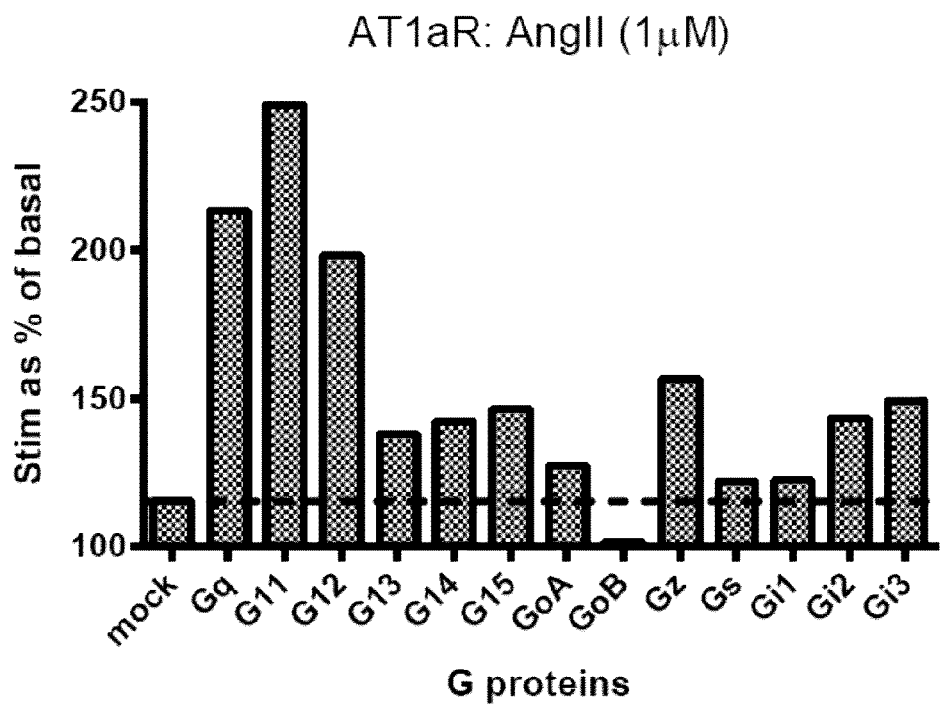
FIGS. 8A to 8C show a ligand profiling with the βγIP-based G-protein activation biosensor.
Figure 8B:
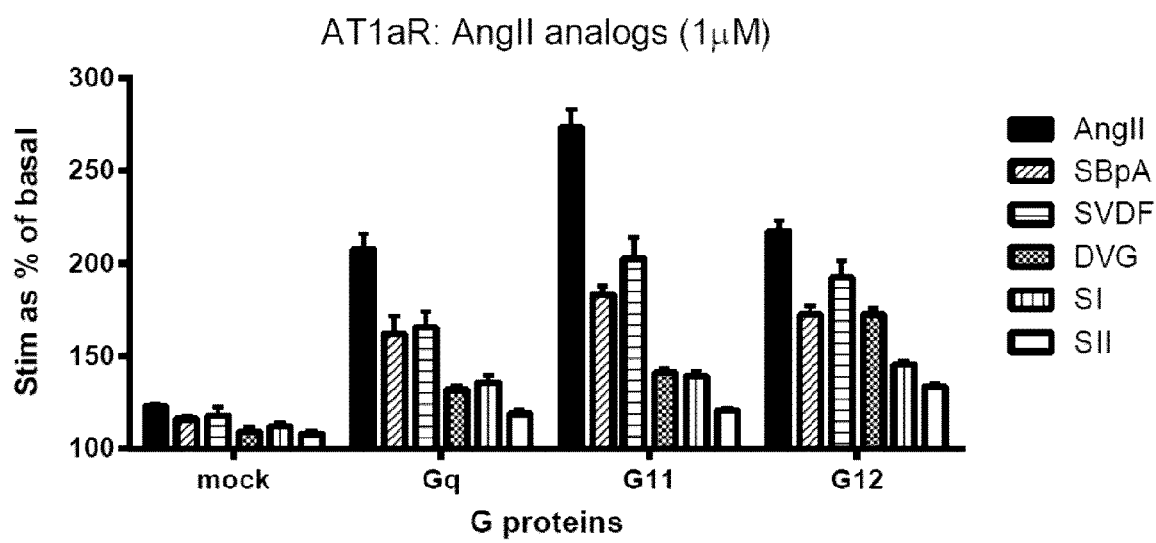
Figure 8C:
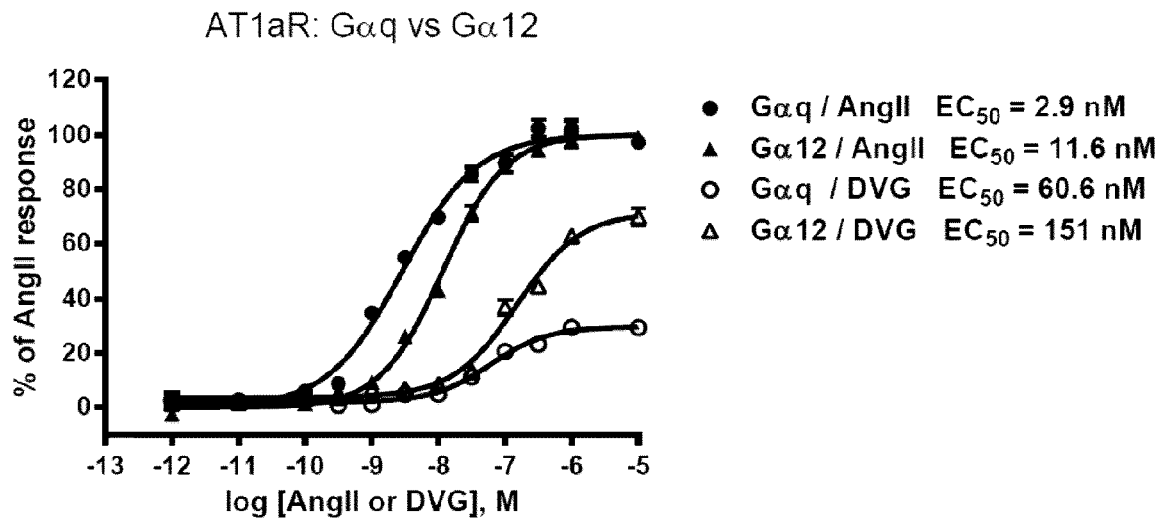

In addition to the previously described potential applications of the βγ-based biosensor in G-protein profiling of receptors and HTS, ligand characterization represents another application of this G-protein activation biosensor. GPCRs can preferentially engage different G-proteins and signaling pathways upon activation with different ligands, this phenomenon is known as ligand-biased signaling of GPCRs (Galandrin, Oligny-Longpre et al. 2007) (Kenakin and Christopoulos 2013). The biosensors described herein are particularly well suited for performing ligand profiling experiments since it is possible to assess the activity of all G-protein subtypes using the same RET partners. As a representative example, various ligands of the angiotensin II type 1 receptor (AT1R) were profiled using the βγIP-based G-protein activation biosensor (FIGS. 8A to 8C). A first set of experiments was performed to determine the coupling properties of the receptor using its natural ligand, angiotensin II. As shown in FIG. 8A, the AT1R is coupled to several members of the Gα$_q$-, Gα$_{12}$- and Gα$_i$-family of proteins. Gα$_q$, Gα$_{11}$ and Gα$_{12}$ were then selected for further characterization following activation of AT1R with different analogs of angiotensin II. As shown in FIGS. 8B and 8C, those angiotensin II derived-peptides stimulated the different G-proteins to various extents, revealing a potential bias of some ligands toward specific G-proteins. For example, the DVG peptide showed a better efficacy for Gα$_{12}$ activation than Gα$_q$, relative to angiotensin II response (FIG. 8C).

Figure 9A:
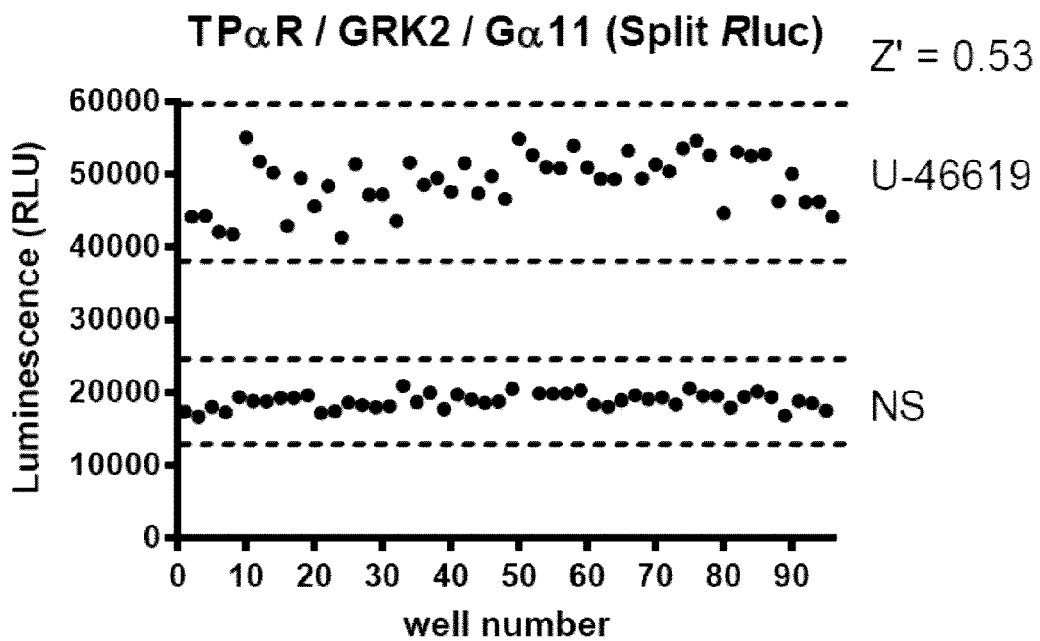
FIGS. 9A and 9B show the use of a protein complementation-based detection method to assess G-protein activation with the (βγIP-based biosensor; an Rluc protein complementation assay (Rluc-PCA).

It was next assessed whether protein complementation assay (PCA), instead of RET-based assays, may be used to assess the interaction between the βγIP and the Gβγ subunits (FIG. 1B). PCA, such as bimolecular fluorescence complementation (BiFC) or enzyme fragment complementation (EFC), allows the detection of interaction between two protein partners, which makes it compatible with the βγIP-based G-protein activation biosensor. To determine whether it is possible to use an EFC-based assay, and more particularly an Rluc-based EFC assay (Stefan, Aquin et al. 2007), in the βγIP-based G-protein activation biosensor, two fusion proteins were generated: GRK2 tagged with an N-terminal portion of Rluc in C-terminus (GRK2-Rluc F1), and the complementary C-terminal portion of Rluc in N-terminus of Gγ5 (Rluc F2-Gγ5). If an interaction between GRK2 and the free Gβγ subunits occurs (following G-protein activation), the two complementary Rluc fragments would re-associate and luminescence can be measured in presence of the RLuc substrate coelenterazine. A proof of concept was done using cells co-expressing TPαR with GRK2-Rluc F1, Rluc F2-Gγ5, Gβ1 and Gα$_{11}$. A robust luminescent signal was measured following stimulation with U-46619, revealing G11 protein activation, with a Z'-factor of 0.53 (FIG. 9A)

and an $EC_{50}$ of 8.4 nM (FIG. 9B), validating that PCA may be used in the βγIP-based G-protein activation biosensor described herein.

Figure 10A:
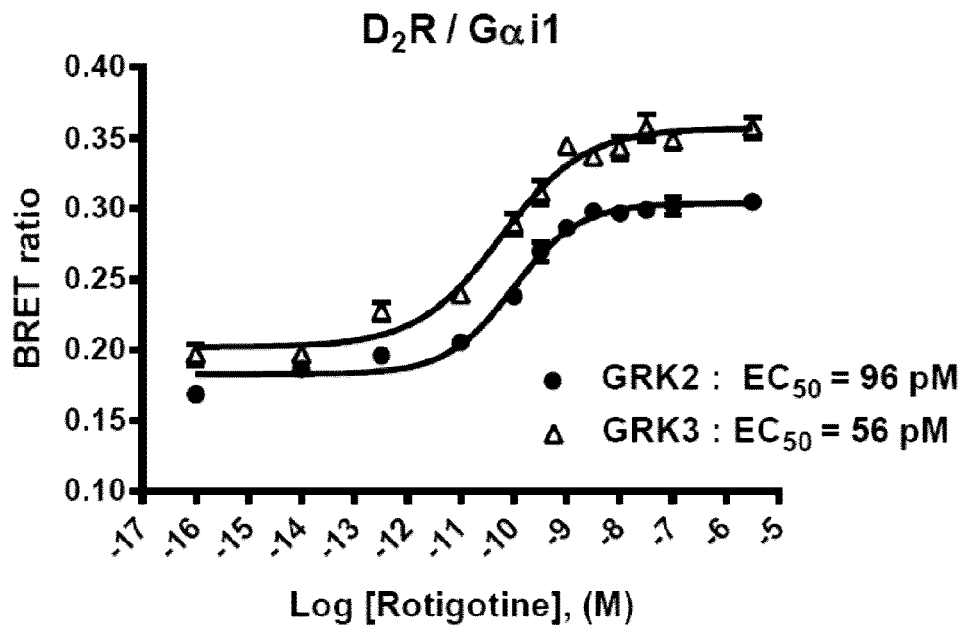
FIGS. 10A to 10C show the use of GRK3 as a βγIP to assess G-protein activation.
Figure 10B:
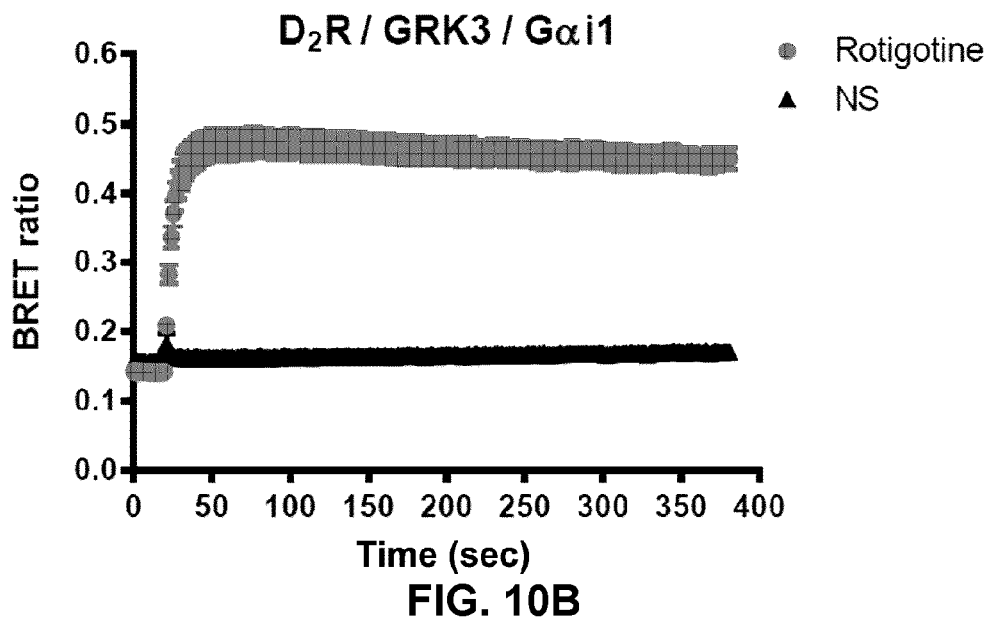
Figure 10C:
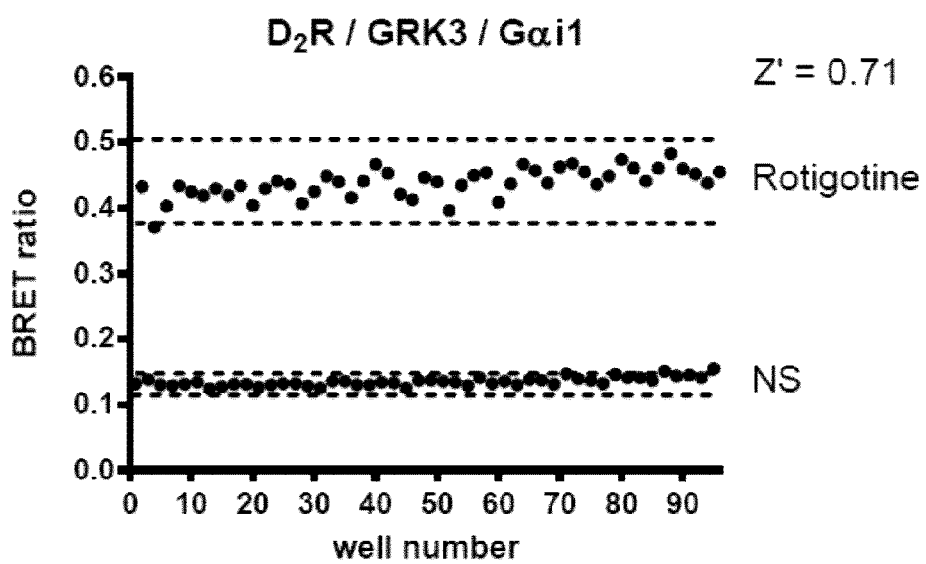

It was next assess whether βγIPs other than GRK2 (such as GRK3) could be used to monitor G-protein activation in the βγIP-based G-protein activation biosensor. A fusion protein was generated between GRK3 and the energy acceptor GFP, and the resulting GRK3-GFP was co-expressed with Rluc-Gγ5, Gβ1, Gα$_{i1}$ and the D$_2$R, to obtain dose-response curves of dopamine. As seen in FIG. 10A, similar potencies were observed using GRK2 or GRK3-based biosensors (96 pM for GRK2 and 56 pM for GRK3). The kinetics of activation of the GRK3-based biosensor were also similar to those obtained using the GRK2-based biosensor (FIGS. 6A and 6B), with a maximal response reached at approximately 30 seconds, and a plateau of at least several minutes (FIG. 10B). Finally, Z'-factor were also generated with the GRK3-based biosensor. Using the D$_2$R and Gα$_{i1}$, a Z'-factor of 0.71 was obtained with the GRK3-biosensor, confirming the robustness of the assay (FIG. 10C). Taken together, these data demonstrate that different βγIP can be used in the βγIP-based G-protein activation biosensor to assess G-protein activation.

Figure 9B:
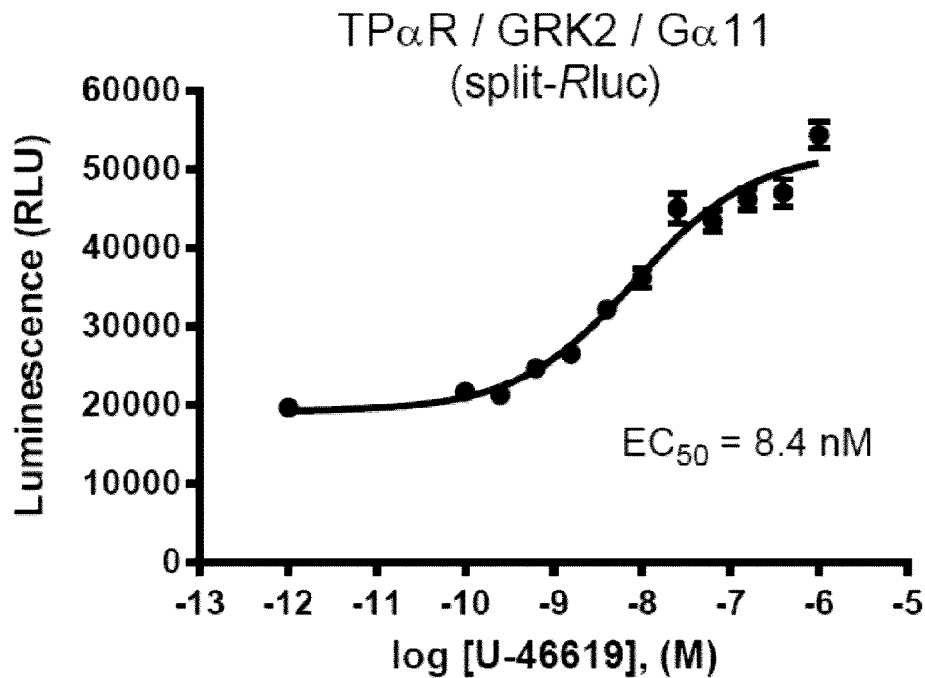
Figure 11B:
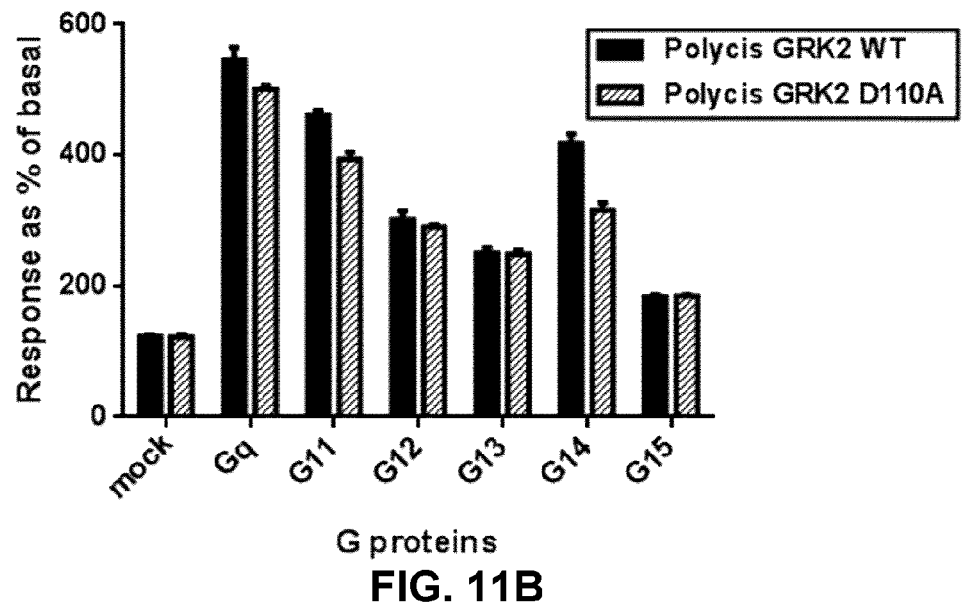
Figure 11C:
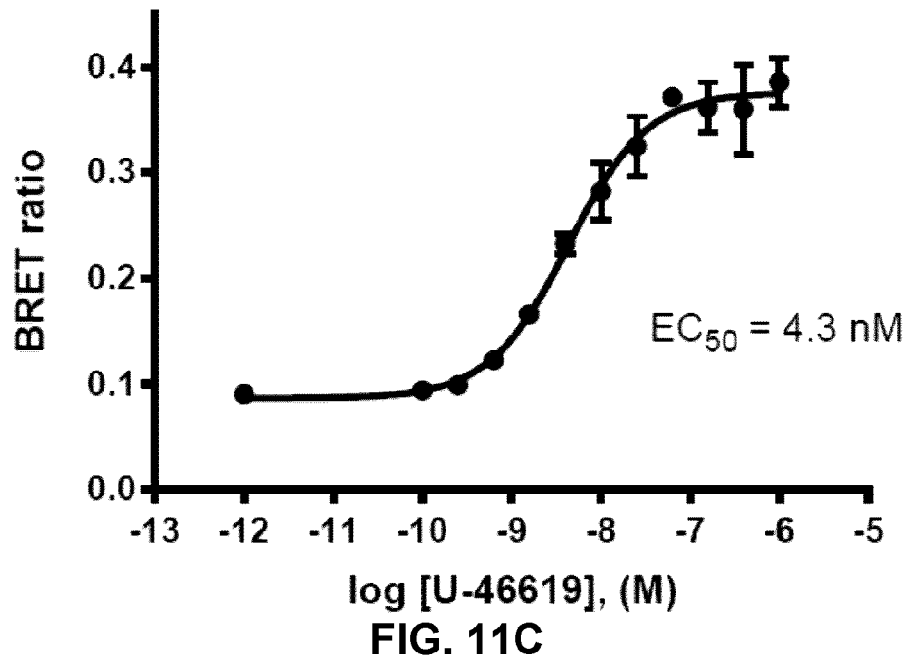

To simplify the use of the βγIP-based G-protein activation biosensor, a polycistronic vector encoding the GRK2-GFP, Rluc-Gγ5 and Gβ1 was developed (FIG. 11A). This ensures that the components of the biosensor are expressed from a single construct and at a fixed ratio, which could minimize inter-experiment variability. As shown in FIG. 11D, a Z'-factor of 0.8 was obtained using the polycistronic construct, co-transfected with plasmids encoding for TPαR and Gα$_{11}$. This result is comparable to the Z'-factor obtained with cells transfected with plasmids encoding individual biosensor components (FIG. 7B; Z'=0.89). Dose-response curve experiments were also performed using this polycistronic vector and an $EC_{50}$ value of 4.3 nM was obtained for the TPαR stimulated with U-46619 (FIG. 11C), similar to the $EC_{50}$ of 8.4 nM measured for the same receptor/ligand pair used with the Rluc-PCA based GRK2 biosensor (FIG. 9B). These results confirm the validity of expressing the different components of the biosensor in a polycistronic vector, which could be advantageously used to establish stable cell lines with only one selection marker, thus simplifying the experimental procedures and potentially improving reproducibility (e.g., minimizing inter-experiment variability).

Figure 12B:
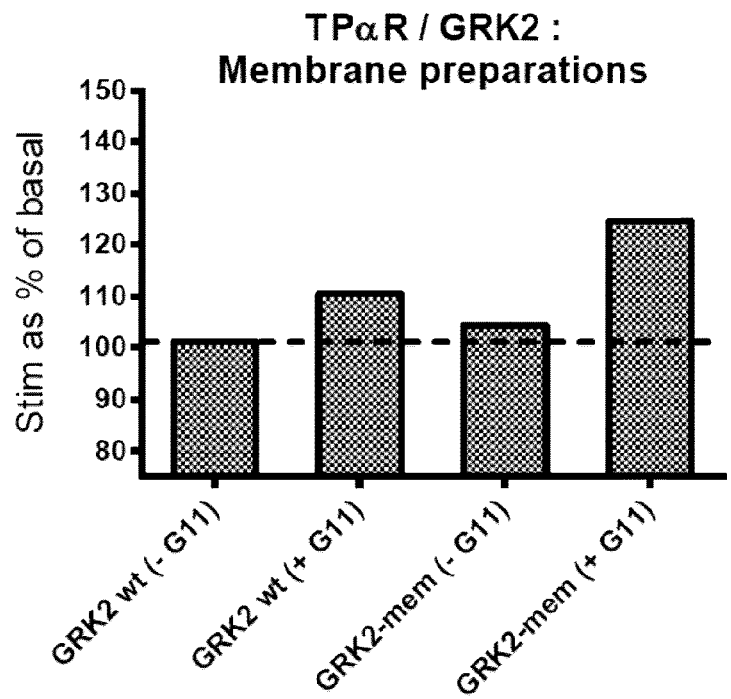

Another variant of the βγIP-based G-protein activation biosensor was developed, in which the GRK2 protein is tethered at the plasma membrane (PM) (FIG. 12A). This construct may be useful for some specific applications where in vitro experiments on membrane preparations would be preferred to whole cell experiments, such as for screening applications. To validate this approach, BRET experiments where performed on membrane preparations expressing TPαR, Gα$_{11}$, Gβ1, Rluc-Gγ5, and either the cytoplasmic form of GRK2-GFP used previously (GRK2 wt in FIG. 12B) or the plasma membrane anchored GRK2-GFP (GRK2-mem). A superior modulation of the BRET signal was observed with the membrane tethered GRK2, relative to the wt GRK2 (FIG. 12B), for which only marginal BRET increase was detected upon ligand stimulation. These results validate the use of a PM-anchored βγIP to measure G-protein activation on membrane preparations.

Figure 13A:
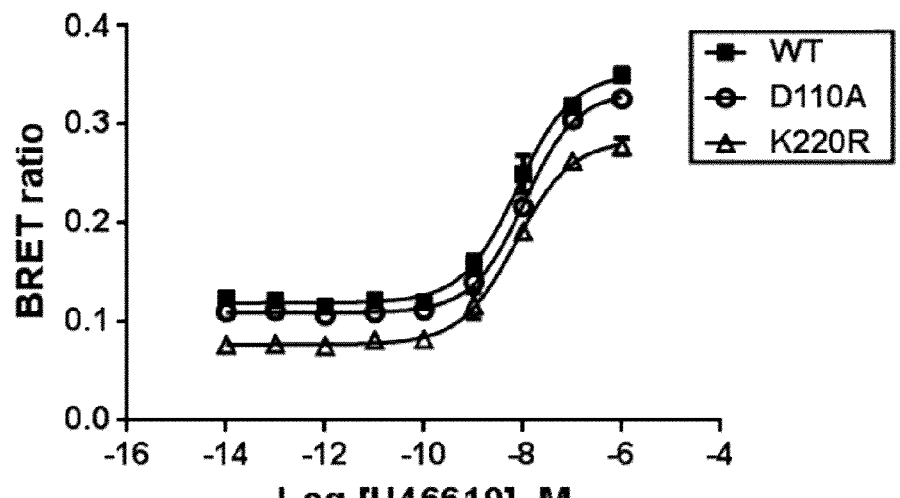
FIGS. 13A to 13C show that substitutions reported for affecting GRK2 functions (RGS and catalytic) or its regulation by phosphorylation, do not prevent nor significantly promote its recruitment to activated G-proteins.
Figure 13B:
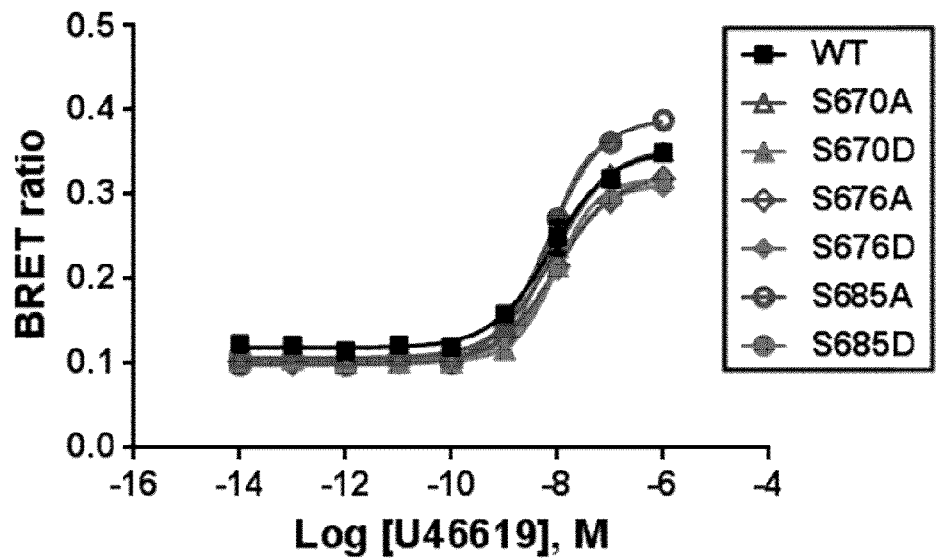
Figure 13C:
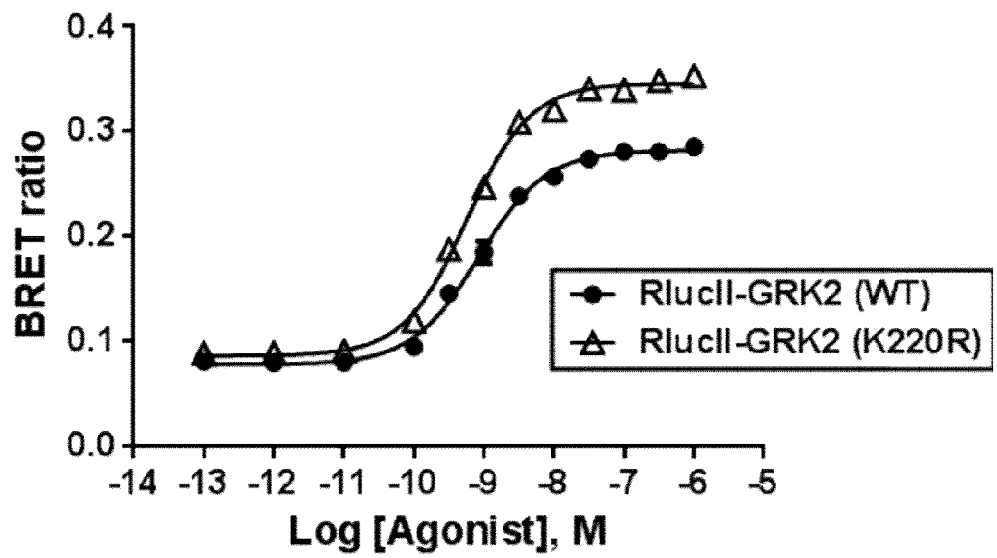

The results depicted in FIGS. 13A to 13C show that mutations reported to affect GRK2 functions, such as the D110A substitution in the RGS domain (RGS-dead mutant) and the K220R substitution in the catalytic domain (catalytic-dead mutant), or its regulation by phosphorylation (such as the S670A, S676A and S685A substitutions, or the S670D, S676D and S685D substitutions, that respectively prevent and mimic phosphorylation of GRK2's C-terminal binding domain by ERK, PKA and CDK2-CyclinA, do not prevent nor significantly promote its recruitment to activated G-proteins, as assessed using a βγIP-based G-protein activation biosensor. GRK2 variants comprising the above-noted mutations are recruited to a similar extent as native GRK2 (FIGS. 13A to 13C), thus providing evidence that GRK2 recruitment to Gβγ could be insensitive to regulation by different signaling events. Similar results were obtained with the GRK2 D110A mutant following activation of AT1R with angiotensin II.

Figure 15B:
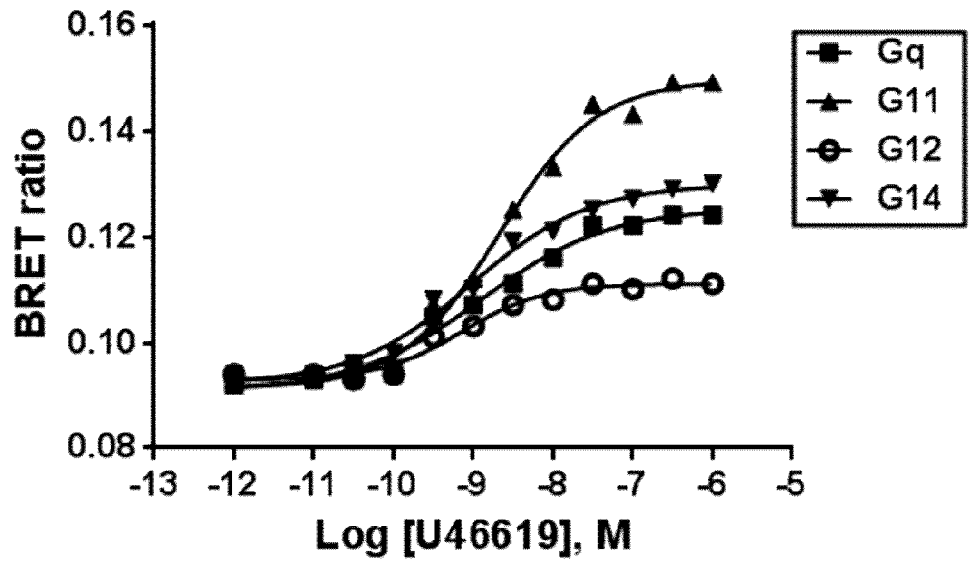
FIGS. 15B and 15C show dose-response curves for G-protein activation, obtained with the biosensor described in FIG. 15A. HEK293 cells co-expressing TPαR-RlucII, different Gα ($G\alpha_q$=solid square, $G\alpha_{11}$=solid triangle, $G\alpha_{14}$=solid diamond and $G\alpha_{12}$=empty circle), Gβ1, Gγ5 and, either the WT GRK2-GFP (FIG. 15B) or the mutant D110A GRK2-GFP (FIG. 15C), were stimulated with increasing doses of U46619. The dose-response curves show similar profiles in FIGS. 15B and 15C indicating, as in FIGS. 11B and 13A but with a different biosensor configuration, that a functional RGS is not required to recruit a βγIP to an activated G-protein.
Figure 15C:
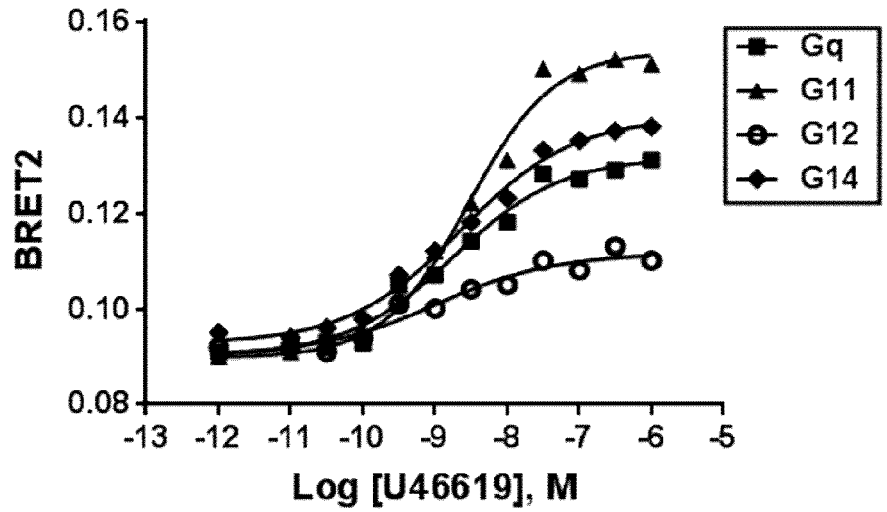

Another biosensor to measure the competition between Gα subunits and βγIP for their binding to Gβγ subunits was developed; FIG. 15A shows the configuration and principle of such biosensor. The biosensor comprises a βγIP (GRK) tagged with a RET donor or acceptor (a RET acceptor (A) is illustrated) and a GPCR tagged at its C-terminal with a RET donor or acceptor (a RET donor (D) is illustrated). While in the inactive form, the Gα subunit of the heterotrimeric G-protein is tightly bound to the Gβγ dimer. Upon ligand (L) binding to the GPCR, the Gα dissociates from the Gβγ subunits, allowing βγIP to be recruited to the free Gβγ subunits and bringing the BRET acceptor in close proximity to the BRET donor RLuc linked to the GPCR, thus inducing/increasing the BRET signal. FIGS. 15B and 15C show dose-response curves for G-protein activation, obtained with a biosensor according to FIG. 15A, comprising a wild-type GRK2 (FIG. 15A) or the RGS-dead GRK2 mutant (D110A) (FIG. 15B). The dose-response curves showed similar profiles in FIGS. 15B and 15C indicating that a functional RGS is not required to recruit a βγIP to an activated G-protein, confirming the results presented in FIGS. 11B and 13A using a different biosensor configuration.

Figure 16A:
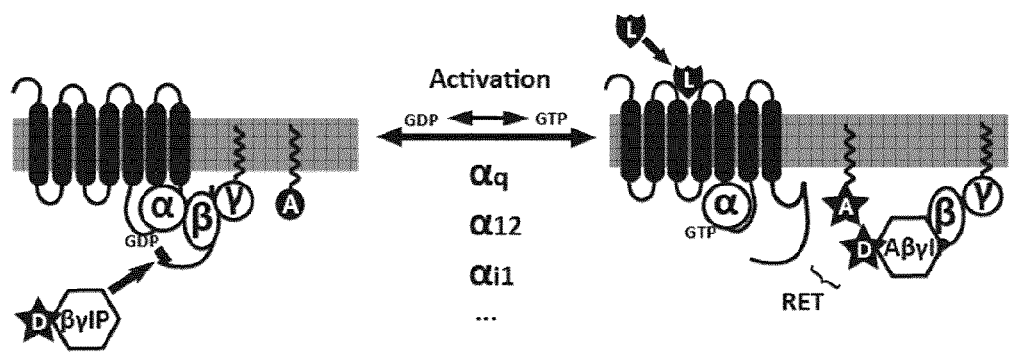
FIG. 16A shows a schematic diagram illustrating a biosensor comprising a βγIP (GRK) tagged with the RET donor (D) and a plasma-membrane marker: a RET acceptor (A) tagged with a plasma-membrane targeting and anchoring sequence (e.g., a CAAX domain). The assay is also based on the competition between the Gα subunit and the βγIP for the binding to the Gβγ dimer, at the plasma-membrane. While in the inactive form, the Gα subunit of the heterotrimeric G-protein is tightly bound to the Gβγ dimer. Upon ligand binding to the GPCR, the Gα dissociates from the Gβγ subunits, allowing βγIP to be recruited to the free Gβγ subunits, at the plasma-membrane which, leads to an increase in density of RET donor (βγIP-D) and acceptor (plasma-membrane marker, A-CAAX), thus inducing/increasing the BRET signal.
Figure 16B:
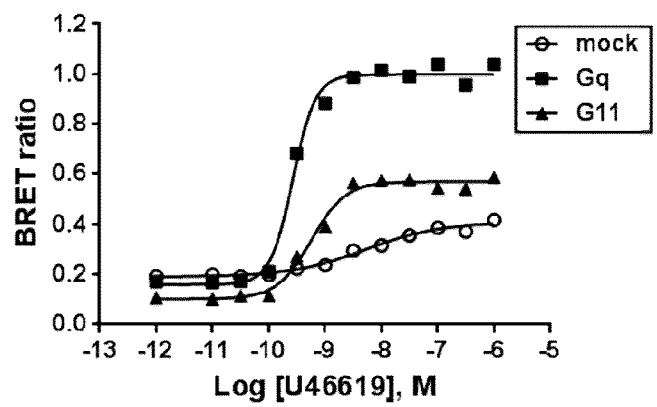
FIG. 16B shows dose-response curves for G-protein activation, obtained with the biosensor described in FIG. 16A. HEK293 cells co-expressing TPαR, different Gα ($G\alpha_q$=solid square, $G\alpha_{11}$=solid triangle, Mock condition (no Gα)=empty circle), Gβ1, Gγ5, RlucII-GRK2 and rGFP-CAAX, were stimulated with increasing doses of U46619. Dose-response curves in FIG. 16B are similar to those obtained in FIGS. 3C, 9B and 11C with different configuration of biosensors.

Another biosensor to measure the competition between Gα subunits and βγIP for their binding to Gβγ subunits was developed; FIG. 16A shows the configuration and principle of such biosensor. The biosensor comprises a βγIP (e.g., GRK) tagged with a RET donor or acceptor (a RET donor (D) is illustrated) and a plasma membrane (PM)-targeting domain tagged with a RET donor or acceptor (a RET acceptor (A) is illustrated). While in the inactive form, the Gα subunit of the heterotrimeric G-protein is tightly bound to the Gβγ dimer. Upon ligand (L) binding to the GPCR, the Gα dissociates from the Gβγ subunits, allowing βγIP to be recruited to the free Gβγ subunits that are located at the PM, and bringing the RET donor D in close proximity to the RET acceptor A anchored to the PM, thus inducing/increasing the BRET signal. FIG. 16B shows dose-response curves for G-protein activation, obtained with a biosensor according to FIG. 16A, using HEK293 cells co-expressing TPαR, different Gα (Gα$_q$=solid square, Gα$_{11}$=solid triangle, Mock condition (no Gα)=empty circle), Gβ1, Gγ5, RlucII-GRK2 and rGFP-CAAX, stimulated with increasing doses of U46619. The dose-response curves in FIG. 16B are similar to those obtained with biosensors having a different configuration (FIGS. 3C, 9B and 11C), providing evidence that a biosensor measuring βγIP recruitment at the PM is suitable to "indirectly" assess βγIP recruitment to the free Gβγ subunits that are anchored to the PM.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Boularan, C. and J. H. Kehrl (2014). "Implications of non-canonical G-protein signaling for the immune system." *Cell Signal* 26(6): 1269-1282.
2. Galandrin, S., G. Oligny-Longpre and M. Bouvier (2007). "The evasive nature of drug efficacy: implications for drug discovery." *Trends in Pharmacological Sciences* 28(8): 423-430.
3. Garland, S. L. (2013). "Are GPCRs still a source of new targets?" *J Biomol Screen* 18(9): 947-966.
4. Gilman, A. G. (1987). "G-proteins: Transducers of receptor-generated signals." *Annu Rev Biochem* 56: 615-649.
5. Hamdan, F. F., M. D. Rochdi, B. Breton, D. Fessart, D. E. Michaud, P. G. Charest, S. A. Laporte and M. Bouvier (2007). "Unraveling G protein-coupled receptor endocytosis pathways using real-time monitoring of agonist-promoted interaction between beta-arrestins and AP-2." *J Biol Chem* 282(40): 29089-29100.
6. Hancock, J. F. (2003). "Ras proteins: different signals from different locations." *Nat Rev Mol Cell Biol* 4(5): 373-384.
7. Heydorn, A., R. J. Ward, R. Jorgensen, M. M. Rosenkilde, T. M. Frimurer, G. Milligan and E. Kostenis (2004). "Identification of a novel site within G protein alpha subunits important for specificity of receptor-G protein interaction." *Mol Pharmacol* 66(2): 250-259.
8. Kenakin, T. and A. Christopoulos (2013). "Signaling bias in new drug discovery: detection, quantification and therapeutic impact." *Nat Rev Drug Discov* 12(3): 205-216.
9. Leduc, M., B. Breton, C. Gales, C. Le Gouill, M. Bouvier, S. Chemtob and N. Heveker (2009). "Functional selectivity of natural and synthetic prostaglandin EP4 receptor ligands." *J Pharmacol Exp Ther* 331(1): 297-307.
10. Mercier, J. F., A. Salahpour, S. Angers, A. Breit and M. Bouvier (2002). "Quantitative assessment of the beta 1 and beta 2-adrenergic receptor homo and hetero-dimerization by bioluminescence resonance energy transfer." *J Biol Chem* 277: 44925-44931.
11. Pitcher, J. A., J. Inglese, J. B. Higgins, J. L. Arriza, P. J. Casey, C. Kim, J. L. Benovic, M. M. Kwatra, M. G. Caron and R. J. Lefkowitz (1992). "Role of beta gamma subunits of G proteins in targeting the beta-adrenergic receptor kinase to membrane-bound receptors." *Science* 257 (5074): 1264-1267.
12. Stefan, E., S. Aquin, N. Berger, C. R. Landry, B. Nyfeler, M. Bouvier and S. W. Michnick (2007). "Quantification of dynamic protein complexes using *Renilla* luciferase fragment complementation applied to protein kinase A activities in vivo." *Proc Natl Acad Sci USA* 104(43): 16916-16921.
13. Takasaki, J., T. Saito, M. Taniguchi, T. Kawasaki, Y. Moritani, K. Hayashi and M. Kobori (2004). "A novel Galphaq/11-selective inhibitor." *J Biol Chem* 279(46): 47438-47445.
14. Touhara, K., J. Inglese, J. A. Pitcher, G. Shaw and R. J. Lefkowitz (1994). "Binding of G protein beta gamma-subunits to pleckstrin homology domains." *J Biol Chem* 269(14): 10217-10220.
15. Zhang, J. H., T. D. Chung and K. R. Oldenburg (1999). "A Simple Statistical Parameter for Use in Evaluation and Validation of High Throughput Screening Assays." *J Biomol Screen* 4(2): 67-73.
16. Cong et al., *The Journal of Biological Chemistry*, 276, 15192-15199.
17. Pitcher et al., *The Journal of Biological Chemistry*, 274, 34531-34534.
18. Penela et al., *PNAS*, 107(3): 1118-1123.
19. Choudhary et al., *Mol Cell.* 2009 36(2): 326-39.
20. Linding et al., GlobPlot: exploring protein sequences for globularity and disorder, *Nucleic Acid Res* 2003—Vol. 31, No. 13, 3701-8.

---

What is claimed is:

1. A biosensor system for detecting G-protein activity, said biosensor system comprising:
   (i) a first biosensor comprising:
      a first component comprising a GRK2 or GRK3 protein fused to the amino-terminal of (a) a bioluminescence resonance energy transfer (BRET) donor; or (b) a BRET acceptor; and
      a second component comprising a Gβ protein and a Gγ5 protein, wherein said Gγ5 protein is fused to the carboxy-terminal of (a) a BRET donor; or (b) a BRET acceptor;
   (ii) a second biosensor comprising:
      the first and second components defined in (i); and
      a third component comprising a recombinant Gα protein;
   wherein (a) if said GRK2 or GRK3 protein is fused to said BRET donor, said Gγ5 protein is fused to said BRET acceptor; (b) if said GRK2 or GRK3 protein is fused to said BRET acceptor, said Gγ5 protein is fused to said BRET donor.

2. The biosensor system of claim 1, wherein said GRK2 or GRK3 protein is fused to said BRET acceptor and said Gγ5 protein is fused to said BRET donor.

3. The biosensor system of claim 1, wherein said BRET donor is a bioluminescent protein.

4. The biosensor system of claim 3, wherein said bioluminescent protein is a luciferase.

5. The biosensor system of claim 1, wherein said BRET acceptor is a green fluorescent protein (GFP).

6. The biosensor system of claim 1, wherein the first component further comprises a plasma membrane (PM)-targeting moiety fused to (i) said GRK2 or GRK3 protein or (ii) said BRET donor or BRET acceptor.

7. The biosensor system of claim 6, wherein said PM-targeting moiety is fused at the C-terminus of said BRET donor or BRET acceptor.

8. The biosensor system of claim 6, further comprising a flexible linker between (i) said BRET donor or BRET acceptor and (ii) said PM-targeting moiety.

9. The biosensor system of claim 8, wherein said flexible linker has a length corresponding to about 50 to about 500 amino acids.

10. The biosensor system of claim 1, wherein said recombinant Gα protein is human $G\alpha_q$, $G\alpha_s$, $G\alpha_{i1}$, $G\alpha_{i2}$, $G\alpha_{i3}$, $G\alpha_{t\text{-}cone}$, $G\alpha_{t\text{-}rod}$, $G\alpha_{t\text{-}gust}$, $G\alpha_z$, $G\alpha_{oA}$, $G\alpha_{oB}$, $G\alpha_{olf}$, $G\alpha_{11}$, $G\alpha_{12}$, $G\alpha_{13}$, $G\alpha_{14}$, and $G\alpha_{15}/G\alpha_{16}$ protein, or promiscuous or non-selective Gα variant thereof.

11. The biosensor system of claim 1, wherein said first component comprises a GRK2 protein.

12. The biosensor system of claim 1, wherein the Gβ protein in said first and second biosensors is a recombinant Gβ protein.

13. The biosensor system of claim 1, wherein the biosensor system further comprises a G-protein-coupled receptor (GPCR).

14. The biosensor system of claim 1, wherein the biosensor system comprises a plurality of second biosensors, wherein each of said second biosensors comprises a different recombinant Gα protein.

15. The biosensor system of claim 14, wherein said different recombinant Gα proteins are at least two of the following Gα proteins: $G\alpha_q$, $G\alpha_s$, $G\alpha_{i1}$, $G\alpha_{i2}$, $G\alpha_{i3}$, $G\alpha_{t\text{-}cone}$, $G\alpha_{t\text{-}rod}$, $G\alpha_{t\text{-}gust}$, $G\alpha_z$, $G\alpha_{oA}$, $G\alpha_{oB}$, $G\alpha_{olf}$, $G\alpha_{11}$, $G\alpha_{12}$, $G\alpha_{13}$, $G\alpha_{14}$, and $G\alpha_{15}/G\alpha_{16}$.

16. A method for determining whether a Gα protein is activated by a GPCR agonist, said method comprising:
   (a) measuring the signal emitted by said BRET acceptor or reporter protein in the presence and absence of said GPCR agonist in the first and second biosensors of the biosensor system of claim 1, and
   (b) identifying whether the Gα protein is activated by said GPCR agonist based on the signal emitted by said BRET acceptor;
   wherein a higher increase of the signal measured in the presence of the GPCR agonist in said second biosensor relative to said first biosensor is indicative that the Gα protein is activated by said GPCR agonist, and wherein a similar or lower increase, or a decrease, of the signal measured in the presence of the GPCR agonist in said second biosensor relative to said first biosensor is indicative that said the Gα protein is not activated by said GPCR agonist.

17. A method for determining whether a test agent is an inhibitor or activator of a Gα protein of interest, said method comprising:
   (1) contacting the second biosensor(s) defined in claim 1 with a GPCR agonist or antagonist, wherein said recombinant Gα protein corresponds to said Gα protein of interest;
   (2) measuring the signal emitted by said BRET acceptor in the presence and absence of said test agent; and
   (3) determining whether said test agent is an inhibitor or activator of said Gα protein,
   wherein (i) a lower signal measured in the presence of the test agent following contacting with said GPCR agonist is indicative that said test agent is an inhibitor of said Gα protein of interest, and a similar or higher signal measured in the presence of the test agent following contacting with said GPCR agonist is indicative that said test agent is not an inhibitor of said Gα protein of interest; or (ii) a higher signal measured in the presence of the test agent following contacting with said GPCR antagonist is indicative that said test agent is an activator of said Gα protein of interest, and a similar or lower signal measured in the presence of the test agent following contacting with said GPCR antagonist is indicative that said test agent is not an activator of said Gα protein of interest.

\* \* \* \* \*

SEQUENCE LISTING

<160> NUMBER OF SEQ ID NOS: 53

<210> SEQ ID NO 1
<211> LENGTH: 55
<212> TYPE: PRT
<213> ORGANISM: Homo sapiens

<400> SEQUENCE: 1

Leu Lys Leu Leu Leu Leu Gly Thr Gly Glu Ser Gly Lys Ser Thr Phe
1               5                   10                  15

Ile Lys Gln Met Arg Ile Ile His Gly Ser Gly Tyr Ser Asp Glu Asp
            20                  25                  30

Lys Arg Gly Phe Thr Lys Leu Val Tyr Gln Asn Ile Phe Thr Ala Met
        35                  40                  45

Gln Ala Met Ile Arg Ala Met
    50                  55

<210> SEQ ID NO 2
<211> LENGTH: 55
<212> TYPE: PRT
<213> ORGANISM: Homo sapiens

<400> SEQUENCE: 2

```
Leu Lys Leu Leu Leu Leu Gly Thr Gly Glu Ser Gly Lys Ser Thr Phe
1               5                   10                  15

Ile Lys Gln Met Arg Ile Ile His Gly Ala Gly Tyr Ser Glu Glu Asp
            20                  25                  30

Lys Arg Gly Phe Thr Lys Leu Val Tyr Gln Asn Ile Phe Thr Ala Met
            35                  40                  45

Gln Ala Met Ile Arg Ala Met
    50                  55
```

<210> SEQ ID NO 3
<211> LENGTH: 55
<212> TYPE: PRT
<213> ORGANISM: Homo sapiens

<400> SEQUENCE: 3

```
Leu Lys Leu Leu Leu Leu Gly Thr Gly Glu Ser Gly Lys Ser Thr Phe
1               5                   10                  15

Ile Lys Gln Met Arg Ile Ile His Gly Ser Gly Tyr Ser Asp Glu Asp
            20                  25                  30

Arg Lys Gly Phe Thr Lys Leu Val Tyr Gln Asn Ile Phe Thr Ala Met
            35                  40                  45

Gln Ala Met Ile Arg Ala Met
    50                  55
```

<210> SEQ ID NO 4
<211> LENGTH: 55
<212> TYPE: PRT
<213> ORGANISM: Homo sapiens

<400> SEQUENCE: 4

```
Leu Lys Leu Leu Leu Leu Gly Pro Gly Glu Ser Gly Lys Ser Thr Phe
1               5                   10                  15

Ile Lys Gln Met Arg Ile Ile His Gly Ala Gly Tyr Ser Glu Glu Glu
            20                  25                  30

Arg Lys Gly Phe Arg Pro Leu Val Tyr Gln Asn Ile Phe Val Ser Met
            35                  40                  45

Arg Ala Met Ile Glu Ala Met
    50                  55
```

<210> SEQ ID NO 5
<211> LENGTH: 55
<212> TYPE: PRT
<213> ORGANISM: Homo sapiens

<400> SEQUENCE: 5

```
Val Lys Leu Leu Leu Leu Gly Ala Gly Glu Ser Gly Lys Ser Thr Ile
1               5                   10                  15

Val Lys Gln Met Lys Ile Ile His Glu Asp Gly Phe Ser Gly Glu Asp
            20                  25                  30

Val Lys Gln Tyr Lys Pro Val Val Tyr Ser Asn Thr Ile Gln Ser Leu
            35                  40                  45

Ala Ala Ile Val Arg Ala Met
    50                  55
```

<210> SEQ ID NO 6
<211> LENGTH: 55
<212> TYPE: PRT
<213> ORGANISM: Homo sapiens

```
<400> SEQUENCE: 6

Val Lys Leu Leu Leu Leu Gly Ala Gly Glu Ser Gly Lys Ser Thr Ile
1               5                   10                  15

Val Lys Gln Met Lys Ile Ile His Glu Asp Gly Phe Ser Gly Glu Asp
                20                  25                  30

Val Lys Gln Tyr Lys Pro Val Tyr Ser Asn Thr Ile Gln Ser Leu
            35                  40                  45

Ala Ala Ile Val Arg Ala Met
        50                  55

<210> SEQ ID NO 7
<211> LENGTH: 55
<212> TYPE: PRT
<213> ORGANISM: Homo sapiens

<400> SEQUENCE: 7

Val Lys Leu Leu Leu Leu Gly Ala Gly Glu Ser Gly Lys Ser Thr Ile
1               5                   10                  15

Val Lys Gln Met Lys Ile Ile His Gln Asp Gly Tyr Ser Leu Glu Glu
                20                  25                  30

Cys Leu Glu Phe Ile Ala Ile Ile Tyr Gly Asn Thr Leu Gln Ser Ile
            35                  40                  45

Leu Ala Ile Val Arg Ala Met
        50                  55

<210> SEQ ID NO 8
<211> LENGTH: 55
<212> TYPE: PRT
<213> ORGANISM: Homo sapiens

<400> SEQUENCE: 8

Val Lys Leu Leu Leu Leu Gly Ala Gly Glu Ser Gly Lys Ser Thr Ile
1               5                   10                  15

Val Lys Gln Met Lys Ile Ile His Gln Asp Gly Tyr Ser Pro Glu Glu
                20                  25                  30

Cys Leu Glu Phe Lys Ala Ile Ile Tyr Gly Asn Val Leu Gln Ser Ile
            35                  40                  45

Leu Ala Ile Ile Arg Ala Met
        50                  55

<210> SEQ ID NO 9
<211> LENGTH: 55
<212> TYPE: PRT
<213> ORGANISM: Homo sapiens

<400> SEQUENCE: 9

Val Lys Leu Leu Leu Leu Gly Ala Gly Glu Ser Gly Lys Ser Thr Ile
1               5                   10                  15

Val Lys Gln Met Lys Ile Ile His Lys Asn Gly Tyr Ser Glu Gln Glu
                20                  25                  30

Cys Met Glu Phe Lys Ala Val Ile Tyr Ser Asn Thr Leu Gln Ser Ile
            35                  40                  45

Leu Ala Ile Val Lys Ala Met
        50                  55

<210> SEQ ID NO 10
<211> LENGTH: 55
<212> TYPE: PRT
<213> ORGANISM: Homo sapiens
```

```
<400> SEQUENCE: 10

Val Lys Leu Leu Leu Leu Gly Ala Gly Glu Ser Gly Lys Ser Thr Ile
1               5                   10                  15

Val Lys Gln Met Lys Ile Ile His Glu Ala Gly Tyr Ser Glu Glu Glu
                20                  25                  30

Cys Lys Gln Tyr Lys Ala Val Val Tyr Ser Asn Thr Ile Gln Ser Ile
            35                  40                  45

Ile Ala Ile Ile Arg Ala Met
        50              55

<210> SEQ ID NO 11
<211> LENGTH: 55
<212> TYPE: PRT
<213> ORGANISM: Homo sapiens

<400> SEQUENCE: 11

Val Lys Leu Leu Leu Leu Gly Ala Gly Glu Ser Gly Lys Ser Thr Ile
1               5                   10                  15

Val Lys Gln Met Lys Ile Ile His Glu Asp Gly Tyr Ser Glu Glu Glu
                20                  25                  30

Cys Arg Gln Tyr Arg Ala Val Val Tyr Ser Asn Thr Ile Gln Ser Ile
            35                  40                  45

Met Ala Ile Val Lys Ala Met
        50              55

<210> SEQ ID NO 12
<211> LENGTH: 55
<212> TYPE: PRT
<213> ORGANISM: Homo sapiens

<400> SEQUENCE: 12

Val Lys Leu Leu Leu Leu Gly Ala Gly Glu Ser Gly Lys Ser Thr Ile
1               5                   10                  15

Val Lys Gln Met Lys Ile Ile His Glu Asp Gly Tyr Ser Glu Asp Glu
                20                  25                  30

Cys Lys Gln Tyr Lys Val Val Val Tyr Ser Asn Thr Ile Gln Ser Ile
            35                  40                  45

Ile Ala Ile Ile Arg Ala Met
        50              55

<210> SEQ ID NO 13
<211> LENGTH: 55
<212> TYPE: PRT
<213> ORGANISM: Homo sapiens

<400> SEQUENCE: 13

Ile Lys Leu Leu Leu Leu Gly Thr Ser Asn Ser Gly Lys Ser Thr Ile
1               5                   10                  15

Val Lys Gln Met Lys Ile Ile His Ser Gly Gly Phe Asn Leu Glu Ala
                20                  25                  30

Cys Lys Glu Tyr Lys Pro Leu Ile Ile Tyr Asn Ala Ile Asp Ser Leu
            35                  40                  45

Thr Arg Ile Ile Arg Ala Leu
        50              55

<210> SEQ ID NO 14
<211> LENGTH: 55
<212> TYPE: PRT
```

<213> ORGANISM: Homo sapiens

<400> SEQUENCE: 14

Val Lys Ile Leu Leu Leu Gly Ala Gly Glu Ser Gly Lys Ser Thr Phe
1               5                   10                  15

Leu Lys Gln Met Arg Ile Ile His Gly Arg Glu Phe Asp Gln Lys Ala
            20                  25                  30

Leu Leu Glu Phe Arg Asp Thr Ile Phe Asp Asn Ile Leu Lys Gly Ser
        35                  40                  45

Arg Val Leu Val Asp Ala Arg
    50                  55

<210> SEQ ID NO 15
<211> LENGTH: 55
<212> TYPE: PRT
<213> ORGANISM: Homo sapiens

<400> SEQUENCE: 15

Val Lys Ile Leu Leu Leu Gly Ala Gly Glu Ser Gly Lys Ser Thr Phe
1               5                   10                  15

Leu Lys Gln Met Arg Ile Ile His Gly Gln Asp Phe Asp Gln Arg Ala
            20                  25                  30

Arg Glu Glu Phe Arg Pro Thr Ile Tyr Ser Asn Val Ile Lys Gly Met
        35                  40                  45

Arg Val Leu Val Asp Ala Arg
    50                  55

<210> SEQ ID NO 16
<211> LENGTH: 56
<212> TYPE: PRT
<213> ORGANISM: Homo sapiens

<400> SEQUENCE: 16

His Arg Leu Leu Leu Leu Gly Ala Gly Glu Ser Gly Lys Ser Thr Ile
1               5                   10                  15

Val Lys Gln Met Arg Ile Leu His Val Asn Gly Phe Asn Gly Asp Ser
            20                  25                  30

Glu Lys Ala Thr Lys Val Gln Asp Ile Lys Asn Asn Leu Lys Glu Ala
        35                  40                  45

Ile Glu Thr Ile Val Ala Ala Met
    50                  55

<210> SEQ ID NO 17
<211> LENGTH: 55
<212> TYPE: PRT
<213> ORGANISM: Homo sapiens

<400> SEQUENCE: 17

His Arg Leu Leu Leu Leu Gly Ala Gly Glu Ser Gly Lys Ser Thr Ile
1               5                   10                  15

Val Lys Gln Met Arg Ile Leu His Val Asn Gly Phe Asn Pro Glu Glu
            20                  25                  30

Lys Lys Gln Lys Ile Leu Asp Ile Arg Lys Asn Val Lys Asp Ala Ile
        35                  40                  45

Val Thr Ile Val Ser Ala Met
    50                  55

<210> SEQ ID NO 18
<211> LENGTH: 689

<212> TYPE: PRT
<213> ORGANISM: Homo sapiens

<400> SEQUENCE: 18

```
Met Ala Asp Leu Glu Ala Val Leu Ala Asp Val Ser Tyr Leu Met Ala
1               5                   10                  15

Met Glu Lys Ser Lys Ala Thr Pro Ala Arg Ala Ser Lys Lys Ile
            20                  25                  30

Leu Leu Pro Glu Pro Ser Ile Arg Ser Val Met Gln Lys Tyr Leu Glu
            35                  40                  45

Asp Arg Gly Glu Val Thr Phe Glu Lys Ile Phe Ser Gln Lys Leu Gly
        50                  55                  60

Tyr Leu Leu Phe Arg Asp Phe Cys Leu Asn His Leu Glu Glu Ala Arg
65                  70                  75                  80

Pro Leu Val Glu Phe Tyr Glu Glu Ile Lys Lys Tyr Glu Lys Leu Glu
                85                  90                  95

Thr Glu Glu Glu Arg Val Ala Arg Ser Arg Glu Ile Phe Asp Ser Tyr
            100                 105                 110

Ile Met Lys Glu Leu Leu Ala Cys Ser His Pro Phe Ser Lys Ser Ala
        115                 120                 125

Thr Glu His Val Gln Gly His Leu Gly Lys Lys Gln Val Pro Pro Asp
130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Ser Tyr Ala Phe His Thr Pro Asp Lys Leu Ser Phe Ile Leu Asp
            260                 265                 270

Leu Met Asn Gly Gly Asp Leu His Tyr His Leu Ser Gln His Gly Val
        275                 280                 285

Phe Ser Glu Ala Asp Met Arg Phe Tyr Ala Ala Glu Ile Ile Leu Gly
290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Lys Pro His Ala Ser Val Gly
            340                 345                 350

Thr His Gly Tyr Met Ala Pro Glu Val Leu Gln Lys Gly Val Ala Tyr
        355                 360                 365

Asp Ser Ser Ala Asp Trp Phe Ser Leu Gly Cys Met Leu Phe Lys Leu
370                 375                 380

Leu Arg Gly His Ser Pro Phe Arg Gln His Lys Thr Lys Asp Lys His
385                 390                 395                 400
```

-continued

```
Glu Ile Asp Arg Met Thr Leu Thr Met Ala Val Glu Leu Pro Asp Ser
                405                 410                 415

Phe Ser Pro Glu Leu Arg Ser Leu Leu Glu Gly Leu Leu Gln Arg Asp
            420                 425                 430

Val Asn Arg Arg Leu Gly Cys Leu Gly Arg Gly Ala Gln Glu Val Lys
        435                 440                 445

Glu Ser Pro Phe Phe Arg Ser Leu Asp Trp Gln Met Val Phe Leu Gln
    450                 455                 460

Lys Tyr Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
                485                 490                 495

Lys Leu Leu Asp Ser Asp Gln Glu Leu Tyr Arg Asn Phe Pro Leu Thr
            500                 505                 510

Ile Ser Glu Arg Trp Gln Gln Glu Val Ala Glu Thr Val Phe Asp Thr
        515                 520                 525

Ile Asn Ala Glu Thr Asp Arg Leu Glu Ala Arg Lys Lys Ala Lys Asn
    530                 535                 540

Lys Gln Leu Gly His Glu Glu Asp Tyr Ala Leu Gly Lys Asp Cys Ile
545                 550                 555                 560

Met His Gly Tyr Met Ser Lys Met Gly Asn Pro Phe Leu Thr Gln Trp
                565                 570                 575

Gln Arg Arg Tyr Phe Tyr Leu Phe Pro Asn Arg Leu Glu Trp Arg Gly
            580                 585                 590

Glu Gly Glu Ala Pro Gln Ser Leu Leu Thr Met Glu Glu Ile Gln Ser
        595                 600                 605

Val Glu Glu Thr Gln Ile Lys Glu Arg Lys Cys Leu Leu Leu Lys Ile
    610                 615                 620

Arg Gly Gly Lys Gln Phe Ile Leu Gln Cys Asp Ser Asp Pro Glu Leu
625                 630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
            660                 665                 670

Val Glu Leu Ser Lys Val Pro Leu Val Gln Arg Gly Ser Ala Asn Gly
        675                 680                 685

Leu
```

<210> SEQ ID NO 19
<211> LENGTH: 688
<212> TYPE: PRT
<213> ORGANISM: Homo sapiens

<400> SEQUENCE: 19

```
Met Ala Asp Leu Glu Ala Val Leu Ala Asp Val Ser Tyr Leu Met Ala
1               5                   10                  15

Met Glu Lys Ser Lys Ala Thr Pro Ala Ala Arg Ala Ser Lys Lys Ile
            20                  25                  30

Val Leu Pro Glu Pro Ser Ile Arg Ser Val Met Gln Lys Tyr Leu Glu
        35                  40                  45

Glu Arg His Glu Ile Thr Phe Asp Lys Ile Phe Asn Gln Arg Ile Gly
    50                  55                  60

Phe Leu Leu Phe Lys Asp Phe Cys Leu Asn Glu Ile Asn Glu Ala Val
65                  70                  75                  80
```

```
Pro Gln Val Lys Phe Tyr Glu Glu Ile Lys Glu Tyr Glu Lys Leu Glu
                85                  90                  95

Asn Glu Glu Asp Arg Leu Cys Arg Ser Arg Gln Ile Tyr Asp Thr Tyr
            100                 105                 110

Ile Met Lys Glu Leu Leu Ser Cys Ser His Pro Phe Ser Lys Gln Ala
        115                 120                 125

Val Glu His Val Gln Ser His Leu Ser Lys Lys Gln Val Thr Ser Thr
    130                 135                 140

Leu Phe Gln Pro Tyr Ile Glu Glu Ile Cys Glu Ser Leu Arg Gly Ser
145                 150                 155                 160

Ile Phe Gln Lys Phe Met Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
    210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Thr Tyr Ala Phe His Thr Pro Asp Lys Leu Cys Phe Ile Leu Asp
            260                 265                 270

Leu Met Asn Gly Gly Asp Leu His Tyr His Leu Ser Gln His Gly Val
        275                 280                 285

Phe Ser Glu Lys Glu Met Arg Phe Tyr Ala Thr Glu Ile Ile Leu Gly
    290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Pro His Ala Ser Val Gly
            340                 345                 350

Thr His Gly Tyr Met Ala Pro Glu Val Leu Gln Lys Gly Thr Ala Tyr
        355                 360                 365

Asp Ser Ser Ala Asp Trp Phe Ser Leu Gly Cys Met Leu Phe Lys Leu
    370                 375                 380

Leu Arg Gly His Ser Pro Phe Arg Gln His Lys Thr Lys Asp Lys His
385                 390                 395                 400

Glu Ile Asp Arg Met Thr Leu Thr Met Asn Val Glu Leu Pro Asp Val
                405                 410                 415

Phe Ser Pro Glu Leu Lys Ser Leu Leu Glu Gly Leu Leu Gln Arg Asp
            420                 425                 430

Val Ser Lys Arg Leu Gly Cys His Gly Gly Ser Ala Gln Glu Leu Lys
        435                 440                 445

Thr His Asp Phe Phe Arg Gly Ile Asp Trp Gln His Val Tyr Leu Gln
    450                 455                 460

Lys Tyr Pro Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
                485                 490                 495
```

-continued

```
Lys Leu Leu Asp Cys Asp Gln Glu Leu Tyr Lys Asn Phe Pro Leu Val
            500                 505                 510
Ile Ser Glu Arg Trp Gln Gln Glu Val Ala Glu Thr Val Tyr Glu Ala
        515                 520                 525
Val Asn Ala Asp Thr Asp Lys Ile Glu Ala Arg Lys Arg Ala Lys Asn
    530                 535                 540
Lys Gln Leu Gly His Glu Asp Tyr Ala Leu Gly Arg Asp Cys Ile
545                 550                 555                 560
Val His Gly Tyr Met Leu Lys Leu Gly Asn Pro Phe Leu Thr Gln Trp
                565                 570                 575
Gln Arg Arg Tyr Phe Tyr Leu Phe Pro Asn Arg Leu Glu Trp Arg Gly
            580                 585                 590
Glu Gly Glu Ser Arg Gln Ser Leu Leu Thr Met Glu Gln Ile Val Ser
        595                 600                 605
Val Glu Glu Thr Gln Ile Lys Asp Lys Lys Cys Ile Leu Leu Arg Ile
    610                 615                 620
Lys Gly Gly Lys Gln Phe Val Leu Gln Cys Glu Ser Asp Pro Glu Phe
625                 630                 635                 640
Val Gln Trp Lys Lys Glu Leu Thr Glu Thr Phe Met Glu Ala Gln Arg
                645                 650                 655
Leu Leu Arg Arg Ala Pro Lys Phe Leu Asn Lys Ser Arg Ser Ala Val
            660                 665                 670
Val Glu Leu Ser Lys Pro Pro Leu Cys His Arg Asn Ser Asn Gly Leu
        675                 680                 685
```

<210> SEQ ID NO 20
<211> LENGTH: 1386
<212> TYPE: PRT
<213> ORGANISM: Homo sapiens

<400> SEQUENCE: 20

```
Met Pro Glu Gly Ala Gln Gly Leu Ser Leu Ser Lys Pro Ser Pro Ser
1               5                   10                  15
Leu Gly Cys Gly Arg Arg Gly Glu Val Cys Asp Cys Gly Thr Val Cys
            20                  25                  30
Glu Thr Arg Thr Ala Pro Ala Ala Pro Thr Met Ala Ser Pro Arg Gly
        35                  40                  45
Ser Gly Ser Ser Thr Ser Leu Ser Thr Val Gly Ser Glu Gly Asp Pro
    50                  55                  60
Ala Pro Gly Pro Thr Pro Ala Cys Ser Ala Ser Arg Pro Glu Pro Leu
65                  70                  75                  80
Pro Gly Pro Pro Ile Arg Leu His Leu Ser Pro Val Gly Ile Pro Gly
                85                  90                  95
Ser Ala Arg Pro Ser Arg Leu Glu Arg Val Ala Arg Glu Ile Val Glu
            100                 105                 110
Thr Glu Arg Ala Tyr Val Arg Asp Leu Arg Ser Ile Val Glu Asp Tyr
        115                 120                 125
Leu Gly Pro Leu Leu Asp Gly Gly Val Leu Gly Leu Ser Val Glu Gln
    130                 135                 140
Val Gly Thr Leu Phe Ala Asn Ile Glu Asp Ile Tyr Glu Phe Ser Ser
145                 150                 155                 160
Glu Leu Leu Glu Asp Leu Glu Asn Ser Ser Ala Gly Gly Ile Ala
                165                 170                 175
Glu Cys Phe Val Gln Arg Ser Glu Asp Phe Asp Ile Tyr Thr Leu Tyr
            180                 185                 190
```

```
Cys Met Asn Tyr Pro Ser Ser Leu Ala Leu Leu Arg Glu Leu Ser Leu
        195                 200                 205

Ser Pro Pro Ala Ala Leu Trp Leu Gln Glu Arg Gln Ala Gln Leu Arg
210                 215                 220

His Ser Leu Pro Leu Gln Ser Phe Leu Leu Lys Pro Val Gln Arg Ile
225                 230                 235                 240

Leu Lys Tyr His Leu Leu Gln Glu Leu Gly Lys His Trp Ala Glu
                245                 250                 255

Gly Pro Gly Thr Gly Gly Arg Glu Met Val Glu Ala Ile Val Ser
                260                 265                 270

Met Thr Ala Val Ala Trp Tyr Ile Asn Asp Met Lys Arg Lys Gln Glu
        275                 280                 285

His Ala Ala Arg Leu Gln Glu Val Gln Arg Arg Leu Gly Gly Trp Thr
        290                 295                 300

Gly Pro Glu Leu Ser Ala Phe Gly Glu Leu Val Leu Glu Gly Ala Phe
305                 310                 315                 320

Arg Gly Gly Gly Gly Gly Pro Arg Leu Arg Gly Gly Glu Arg Leu
                325                 330                 335

Leu Phe Leu Phe Ser Arg Met Leu Leu Val Ala Lys Arg Arg Gly Leu
        340                 345                 350

Glu Tyr Thr Tyr Lys Gly His Ile Phe Cys Cys Asn Leu Ser Val Ser
        355                 360                 365

Glu Ser Pro Arg Asp Pro Leu Gly Phe Lys Val Ser Asp Leu Thr Ile
        370                 375                 380

Pro Lys His Arg His Leu Leu Gln Ala Lys Asn Gln Glu Glu Lys Arg
385                 390                 395                 400

Leu Trp Ile His Cys Leu Gln Arg Leu Phe Phe Glu Asn His Pro Ala
                405                 410                 415

Ser Ile Pro Ala Lys Ala Lys Gln Val Leu Leu Glu Asn Ser Leu His
        420                 425                 430

Cys Ala Pro Lys Ser Lys Pro Val Leu Glu Pro Leu Thr Pro Pro Leu
        435                 440                 445

Gly Ser Pro Arg Pro Arg Asp Ala Arg Ser Phe Thr Pro Gly Arg Arg
450                 455                 460

Asn Thr Ala Pro Ser Pro Gly Pro Ser Val Ile Arg Arg Gly Arg Arg
465                 470                 475                 480

Gln Ser Glu Pro Val Lys Asp Pro Tyr Val Met Phe Pro Gln Asn Ala
                485                 490                 495

Lys Pro Gly Phe Lys His Ala Gly Ser Glu Gly Glu Leu Tyr Pro Pro
                500                 505                 510

Glu Ser Gln Pro Pro Val Ser Gly Ser Ala Pro Pro Glu Asp Leu Glu
        515                 520                 525

Asp Ala Gly Pro Pro Thr Leu Asp Pro Ser Gly Thr Ser Ile Thr Glu
        530                 535                 540

Glu Ile Leu Glu Leu Leu Asn Gln Arg Gly Leu Arg Asp Pro Gly Pro
545                 550                 555                 560

Ser Thr His Asp Ile Pro Lys Phe Pro Gly Asp Ser Gln Val Pro Gly
                565                 570                 575

Asp Ser Glu Thr Leu Thr Phe Gln Ala Leu Pro Ser Arg Asp Ser Ser
                580                 585                 590

Glu Glu Glu Glu Glu Glu Glu Glu Gly Leu Glu Met Asp Glu Arg Gly
        595                 600                 605
```

```
Pro Ser Pro Leu His Val Leu Glu Gly Leu Glu Ser Ser Ile Ala Ala
    610                 615                 620
Glu Met Pro Ser Ile Pro Cys Leu Thr Lys Ile Pro Asp Val Pro Asn
625                 630                 635                 640
Leu Pro Glu Ile Pro Ser Arg Cys Glu Ile Pro Glu Gly Ser Arg Leu
                    645                 650                 655
Pro Ser Leu Ser Asp Ile Ser Asp Val Phe Glu Met Pro Cys Leu Pro
            660                 665                 670
Ala Ile Pro Ser Val Pro Asn Thr Pro Ser Leu Ser Ser Thr Pro Thr
        675                 680                 685
Leu Ser Cys Asp Ser Trp Leu Gln Gly Pro Leu Gln Glu Pro Ala Glu
    690                 695                 700
Ala Pro Ala Thr Arg Arg Glu Leu Phe Ser Gly Ser Asn Pro Gly Lys
705                 710                 715                 720
Leu Gly Glu Pro Pro Ser Gly Gly Lys Ala Gly Pro Glu Glu Asp Glu
                    725                 730                 735
Glu Gly Val Ser Phe Thr Asp Phe Gln Pro Gln Asp Val Thr Gln His
            740                 745                 750
Gln Gly Phe Pro Asp Glu Leu Ala Phe Arg Ser Cys Ser Glu Ile Arg
        755                 760                 765
Ser Ala Trp Gln Ala Leu Glu Gln Gly Gln Leu Ala Arg Pro Gly Phe
    770                 775                 780
Pro Glu Pro Leu Leu Ile Leu Glu Asp Ser Asp Leu Gly Gly Asp Ser
785                 790                 795                 800
Gly Ser Gly Lys Ala Gly Ala Pro Ser Ser Glu Arg Thr Ala Ser Arg
                    805                 810                 815
Val Arg Glu Leu Ala Arg Leu Tyr Ser Glu Arg Ile Gln Gln Met Gln
            820                 825                 830
Arg Ala Glu Thr Arg Ala Ser Ala Asn Ala Pro Arg Arg Arg Pro Arg
        835                 840                 845
Val Leu Ala Gln Pro Gln Pro Ser Pro Cys Leu Pro Gln Glu Gln Ala
    850                 855                 860
Glu Pro Gly Leu Leu Pro Ala Phe Gly His Val Leu Val Cys Glu Leu
865                 870                 875                 880
Ala Phe Pro Leu Thr Cys Ala Gln Glu Ser Val Pro Leu Gly Pro Ala
                    885                 890                 895
Val Trp Val Gln Ala Ala Ile Pro Leu Ser Lys Gln Gly Gly Ser Pro
            900                 905                 910
Asp Gly Gln Gly Leu His Val Ser Asn Leu Pro Lys Gln Asp Leu Pro
        915                 920                 925
Gly Ile His Val Ser Ala Ala Thr Leu Leu Pro Glu Gln Gly Gly Ser
    930                 935                 940
Arg His Val Gln Ala Pro Ala Ala Thr Pro Leu Pro Lys Gln Glu Gly
945                 950                 955                 960
Pro Leu His Leu Gln Val Pro Ala Leu Thr Thr Phe Ser Asp Gln Gly
                    965                 970                 975
His Pro Glu Ile Gln Val Pro Ala Thr Thr Pro Leu Pro Glu His Arg
            980                 985                 990
Ser His Met Val Ile Pro Ala Pro  Ser Thr Ala Phe Cys  Pro Glu Gln
        995                1000                 1005
Gly His  Cys Ala Asp Ile His  Val Pro Thr Thr  Pro Ala Leu Pro
    1010                 1015                 1020
Lys Glu  Ile Cys Ser Asp Phe  Thr Val Ser Val Thr  Thr Pro Val
```

1025                 1030                 1035
Pro Lys Gln Glu Gly His Leu Asp Ser Glu Ser Pro Thr Asn Ile
    1040                 1045                 1050

Pro Leu Thr Lys Gln Gly Gly Ser Arg Asp Val Gln Gly Pro Asp
    1055                 1060                 1065

Pro Val Cys Ser Gln Pro Ile Gln Pro Leu Ser Trp His Gly Ser
    1070                 1075                 1080

Ser Leu Asp Pro Gln Gly Pro Gly Asp Thr Leu Pro Pro Leu Pro
    1085                 1090                 1095

Cys His Leu Pro Asp Leu Gln Ile Pro Gly Thr Ser Pro Leu Pro
    1100                 1105                 1110

Ala His Gly Ser His Leu Asp His Arg Ile Pro Ala Asn Ala Pro
    1115                 1120                 1125

Leu Ser Leu Ser Gln Glu Leu Pro Asp Thr Gln Val Pro Ala Thr
    1130                 1135                 1140

Thr Pro Leu Pro Leu Pro Gln Val Leu Thr Asp Ile Trp Val Gln
    1145                 1150                 1155

Ala Leu Pro Thr Ser Pro Lys Gln Gly Ser Leu Pro Asp Ile Gln
    1160                 1165                 1170

Gly Pro Ala Ala Ala Pro Pro Leu Pro Glu Pro Ser Leu Thr Asp
    1175                 1180                 1185

Thr Gln Val Gln Lys Leu Thr Pro Ser Leu Glu Gln Lys Ser Leu
    1190                 1195                 1200

Ile Asp Ala His Val Pro Ala Ala Thr Pro Leu Pro Glu Arg Gly
    1205                 1210                 1215

Gly Ser Leu Asp Ile Gln Gly Leu Ser Pro Thr Pro Val Gln Thr
    1220                 1225                 1230

Thr Met Val Leu Ser Lys Pro Gly Gly Ser Leu Ala Ser His Val
    1235                 1240                 1245

Ala Arg Leu Glu Ser Ser Asp Leu Thr Pro Pro His Ser Pro Pro
    1250                 1255                 1260

Pro Ser Ser Arg Gln Leu Leu Gly Pro Asn Ala Ala Ala Leu Ser
    1265                 1270                 1275

Arg Tyr Leu Ala Ala Ser Tyr Ile Ser Gln Ser Leu Ala Arg Arg
    1280                 1285                 1290

Gln Gly Pro Gly Gly Gly Ala Pro Ala Ala Ser Arg Gly Ser Trp
    1295                 1300                 1305

Ser Ser Ala Pro Thr Ser Arg Ala Ser Ser Pro Pro Gln Pro
    1310                 1315                 1320

Gln Pro Pro Pro Pro Ala Arg Arg Leu Ser Tyr Ala Thr Thr
    1325                 1330                 1335

Val Asn Ile His Val Gly Gly Gly Arg Leu Arg Pro Ala Lys
    1340                 1345                 1350

Ala Gln Val Arg Leu Asn His Pro Ala Leu Leu Ala Ser Thr Gln
    1355                 1360                 1365

Glu Ser Met Gly Leu His Arg Ala Gln Gly Ala Pro Asp Ala Pro
    1370                 1375                 1380

Phe His Met
    1385

<210> SEQ ID NO 21
<211> LENGTH: 41
<212> TYPE: DNA
<213> ORGANISM: Artificial Sequence

```
<220> FEATURE:
<223> OTHER INFORMATION: Synthetic oligonucleotide

<400> SEQUENCE: 21
gacctgcgct agcgtttaaa cttaagcttg gtaccaccat g                          41

<210> SEQ ID NO 22
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 22
gtcatcccta ggctcgagtt agaccagatt gtactcctt                             39

<210> SEQ ID NO 23
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 23
tgagaatcat ccatgggtca rawtactctg atgaagataa aag                        43

<210> SEQ ID NO 24
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 24
cttttatctt catcagagta wtytgaccca tggatgattc tca                        43

<210> SEQ ID NO 25
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 25
gaatcatcca tgggtcagga tkstctgatg aagataaaag ggg                        43

<210> SEQ ID NO 26
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 26
aagccccttt tatcttcatc wtygtatcct gacccatgga tga                        43

<210> SEQ ID NO 27
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 27
agaatcatcc atgggtcagg atcctctgat gaagataaaa gggg                       44
```

```
<210> SEQ ID NO 28
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 28 cccctttat cttcatcaga ggatcctgac ccatggatga ttct            44

<210> SEQ ID NO 29
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 29
agaatcatcc atgggtcagg aggctctgat gaagataaaa gggg            44

<210> SEQ ID NO 30
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 30 cccctttat cttcatcaga gcctcctgac ccatggatga ttct            44

<210> SEQ ID NO 31
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 31
tctgatgaag ataaaagggg cggcaccaag ctggtgtatc agaa            44

<210> SEQ ID NO 32
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 32
ttctgataca ccagcttggt gccgcccctt ttatcttcat caga            44

<210> SEQ ID NO 33
<211> LENGTH: 5
<212> TYPE: PRT
<213> ORGANISM: Artificial Sequence
<220> FEATURE:
<223> OTHER INFORMATION: Synthetic linker

<400> SEQUENCE: 33

Gly Ser Ala Gly Thr
1               5

<210> SEQ ID NO 34
<211> LENGTH: 11
<212> TYPE: PRT
<213> ORGANISM: Artificial Sequence
<220> FEATURE:
```

<223> OTHER INFORMATION: Synthetic linker

<400> SEQUENCE: 34

Gly Ser Ala Gly Thr Gly Lys Leu Pro Ala Thr
1               5                   10

<210> SEQ ID NO 35
<211> LENGTH: 18
<212> TYPE: PRT
<213> ORGANISM: Artificial Sequence
<220> FEATURE:
<223> OTHER INFORMATION: Synthetic linker

<400> SEQUENCE: 35

Gly Ser Ala Gly Trp Gly Lys Leu Gly Ser Ala Gly Ser Gly Ser Ala
1               5                   10                  15

Gly Ser

<210> SEQ ID NO 36
<211> LENGTH: 11
<212> TYPE: PRT
<213> ORGANISM: Artificial Sequence
<220> FEATURE:
<223> OTHER INFORMATION: Synthetic linker

<400> SEQUENCE: 36

Gly Ser Ala Gly Thr Gly Ser Ala Gly Thr Thr
1               5                   10

<210> SEQ ID NO 37
<211> LENGTH: 14
<212> TYPE: PRT
<213> ORGANISM: Homo sapiens

<400> SEQUENCE: 37

Lys Lys Lys Lys Lys Lys Ser Lys Thr Lys Cys Val Ile Met
1               5                   10

<210> SEQ ID NO 38
<211> LENGTH: 239
<212> TYPE: PRT
<213> ORGANISM: Aequorea victoria

<400> SEQUENCE: 38

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr

```
                    130                 135                 140
Asn Tyr Asn Pro His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Phe Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 39
<211> LENGTH: 311
<212> TYPE: PRT
<213> ORGANISM: Renilla reniformis

<400> SEQUENCE: 39

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270
```

Phe Pro Asn Thr Glu Phe Val Lys Val Lys Gly Leu His Phe Ser Gln
            275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310

<210> SEQ ID NO 40
<211> LENGTH: 20
<212> TYPE: PRT
<213> ORGANISM: Homo sapiens

<400> SEQUENCE: 40

Lys Leu Asn Pro Pro Asp Glu Ser Gly Pro Gly Cys Met Ser Cys Lys
1               5                   10                  15

Cys Val Leu Ser
            20

<210> SEQ ID NO 41
<211> LENGTH: 20
<212> TYPE: PRT
<213> ORGANISM: Homo sapiens

<400> SEQUENCE: 41

Lys Leu Asn Ser Ser Asp Asp Gly Thr Gln Gly Cys Met Gly Leu Pro
1               5                   10                  15

Cys Val Val Met
            20

<210> SEQ ID NO 42
<211> LENGTH: 20
<212> TYPE: PRT
<213> ORGANISM: Homo sapiens

<400> SEQUENCE: 42

Lys Ile Ser Lys Glu Glu Lys Thr Pro Gly Cys Val Lys Ile Lys Lys
1               5                   10                  15

Cys Ile Ile Met
            20

<210> SEQ ID NO 43
<211> LENGTH: 20
<212> TYPE: PRT
<213> ORGANISM: Homo sapiens

<400> SEQUENCE: 43

Lys Met Ser Lys Asp Gly Lys Lys Lys Lys Lys Ser Lys Thr Lys
1               5                   10                  15

Cys Val Ile Met
            20

<210> SEQ ID NO 44
<211> LENGTH: 9
<212> TYPE: PRT
<213> ORGANISM: Homo sapiens

<400> SEQUENCE: 44

Cys Met Ser Cys Lys Cys Cys Ile Leu
1               5

<210> SEQ ID NO 45
<211> LENGTH: 21

```
<212> TYPE: PRT
<213> ORGANISM: Homo sapiens

<400> SEQUENCE: 45

Ser Pro Lys Lys Gly Leu Leu Gln Arg Leu Phe Lys Arg Gln His Gln
1               5                   10                  15

Asn Asn Ser Lys Ser
            20

<210> SEQ ID NO 46
<211> LENGTH: 233
<212> TYPE: PRT
<213> ORGANISM: Renilla reniformis

<400> SEQUENCE: 46

Met Asp Leu Ala Lys Leu Gly Leu Lys Glu Val Met Pro Thr Lys Ile
1               5                   10                  15

Asn Leu Glu Gly Leu Val Gly Asp His Ala Phe Ser Met Glu Gly Val
            20                  25                  30

Gly Glu Gly Asn Ile Leu Glu Gly Thr Gln Glu Val Lys Ile Ser Val
        35                  40                  45

Thr Lys Gly Ala Pro Leu Pro Phe Ala Phe Asp Ile Val Ser Val Ala
    50                  55                  60

Phe Ser Tyr Gly Asn Arg Ala Tyr Thr Gly Tyr Pro Glu Glu Ile Ser
65                  70                  75                  80

Asp Tyr Phe Leu Gln Ser Phe Pro Glu Gly Phe Thr Tyr Glu Arg Asn
                85                  90                  95

Ile Arg Tyr Gln Asp Gly Gly Thr Ala Ile Val Lys Ser Asp Ile Ser
            100                 105                 110

Leu Glu Asp Gly Lys Phe Ile Val Asn Val Asp Phe Lys Ala Lys Asp
        115                 120                 125

Leu Arg Arg Met Gly Pro Val Met Gln Gln Asp Ile Val Gly Met Gln
    130                 135                 140

Pro Ser Tyr Glu Ser Met Tyr Thr Asn Val Thr Ser Val Ile Gly Glu
145                 150                 155                 160

Cys Ile Ile Ala Phe Lys Leu Gln Thr Gly Lys His Phe Thr Tyr His
                165                 170                 175

Met Arg Thr Val Tyr Lys Ser Lys Lys Pro Val Glu Thr Met Pro Leu
            180                 185                 190

Tyr His Phe Ile Gln His Arg Leu Val Lys Thr Asn Val Asp Thr Ala
        195                 200                 205

Ser Gly Tyr Val Val Gln His Glu Thr Ala Ile Ala Ala His Ser Thr
    210                 215                 220

Ile Lys Lys Ile Glu Gly Ser Leu Pro
225                 230

<210> SEQ ID NO 47
<211> LENGTH: 14
<212> TYPE: PRT
<213> ORGANISM: Artificial Sequence
<220> FEATURE:
<223> OTHER INFORMATION: synthetic linker

<400> SEQUENCE: 47

Gly Ser Ala Gly Thr Met Ala Ser Asn Asn Thr Ala Ser Gly
1               5                   10

<210> SEQ ID NO 48
```

```
<211> LENGTH: 9
<212> TYPE: PRT
<213> ORGANISM: Artificial Sequence
<220> FEATURE:
<223> OTHER INFORMATION: synthetic linker

<400> SEQUENCE: 48

Gly Gly Ser Gly Ser Gly Ser Gly Ser
1               5

<210> SEQ ID NO 49
<211> LENGTH: 8
<212> TYPE: PRT
<213> ORGANISM: Homo sapiens

<400> SEQUENCE: 49

Asp Arg Val Tyr Ile His Pro Phe
1               5

<210> SEQ ID NO 50
<211> LENGTH: 194
<212> TYPE: PRT
<213> ORGANISM: Homo sapiens

<400> SEQUENCE: 50

Ile Lys Leu Leu Asp Ser Asp Gln Glu Leu Tyr Arg Asn Phe Pro Leu
1               5                   10                  15

Thr Ile Ser Glu Arg Trp Gln Gln Glu Val Ala Glu Thr Val Phe Asp
            20                  25                  30

Thr Ile Asn Ala Glu Thr Asp Arg Leu Glu Ala Arg Lys Lys Ala Lys
        35                  40                  45

Asn Lys Gln Leu Gly His Glu Glu Asp Tyr Ala Leu Gly Lys Asp Cys
    50                  55                  60

Ile Met His Gly Tyr Met Ser Lys Met Gly Asn Pro Phe Leu Thr Gln
65                  70                  75                  80

Trp Gln Arg Arg Tyr Phe Tyr Leu Phe Pro Asn Arg Leu Glu Trp Arg
                85                  90                  95

Gly Glu Gly Glu Ala Pro Gln Ser Leu Leu Thr Met Glu Glu Ile Gln
            100                 105                 110

Ser Val Glu Glu Thr Gln Ile Lys Glu Arg Lys Cys Leu Leu Leu Lys
        115                 120                 125

Ile Arg Gly Gly Lys Gln Phe Ile Leu Gln Cys Asp Ser Asp Pro Glu
    130                 135                 140

Leu Val Gln Trp Lys Lys Glu Leu Arg Asp Ala Tyr Arg Glu Ala Gln
145                 150                 155                 160

Gln Leu Val Gln Arg Val Pro Lys Met Lys Asn Lys Pro Arg Ser Pro
                165                 170                 175

Val Val Glu Leu Ser Lys Val Pro Leu Val Gln Arg Gly Ser Ala Asn
            180                 185                 190

Gly Leu

<210> SEQ ID NO 51
<211> LENGTH: 193
<212> TYPE: PRT
<213> ORGANISM: Homo sapiens

<400> SEQUENCE: 51

Ile Lys Leu Leu Asp Cys Asp Gln Glu Leu Tyr Lys Asn Phe Pro Leu
1               5                   10                  15
```

```
Val Ile Ser Glu Arg Trp Gln Gln Glu Val Thr Glu Thr Val Tyr Glu
            20                  25                  30

Ala Val Asn Ala Asp Thr Asp Lys Ile Glu Ala Arg Lys Arg Ala Lys
        35                  40                  45

Asn Lys Gln Leu Gly His Glu Glu Asp Tyr Ala Leu Gly Lys Asp Cys
    50                  55                  60

Ile Met His Gly Tyr Met Leu Lys Leu Gly Asn Pro Phe Leu Thr Gln
65                  70                  75                  80

Trp Gln Arg Arg Tyr Phe Tyr Leu Phe Pro Asn Arg Leu Glu Trp Arg
                85                  90                  95

Gly Glu Gly Glu Ser Arg Gln Asn Leu Leu Thr Met Glu Gln Ile Leu
            100                 105                 110

Ser Val Glu Glu Thr Gln Ile Lys Asp Lys Lys Cys Ile Leu Phe Arg
        115                 120                 125

Ile Lys Gly Gly Lys Gln Phe Val Leu Gln Cys Glu Ser Asp Pro Glu
    130                 135                 140

Phe Val Gln Trp Lys Lys Glu Leu Asn Glu Thr Phe Lys Glu Ala Gln
145                 150                 155                 160

Arg Leu Leu Arg Arg Ala Pro Lys Phe Leu Asn Lys Pro Arg Ser Gly
                165                 170                 175

Thr Val Glu Leu Pro Lys Pro Ser Leu Cys His Arg Asn Ser Asn Gly
            180                 185                 190

Leu

<210> SEQ ID NO 52
<211> LENGTH: 7
<212> TYPE: PRT
<213> ORGANISM: Homo sapiens

<400> SEQUENCE: 52

Gly Ser Ala Gly Thr Gly Gly
1               5

<210> SEQ ID NO 53
<211> LENGTH: 200
<212> TYPE: PRT
<213> ORGANISM: Artificial Sequence
<220> FEATURE:
<223> OTHER INFORMATION: synthetic linker

<400> SEQUENCE: 53

Ser Asn Ser Glu Glu Gly Pro Ala Arg Gly Lys Pro Ala Pro Glu Glu
1               5                   10                  15

Pro Asp Glu Gln Leu Gly Glu Pro Glu Ala Gln Gly Glu His Ala
            20                  25                  30

Asp Glu Pro Ala Pro Ser Lys Pro Ser Glu Lys His Met Val Pro Gln
        35                  40                  45

Met Ala Glu Pro Glu Lys Gly Glu Glu Ala Arg Glu Pro Gln Gly Ala
    50                  55                  60

Glu Asp Lys Pro Ala Pro Val His Lys Pro Lys Lys Glu Glu Pro Gln
65                  70                  75                  80

Arg Pro Asn Glu Glu Lys Ala Pro Lys Pro Lys Gly Arg His Val Gly
                85                  90                  95

Arg Gln Glu Asn Asp Asp Ser Ala Gly Lys Pro Glu Pro Gly Arg Pro
            100                 105                 110

Asp Arg Lys Gly Lys Glu Lys Glu Pro Glu Glu Pro Ala Gln Gly
        115                 120                 125
```

```
His Ser Leu Pro Gln Glu Pro Glu Pro Met Pro Arg Pro Lys Pro Glu
    130                 135                 140

Val Arg Lys Lys Pro His Pro Gly Ala Ser Pro His Gln Val Ser Asp
145                 150                 155                 160

Val Glu Asp Ala Lys Gly Pro Glu Arg Lys Val Asn Pro Met Glu Gly
                165                 170                 175

Glu Glu Ser Ala Lys Gln Ala Gln Gln Glu Gly Pro Ala Glu Asn Asp
            180                 185                 190

Glu Ala Glu Arg Pro Glu Arg Pro
            195             200
```